United States Patent [19]

Morokawa

[11] 4,337,529
[45] Jun. 29, 1982

[54] PACE TIMING DEVICE

[75] Inventor: Shigeru Morokawa, Tokorozawa, Japan

[73] Assignee: Citizen Watch Company Limited, Tokyo, Japan

[21] Appl. No.: 41,564

[22] Filed: May 23, 1979

[30] Foreign Application Priority Data

May 27, 1978 [JP] Japan .................................. 53-063705

[51] Int. Cl.³ .................. G04B 47/00; G04F 8/00; G04C 2/16; G08B 3/10
[52] U.S. Cl. ..................................... 368/10; 368/109; 368/251; 340/309.1; 340/323 R
[58] Field of Search ............... 368/3, 10, 12, 72–73, 368/107–111, 113–114, 121, 155–160, 250–251; 340/309.1, 309.4, 323, 384 E; 364/561, 569, 705, 710; 235/92 GA, 92 T

[56] References Cited

U.S. PATENT DOCUMENTS

| 3,624,926 | 12/1971 | McCaugaey | 368/110 |
| 3,908,353 | 9/1975 | Graziano | 368/156 |
| 3,979,698 | 9/1976 | Gollinger | 368/159 X |
| 4,014,167 | 3/1977 | Hasegawa et al. | 84/484 |
| 4,053,755 | 10/1977 | Sherrill | 364/561 |
| 4,164,732 | 8/1979 | Pischiera | 340/323 R |
| 4,216,956 | 8/1980 | Yamamura et al. | 340/323 R X |
| 4,220,996 | 9/1980 | Searcy | 364/561 |

Primary Examiner—Vit W. Miska
Attorney, Agent, or Firm—Jordan and Hamburg

[57] ABSTRACT

A pace timing device for timing steps or other actions during physical exercise, providing audible tone bursts as timing information, and equipped with means for setting the repetition rate and rhythm of the tone bursts to suitable values. Audible and visible indications can be given of elapsed time and of numbers of actions completed during an exercise period, and pulse rate or other physiological parameters can be measured while exercise is being undertaken, and visible or audible indications thereof provided.

25 Claims, 58 Drawing Figures

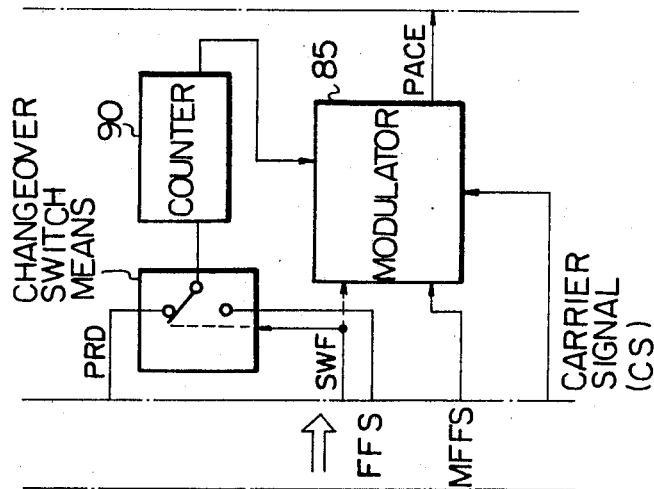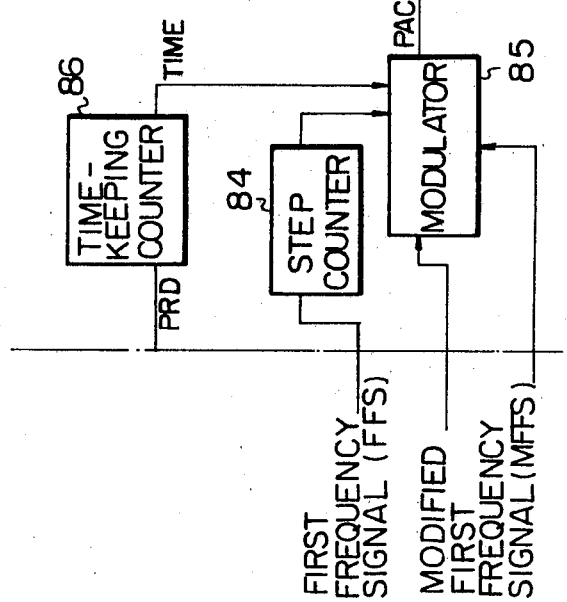

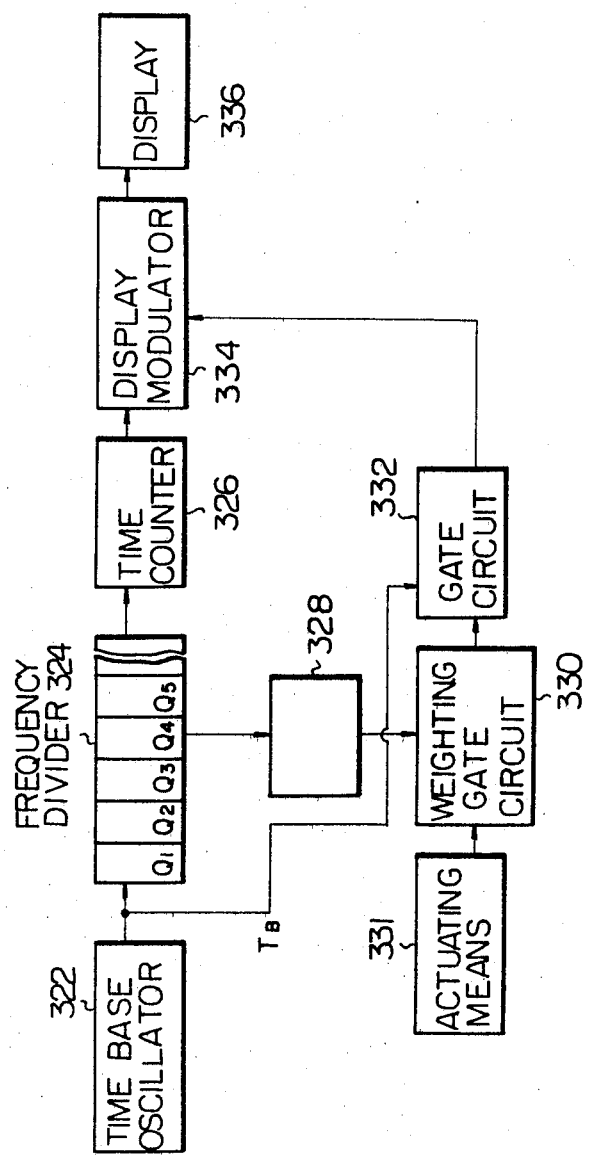

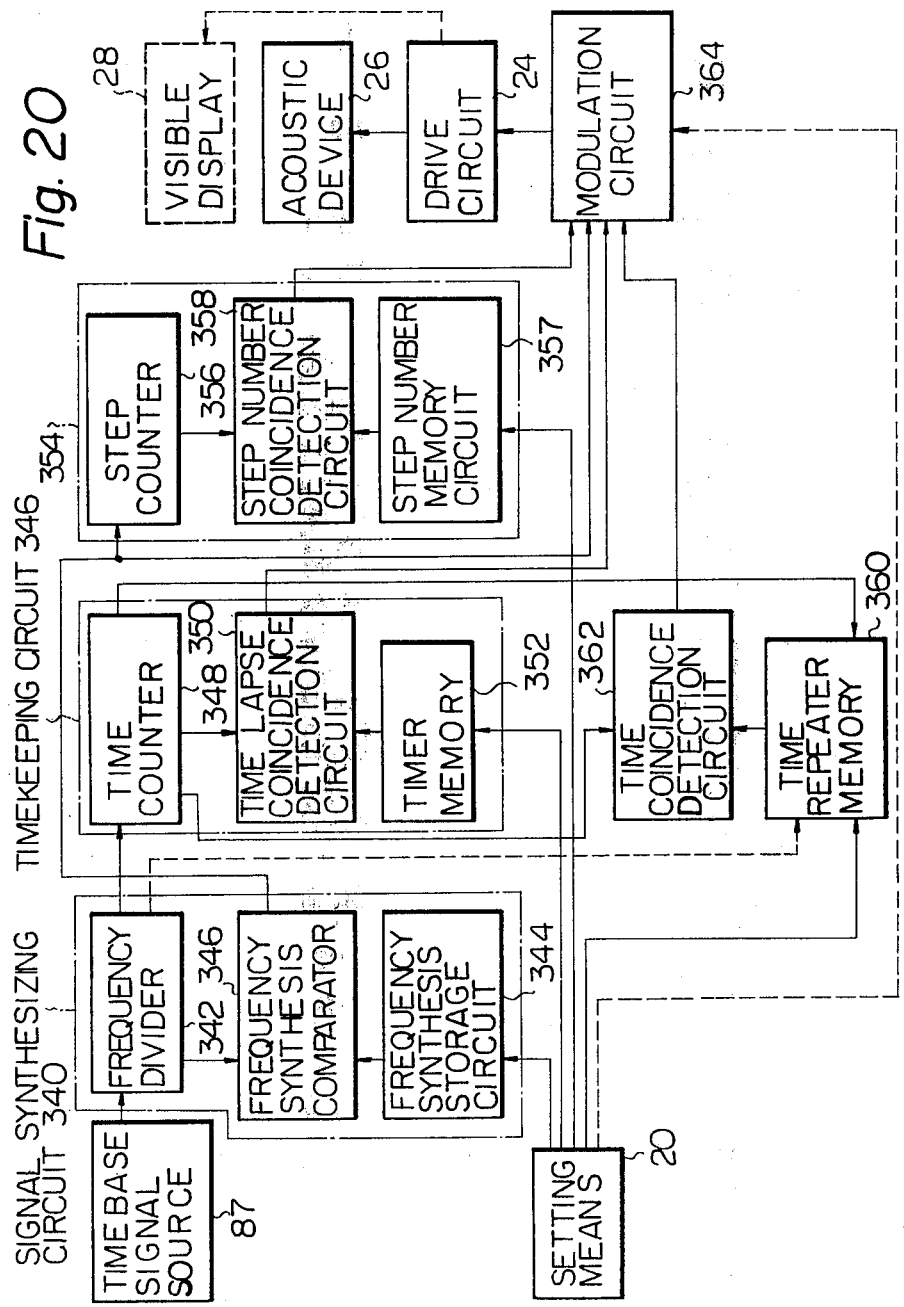

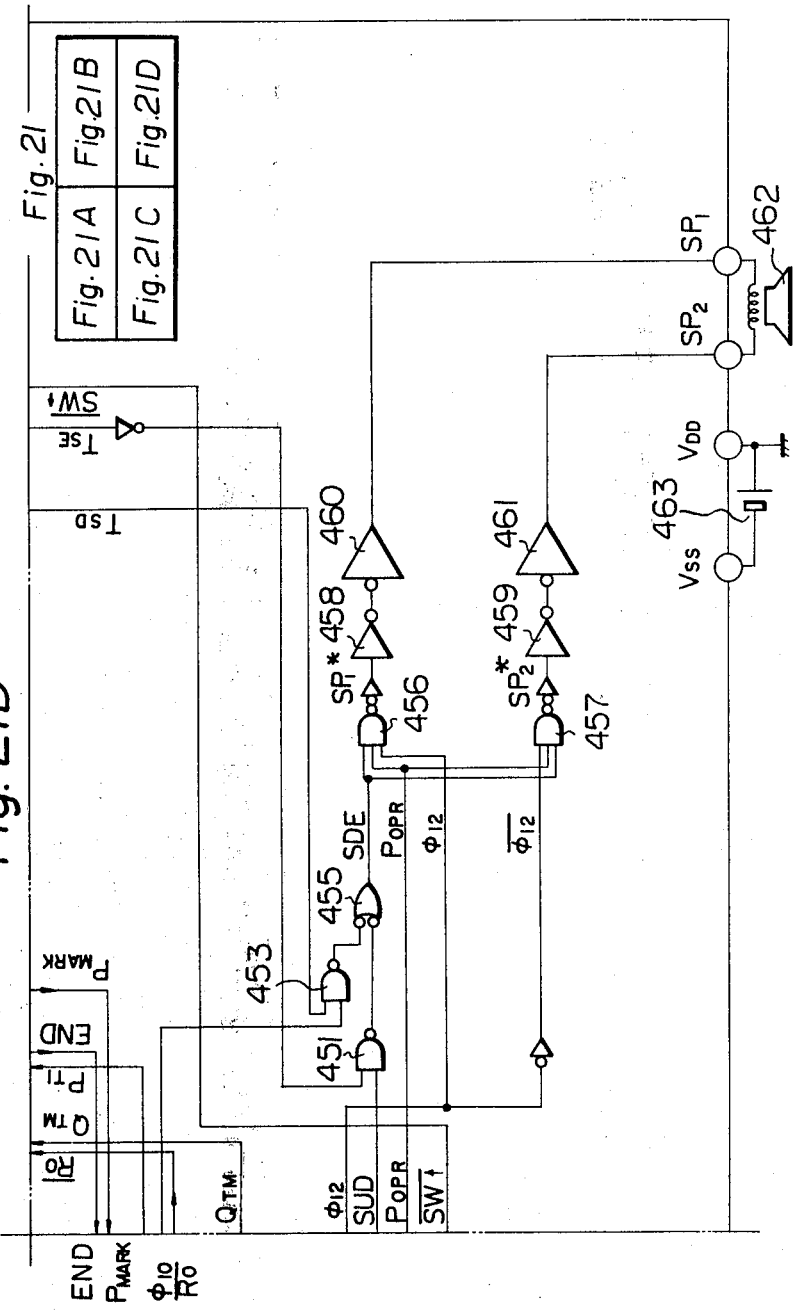

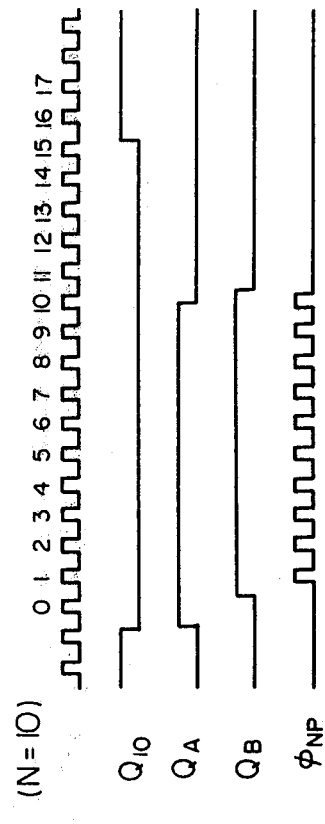
Fig. 22 (N=10)
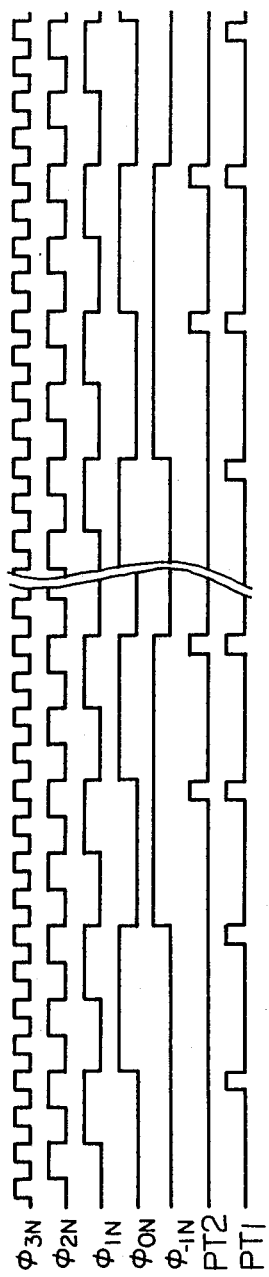
Fig. 23

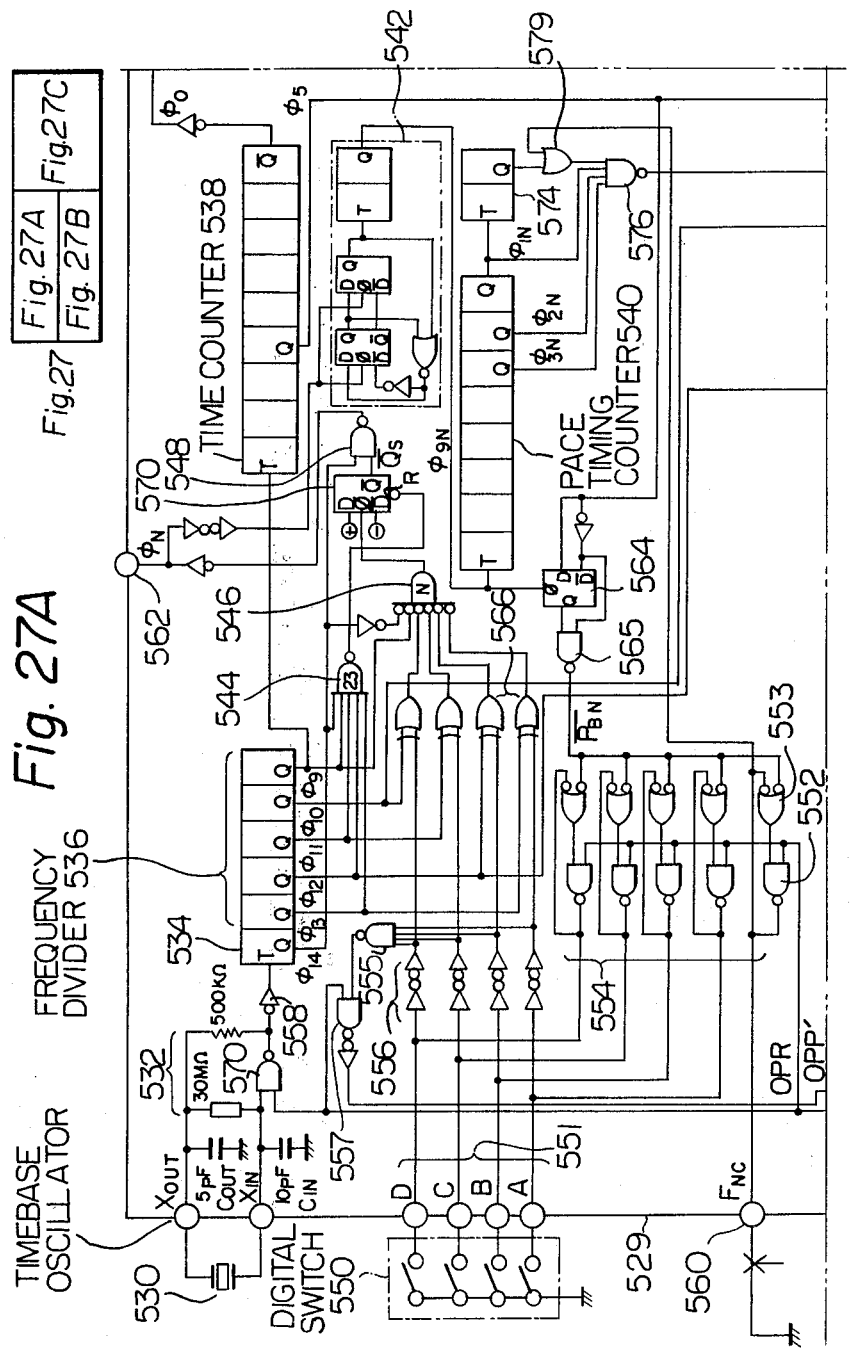

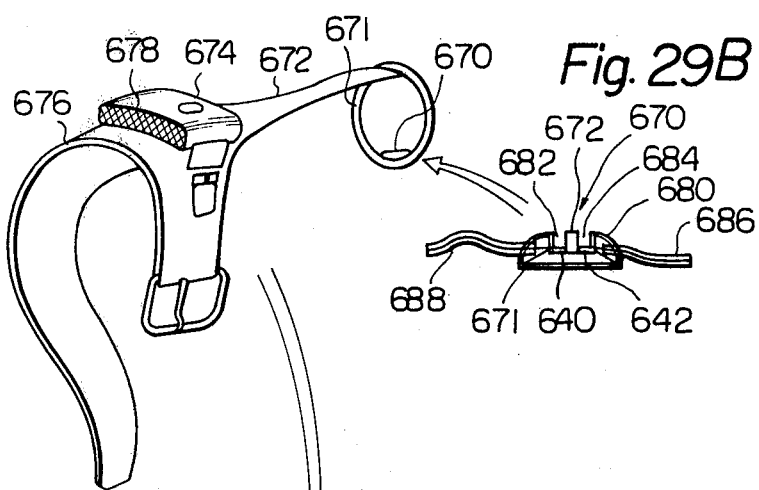
Fig. 29C
Fig. 29B
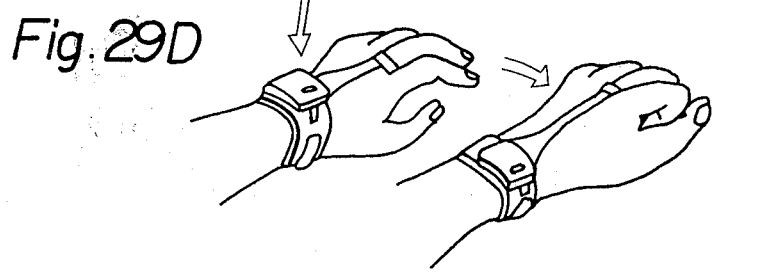
Fig. 29D
Fig. 29E

PACE TIMING DEVICE

The present invention relates to a pace timing device for providing audible timing information to enable steps or actions in physical exercise to be performed at a suitable predetermined rate.

At present, there is widespread interest in the use of regular physical exercise as a means of promoting and maintaining bodily and psychological health. Various medical authorities have recommended such exercise as running and jogging, and these have become extremely popular in various countries. Medical science has also discovered in recent years that even persons suffering from cardiac problems can achieve a measure of improvement of the heart functioning, by undertaking such exercise as jogging, if this is done in a carefully predetermined manner. Excessive levels of exercise, however, can have adverse effects upon the body in some cases, particularly in the case of elderly persons. In the case of cardiac sufferers, of course, an excessive level of physical exertion can have dangerous or even fatal results. An excessive level of exercise can consist of, for example, running or jogging at an unsuitably high rate, or of running at a suitable rate but for an excessive period of time, which can also be considered as running for an excessive distance. It has therefore become very desirable to provide some means whereby a person undertaking exercise, or a physician or other person supervising such exercise, can measure the level of exercise, i.e. the rate at which it is performed and the time or distance over which it is performed. Such means should preferably be completely portable, simple to operate, and should provide clear and unambiguous indications. It is also desirable, particularly in the case of elderly persons or cardiac patients, to provide some means whereby the pulse rate of the person exercising can be measured during or immediately after the completion of the exercise. It is generally recognized that if the pulse rate remains above a certain level following the completion of exercise, this is an indication that the level of exertion is excessively high for that particular individual.

With a pace timing device in accordance with the present invention, an audible signal is generated in a periodic manner, to indicate the predetermined suitable rate of exercise, i.e. the rate at which running steps or other actions should be performed. In addition, an audible indication can be given that a predetermined time period or distance for the exercise has been attained. A pace timing device in accordance with the present invention can also provide an audible indication of a time period following the completion of the exercise during which the pulse rate of the participant can be measured, or can be equipped with an auxiliary detection means whereby the pulse rate, etc. can be directly detected and can be displayed in digital form. A pace timing device according to the present invention can be extremely light and of small size, so as to be worn in the same way as a wristwatch, or can be combined with a digital electronic timepiece such as a wristwatch.

It is therefore an object of the present invention to provide a pace timing device whereby an audible indication is given of a predetermined rate for performing actions of a physical exercise.

It is a further object of the present invention to provide a pace timing device whereby an audible indication is given of a predetermined duration of physical exercise having elapsed.

It is another object of the present invention to provide a pace timing device whereby an audible indication is given of a predetermined number of actions in physical exercise having been performed.

It is another object of the present invention to provide a pace timing device which also functions to provide a display of pulse rate, in digital display form.

Further objects, features and advantages of the present invention may be more clearly understood by referring to the following description and the attached drawings. The scope claimed for this invention is defined by the appended claims.

In the drawings:

FIG. 8A is a block diagram illustrating a method by which output signals from a step counter and a timekeeping counter can be applied to a modulator circuit to modulate a pace signal;

FIG. 8B is a block diagram illustrating a method by which a single counter circuit can be utilized selectively either as a step counter or as a timekeeping counter;

FIG. 14 is a block diagram of a pace timing device employing a frequency synthesizer;

FIG. 20 is a block diagram of an embodiment of a pace setting device having a frequency synthesizer system, a timekeeping counter facility, and a step counting facility;

FIG. 21A, 21B, 21C and 21D are sections of a detailed circuit diagram of an embodiment of a pace timing device according to the present invention;

FIG. 22 and FIG. 23 are waveform diagrams illustrating the operation of the circuit of FIG. 21A to D;

FIG. 27A to 27C are sections of the detailed circuit diagram of another embodiment of a pace timing device, in which a binary switch is used to set a desired pace signal frequency;

FIG. 29B to 29E are drawings illustrating the general configuration of a pace timing device having a pulse rate detection facility;

FIG. 2 is a cross-sectional view of a pace setting device having an externally inserted battery;

Figure 1:
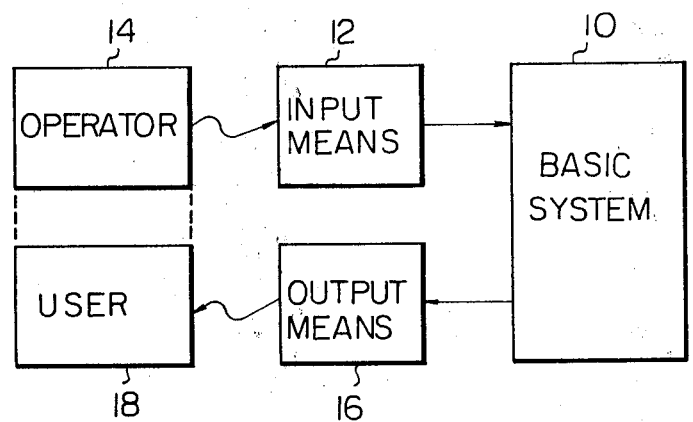
FIG. 1 is a block diagram illustrating the basic principles of the present invention.

Referring now to the drawings, FIG. 1 is a basic block diagram to illustrate the fundamental principles of a pace timing device according to the present invention. Numeral 10 denotes the basic system of the pace timing device, which performs timing, measurement, or other functions. Information for setting various parameters of the system can be entered through some input means 12, by an operator 14. Information which is processed by, or originated by, the basic system 10 is output by some output means 16 to the user of the device 18. Such output can be in the form of audible or visible signals directed to the user. As indicated by the broken lines, the user and the operator can be different, or can be the same person. For example, the operator can be a physician who is supervising physical exercise which is being undertaken by the user 18, or the user 18 can monitor the exercise process by himself. In any case, a closed-loop man-machine system is established. It is essential to ensure that information can flow freely around this loop, in order to ensure ease of use of the device.

Figure 2:
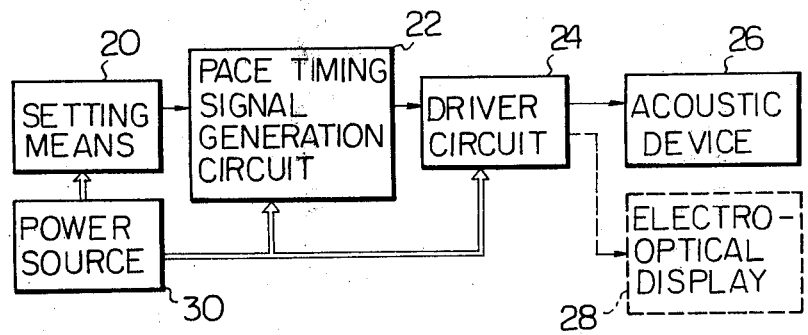
FIG. 2 is a block diagram illustrating the essential sections of a first embodiment of a pace timing device according to the present invention.

Referring now to FIG. 2, a block diagram is shown of the basic features of a first embodiment of a pace timing device according to the present invention. Numeral 20 denotes setting means, whereby an operator can cause a pace signal generation circuit 22 to generate a periodically repeated pace signal at a desired repetition rate. The pace signal will in general comprise repetitive bursts of a square-wave or sinusoidal signal, having frequency components in the audible range. The pace signal is applied to a driver circuit 24, which provides output signals of suitable amplitude for actuating an acoustic device 26, which thereby generates an audible pace timing signal comprising periodic tone bursts. The user can thereby perform actions of a physical exercise, such as running, jogging, etc., at the rate which is specified by the repetitive tone bursts. Numeral 30 denotes a power source, which will normally be a battery, in the case of a portable pace timing device. An opto-electric display device 28 may also be incorporated, in order to provide a visible display of the frequency of pace signal repetition which has been set. Also required, in some cases, is some switch means whereby the power supply of the device can be cut off in order to reduce unnecessary drain of the battery current. Such switch means may be incorporated in the setting means 20. Setting means 20 also serves to perform such functions as starting and stopping operation of the device, enabling and inhibiting audible generation of a pace signal, setting the repetition rate of the pace signals, adjustment of the tone pitch and timbre of the pace signals, and various other functions which will be described hereinafter.

Figure 3:
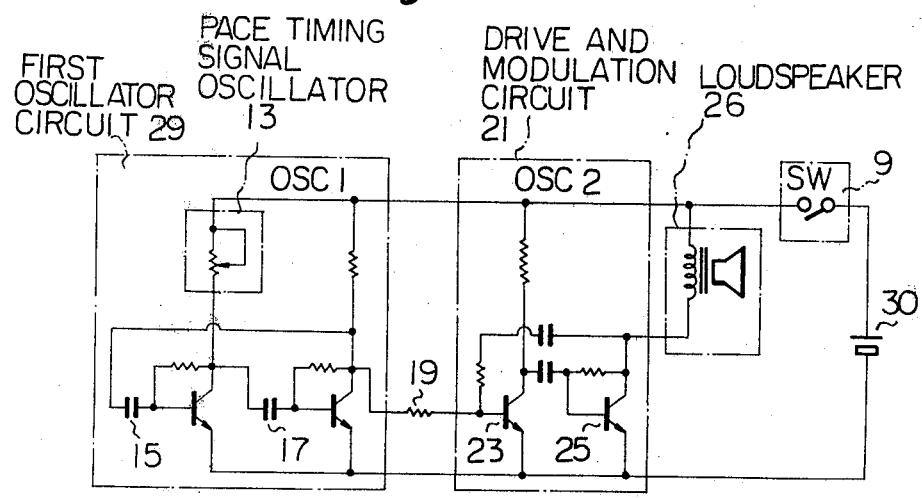
FIG. 3 is a circuit diagram of a simple example of a pace timing device based on the block diagram of FIG. 2.

A specific embodiment of an extremely simple pace setting device according to the present invention, conforming to the block diagram of FIG. 2, is shown in FIG. 3. The embodiment of FIG. 3 utilizes bipolar transistors, and is suitable for either discrete component type construction, or integrated circuit type construction. Numeral 29 denotes a first oscillator circuit, which produces a signal determining the repetition rate of the pace signal. The signal produced by first oscillator circuit 29 will be designated as the first frequency signal. First oscillator circuit 29 comprises a two-stage ring oscillator circuit, and the frequency of oscillation is controlled by means of a variable resistor 13. The first frequency signal is applied through a resistor 19 to the base of a transistor 23 in a second oscillator circuit 21. Power is applied from a battery 30 to the circuit through a switch 8, so that operation can be switched on and off as required. Acoustic device 26 comprises a miniature loudspeaker, which is coupled to the collector of a transistor 25 in second oscillator circuit 21.

The operation of this circuit is as follows. If the voltage applied to resistor 19 from first oscillator circuit 29 is at the low level potential of battery 30 (referred to hereinafter as the L level), then second oscillator circuit 21 oscillates to provide a carrier signal at a relatively high audible frequency, causing an audible tone to be generated by loudspeaker 26. When the voltage applied to resistor 19 from first oscillator circuit 29 is at the high potential of battery 30 (referred to hereinafter as the H level), then a current is passed into the base of transistor 23, causing this transistor to become saturated, thereby inhibiting oscillation by second oscillator circuit 21. Thus, as first oscillator circuit 29 oscillates, operation of second oscillator circuit 21 is periodically enabled and inhibited, so that bursts of tone are generated by miniature loudspeaker 30 with the repetition rate of these tone bursts (i.e. of the pace signal) being determined by the oscillation frequency of first oscillator 29. Registor 19 coupled to the base of transistor 23 thus serves as a means of modulating the signal produced by second oscillator 21 by the first frequency signal produced by first oscillator 29. The frequency of oscillation of first oscillator 29 can be, for example, of the order of 2 to 3 Hz, while that of second oscillator 21 can be of the order of 4 KHz.

A pace timing device of the form shown in FIG. 3 can be manufactured at very low cost. Discrete components can be utilized throughout if desired. It is also possible to provide all components other than variable resistor 13, loudspeaker 30 and capacitors 15 and 17 of first oscillator 29, on an integrated circuit. Due the the low frequency of operation of first oscillator 29, capacitors 15 and 17 would be too high in value to be accommodated on an integrated circuit chip. However, it is possible to utilize an oscillator circuit of relatively high frequency for first oscillator circuit 29, followed by several stages of frequency division, to provide a suitably low frequency for the first frequency signal. If this is done, then a pace timing device of very low cost can be provided, in whichh all circuitry is integrated.

A disadvantage of the arrangement shown in FIG. 3 is that the frequency of oscillation of first oscillator circuit 29 varies with changes in supply voltage and in operating temperature, due to changes in the base-emitter forward voltage ($V_{be}$) of the transistors with temperature. A suitable stabilized power supply for overcoming this problem will be described hereinafter.

With the embodiment of FIG. 3, information concerning the pace signal repetition frequency can be fed back to the operator or user by means of a graduated dial coupled to variable resistor 13, suitably calibrated to indicate the pace frequency.

Figure 4:
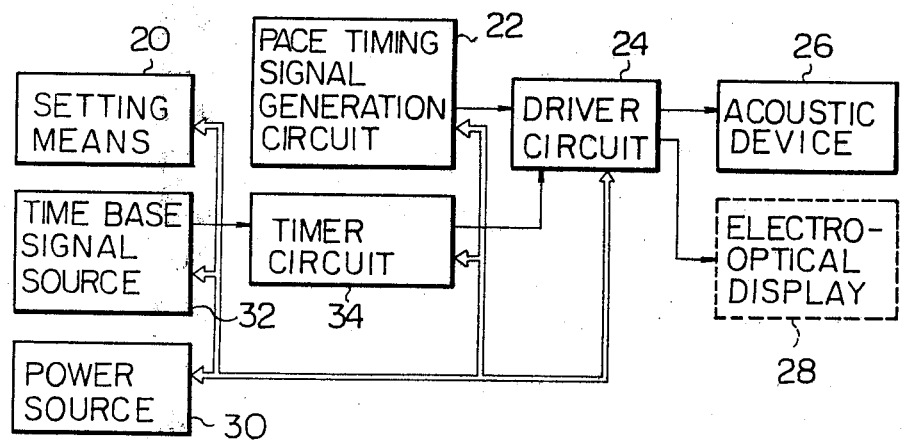
FIG. 4 is a block diagram of a second embodiment of the present invention, which further comprises a timer facility.

Referring now to FIG. 4, a second embodiment of a pace setting device is shown, in basic block diagram form. This is similar to the system of FIG. 2, but also incorporates a timer facility. When performing exercise in accordance with a predetermined program, it is important that the duration of the exercise should be precisely determined, as well as the rate at which the exercise is performed. It is therefore desirable to provide some means whereby an indication is given of the completion of a predetermined time interval following the start of operation of the pace timing device (i.e. after audible pace timing signals begin to be emitted). In FIG. 4, numeral 32 denotes a timebase signal source which produces a timebase signal of fixed frequency, applied to a timer circuit 34. Timer circuit 34 can comprise a counter circuit, which produces a time marker signal when a predetermined number of pulses of the timebase signal have been counted, after an initial reset condition of timer 34 is released. The time marker signal is applied to driver 24, to cause an audible time marker indication to be given by acoustic device 26, that the predetermined time interval has elapsed. This time marker indication can be given, for example, by causing a tone burst of different frequency or timbre from the pace timing signal to be emitted by acoustic device 26.

In the diagram of FIG. 4, the timer 34 is shown as being supplied with a timebase signal from timebase signal source 32. However, if an extreme degree of accuracy is not essential, it is also possible to utilize some other type of timer arrangement, such as a timer using the rate of charging of a capacitor, for example.

As in the case of FIG. 2, a visible display of pace timing information can be provided by an optional optoelectronic display 28, which can consist of a liquid crystal display, for example.

Figure 5:
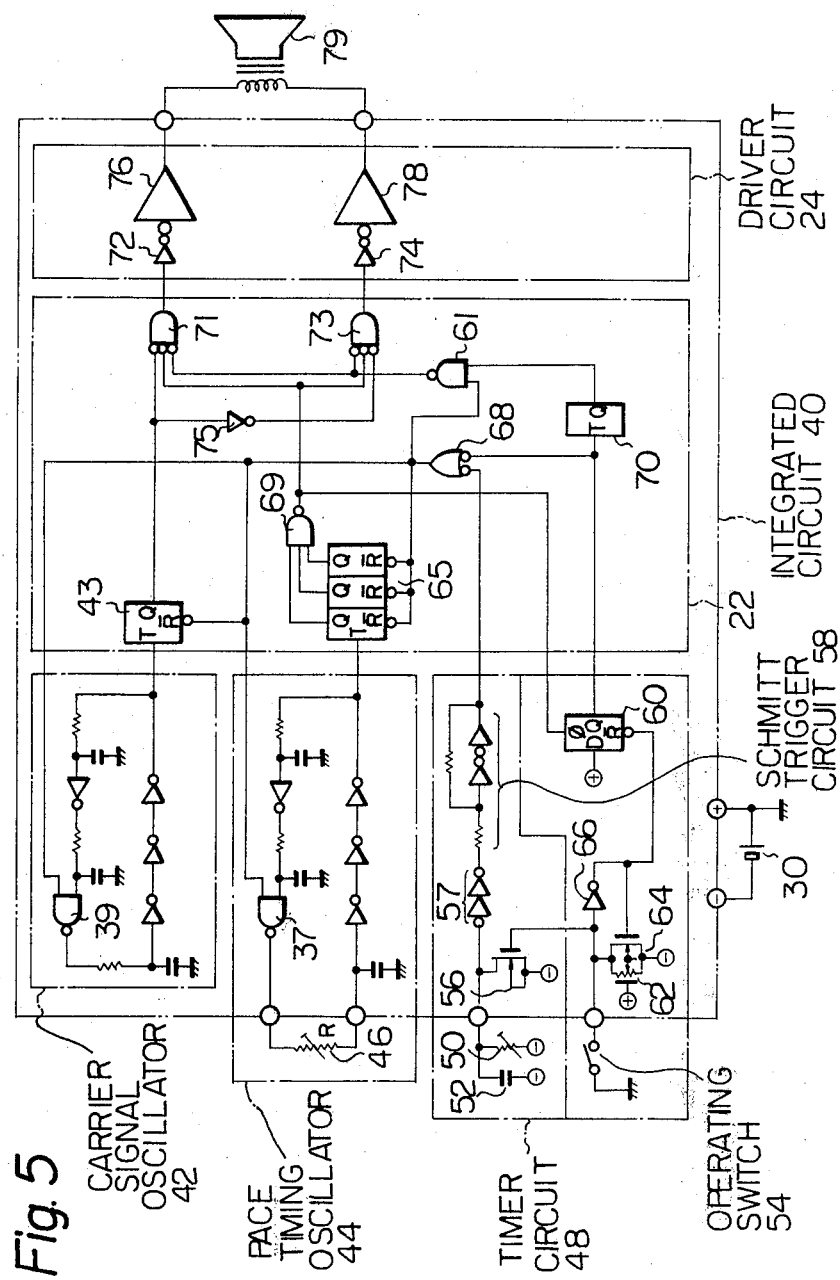
FIG. 5 is a circuit diagram of a simple example of a pace timing device based on the block diagram of FIG. 4.

A simple embodiment of a pace timing device, which is basically in accordance with the block diagram of FIG. 4, is shown in FIG. 5. In this embodiment, a timer circuit is used which is based upon the rate of charging of a capacitor, rather than upon a counter circuit supplied with a timebase signal. It should be noted that, as is customary in electronic timepiece design, the high potential (i.e. the positive terminal) of the device battery is connected to ground. Thus, the ground potential will be referred to in this description as the H level, and the ground potential symbol in the figures indicates the same potential as the $\oplus$ symbol. Numeral 44 denotes a first oscillator circuit, comprising a ring oscillator of variable frequency. The frequency of oscillation of oscillator 44 is controlled by a variable resistor 46, and its output signal is applied to three-stage frequency divider 65. The outputs of frequency divider 65 are applied to inputs of a NAND gate 69, so that the output of NAND gate 69 goes to the L level for the duration of one period of the output signal from first oscillator 44, once in every 8 periods of first oscillator 44. A first frequency signal of low duty cycle is thereby produced by NAND gate 69. Numeral 42 denotes a second oscillator circuit, for producing a carrier signal, which is also of ring oscillator configuration. The frequency of the carrier signal of second oscillator circuit 42 is of the order of 8000 Hz. The output signal from second oscillator 42 is applied to a T-type flip-flop 43, which serves as a single stage of frequency division, and the output from frequency divider flip-flop 43 is applied to an input of a gate 71, and through an inverter 75 to an input of another gate 73. The first frequency signal from NAND gate 69 is also applied to inputs of gates 71 and 73, as is the output of a NAND gate 61. While the output of NAND gate 61 is at the H level, and both first oscillator 44 and second oscillator 42 are in operation, bursts of tone at the frequency of the output from flip-flop 43 and at the repetition rate of the first frequency signal from NAND gate 69 are alternately output from gates 71 and 73. These output signals from gates 71 and 73 are applied to inputs of inverters 72 and 74, the outputs of which are applied to inputs of driver inverters 76 and 78 respectively. The output signals from driver inverters 76 and 78 are applied to the coil of a miniature electromagnetic loudspeaker 79, which is thereby driven in push-pull fashion.

Numeral 54 denotes an externally actuated switch, which is used to start and stop operation of the circuit. Switch 54 is coupled to an input terminal 49, which is held at the L potential (so long as switch 54 is not actuated) by being connected to the L level potential through a resistance of very high value 62. This resistance can consist of a diffusion resistor, or of an N-channel field effect transistor. Resistor 62 is connected between the drain and source of a locking transistor 64, which is an N-channel field effect transistor, the gate of which is connected to the output of an inerter 66, and the gate of which is connected to the input of inverter 66 and to terminal 49. So long as switch 54 is not actuated, i.e. is in the open condition, the input of inverter 66 is connected to the L level potential through resistor 62, so that an H level input is applied to the gate of N-channel transistor 64 from inverter 66 output. Transistor 64 is therefore held in the conducting condition, so that a low impedance path is established through transistor 64 between input terminal 49 and the L potential side of the battery. Such a low impedance condition of an input terminal is essential to ensure reliable operation of a circuit using field effect transistors, which are extremely susceptible to damage from static electric potentials, or to pickup of noise from external sources, due to the very high input impjedance which such transistors present. With an input arrangment such as that described above, no current is drawn from the battery by the circuitry for maintaining input terminal 49 at a low impedance state, both when switch 49 is not actuated and when it is actuated.

When switch 49 is actuated, then an H level input is applied to inverter 66 so that its output goes to the L level, thereby causing N-channel transistor 64 to go to the high impedance state, so that no current flows through transistor 64. The output of inverter 66 is also connected to the inverting reset input of a data-type flip-flop 60, the data input terminal of which is connected to the H level. The clock input terminal of flip-flop 60 is connected to the output of NAND gate 69, and the Q output terminal is connected to the T terminal of a toggle-type flip-flop 70. The Q output of flip-flop 70 is connected to an input of NAND gate 61, the other input of which is connected to the output of gate 68.

Numeral 48 denotes a timer circuit, incorporating a timing capacitor 52 and a variable resistor 50, which can be preset so as to provide a desired rate of charging of timing capacitor 52, from the H level potential. Numeral 56 denotes an electronic switch, comprising an N-channel transistor having its gate connected to the input terminal 49 and its source and drain terminals connected to the junction of timing capacitor 52 and variable resistor 50 and to the L level potential, respectively. The junction of timing capacitor 52 and resistor 50 is also connected through a pair of buffer inverters 57 to the input of a Schmitt trigger circuit 58, the output of which is connected to an input of gate 68.

The operation of the circuit of FIG. 5 will now be described. In the non-operating state, timing capacitor 50 is charged to the H level potential, through variable resistor 50. The output of inverters 57, and hence the output of Schmitt trigger circuit 58, is therefore at the H level. The Q output of flip-flop 60 is also at the H level, so that the output of gate 68 is at the L level. Both of NAND gates 37 and 39 in oscillator circuits 46 and 42 respectively are thereby inhibited, so that oscillation does not occur. An L level potential is applied to the gate of transistor 56, so that no current is drawn by this transistor, and the same is true of transistor 64, since the drain and source terminals are at the same potential, i.e the L level. In this state, only a very small level of current is drawn from the device battery 30, due to the use of complementary field effect transistor circuitry. An on/off switch is therefore not absolutely necessary. When now switch 54 is actuated, then the gate of transistor 56 does to the H level, causing this transistor to enter the conducting state. Timing capacitor 52 is thereby rapidly discharged, so that the output of Schmitt trigger circuit 58 switches to the L level. The output of gate 68 accordingly goes to the H level, thereby enabling NAND gates 37 and 39 of oscillator circuit 44 and 42, so that these circuits begin to oscillate. It should be noted that all of the flip-flop circuit described in this embodiment, (and in subsequently described embodiments of the present invention) are of negative edge triggered type, i.e. the Q output of a flip-flop changes state upon the negative-going edge of a clock signal applied to a clock input terminal or a toggle (T) input terminal. After 7 pulses have been generated by first oscillator circuit 44, therefore, the output of NAND gate 69 goes from the H level to the L level, and this transition causes the output of data-type flip-flop 60 to go to the H level. This is necessary due to the fact that, when switch 54 is actuated, the output of inverter 66 goes to the L level, thereby resetting flip-flop 60 and so causing an H level-to-L level transition to occur at the T terminal of toggle-type flip-flop 70. The state of the Q output of flip-flop 70 can therefore be changed from the H level to the L level, and vice-versa, by successive actuations of switch 49. Between successive actuations. flip-flop 60 is set by the output from NAND gate 69. When the output of flip-flop 70 is at the L level, then the output of NAND gate 61 is at the H level so that gates 71 and 73 are inhibited. Thus, it is possible for the user to interrupt generation of the audible pace timing signals, before the time interval set by timer circuit 48 has elapsed, simply be actuating switch 49 once.

If we assume that switch 49 has been actuated and that the Q output of flip-flop 70 is at the H level, then a pace signal will be applied to inverters 72 and 73 of driver circuit 24, causing an audible pace timing signal to be generated by loudspeaker 79. When the potential across capacitor 52 rises to a predetermined value, due to charging through variable resistor 50, then this is detected by Schmitt trigger circuit 58, the output of which then goes to the H level. At this time, the output of flip-flop 60 is also at the H level, as described previously, so that the output of gate 68 goes to the L level. Frequency divider 65 is therefore placed in the reset state, and NAND gates 37 and 39 are inhibited, so that operation of oscillator circuits 42 and 46 is halted. The use of Schmitt trigger circuit 58 in detecting the rise of the voltage across timing capacitor 52 to the predetermined value serves to provide greater accuracy and reliability of detection, due to the hystersis of the Schmitt circuit, since the possibility of spurious detection of the end of the predetermined time interval is reduced.

All of the circuitry of the pace timing device of FIG. 5 is contained upon a single monolithic integrated circuit, other than pace timing setting resistor 46, switch 54, timing capacitor 52 and variable resistor 50, the loudspeaker 79. Each of driver inverters 76 and 78 consists of a large sized complementary field effect transistor, such as a transistor of insulated gate construction, which has an output resistance of the order of several tens of ohms in the conducting state. Such transistors have a high level of gate input capacity, so that it is necessary to use driver input inverters 72 and 74 in order to ensure that the waveforms of the drive signals applied to drive inverters 76 and 78 have low rise and fall times. If the rise and fall times of the drive signals applied to drive inverters 76 and 78 are excessively long, then a high level of current will be drawn by these transistors, due to the complementary field effect transistor configuration.

To operate the device, the user first adjusts variable resistor 46 to a suitable setting to provide the desired repetition rate of pace signal. A graduated dial may be provided for this purpose. Switch 49 is then actuated, whereupon the audible pace timing signal "pi, pi, pi, . . ." will be heard. This signal consists of tone bursts with a duty cycle of ⅓, due to the action of divider circuit 65. At the end of a predetermined time interval, which is determined by the capacity and rate of charging of capacitor 52, the operation of the device is terminated by timer circuit 48. At any point prior to the lapse of this time the user in interrupt the generation of the audible pace timing signal simply by actuating switch 54.

Although the circuit of FIG. 5 utilizes a timing capacitor and charging means in the timing circuit 48, it is also possible to provide a source of a timebase signal and a counter circuit to count the timebase signal, in order to perform the function of timing circuit 48.

Figure 6:
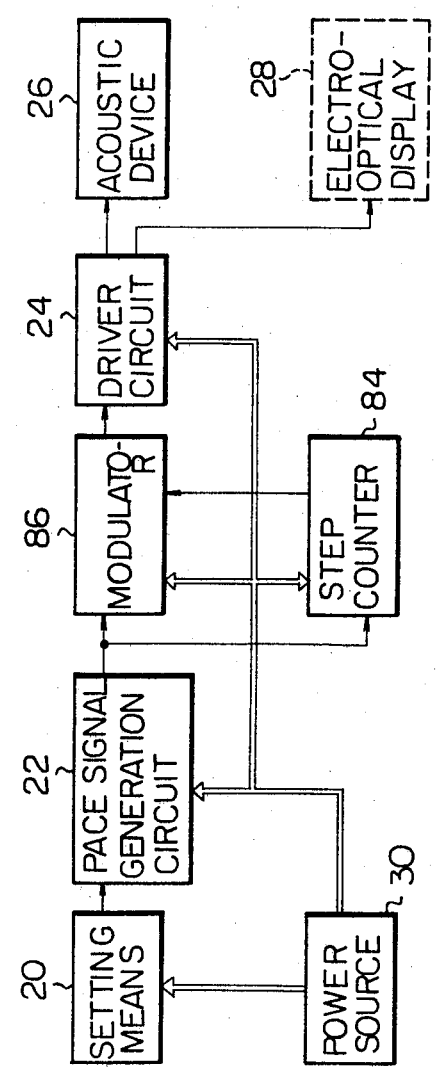
FIG. 6 is a block diagram of a third embodiment of the present invention which incorporates a facility for counting and indicating a number of steps in a physical exercise.

Referring now to FIG. 6, a block diagram is shown of an embodiment of the present invention which provides an audible indication that a predetermined number of steps or other bodily actions of an exercise have been completed. It should be noted that, in this embodiment, the number of steps may not correspond to the number of tone bursts of the audible pace timing signal. This is because a capability for introducing a regular rythm into the pace signal is provided in the embodiment of FIG. 6. A regularly and continuously repeated pace timing signal tends to have a monotonous effect, which can be irritating to the user. It is therefore possible to arrange that alternate tone burst groups are omitted from the audible pace timing signal. For example, if we denote a single tone burst of a pace signal by the musical symbol ♩, then a pace signal having a rythm component which is produced by regularly recurring pauses can be denoted as "♩♩𝄽♩♩𝄽" where symbol 𝄽 indicates a rest, in musical notation, and indicates the omission of a tone burst in the audible pace timing signal in the present case. In this way, a pace signal having a pleasant and stimulating rhythm is provided, which tends to make use of the pace timing device more easy and natural. However in this case, the actual number of steps will be double the number of tone bursts of the audible pace timing signal.

In FIG. 6, the pulses of a first frequency signal, which determine the actual pace frequency, i.e. the repetition rate of the audible pace timing signal including any omissions as described above, are applied to a modulator circuit 86 and to a step counter circuit 84. The modulator circuit 86 serves to modulate a signal of relatively high audio frequency, with the first frequency signal, to produce the pace signal. It also serves to introduce the rhythm component (if required) by omitting regularly recurring groups of tone bursts of the pace signal. The step counter 84 may be a decimal counter, and applies a step count signal to the modulator circuit upon the completion of a predetermined number of steps, thereby causing the modulator circuit to produce a modulated step count signal, which differs in carrier frequency, duration or haromnic components from the pace signal. after each 100 steps have been completed, the step counter signal can cause the modulator to produce a tone burst which is of different timbre, pitch or duration than those of the normal pace signal, so as to notify the user. Similarly, when 1000 steps have been completed, a tone burst of different characteristics can be generated. An alternative method of indicating that 1000 steps, or a multiple thereof, has been completed, is to use a principle which was formerly employed in some timepieces to indicate time information in an audible manner. With such a timepiece, which in the case of a watch was called a "repeater" watch, a single note is sounded to indicate one o-clock, two consecutive notes are sounded to indicate 2 o-clock, and so on. In the following description of the present and subsequent embodiments of the present invention, such a facility for indicating information in an audible manner will be referred to as a "repeater" facility, for brevity of description. If such a repeater facility is used to indicate; for example, a count of steps in the embodiment of FIG. 6, then a single tone burst of particular frequency and duration can be generated by means of modulator circuit 86 in response to an output signal from step counter 84 after 1000 steps have been counted, two immediately consecutive tone bursts of the same frequency and duration generated after 2000 steps have been counted, three tone bursts when 3000 steps have been counted, and so on. It is also possible to arrange that, rather than these tone burst (which will be referred to as repeater signals) being generated automatically, the user can actuate a switch and thereby command that a repeater signal be produced to indicate the approximate number of steps which have been completed, to the nearest 1000 steps, for example. It is also possible to measure distance travelled (in the case of running, jogging etc.) rather than the number of steps completed. This is done by multiplying the number of steps completed by the length of pace of the user. For example, if the user has a length of pace of 80 cm, and the number of steps completed is 125, this corresponds to a distance of 100 meters travelled. The distance travelled can be indicated audibly, in a similar manner to that described for the number of steps, by modulation of tone frequency or duration, and by use of a repeater facility.

Figure 7:
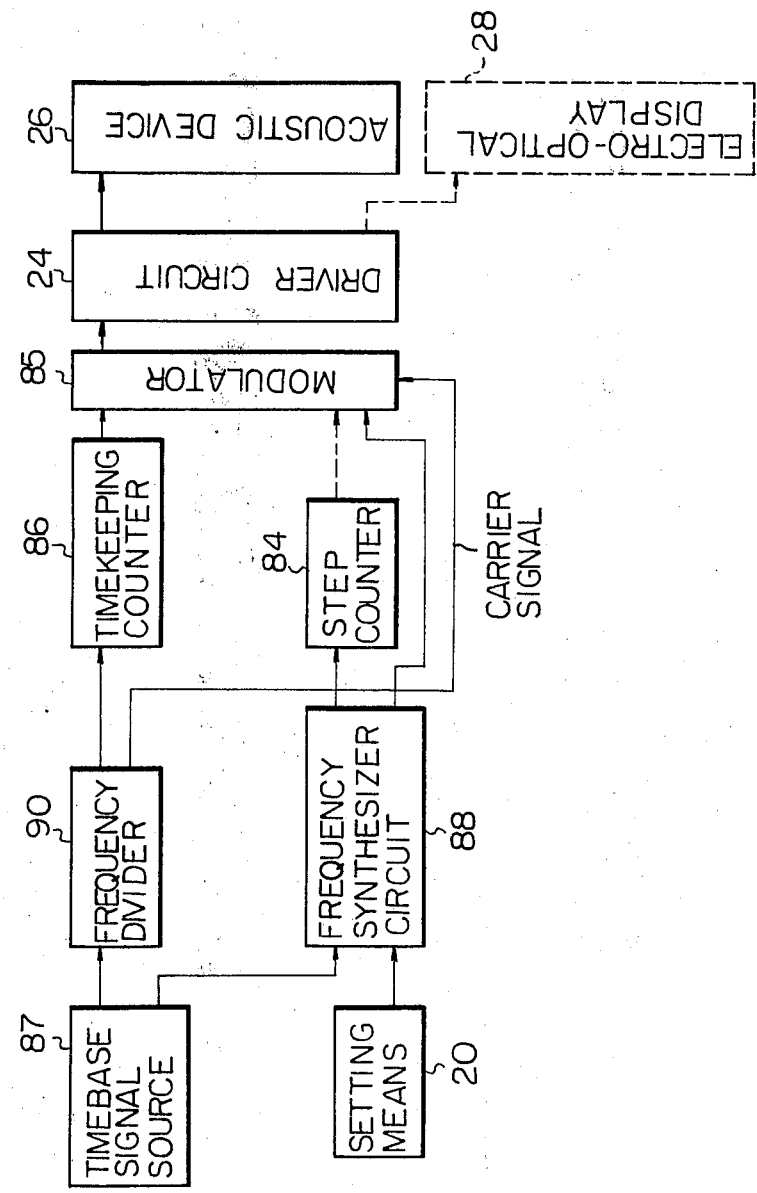
FIG. 7 is a block diagram of a fourth embodiment of the present invention, which incorporates both a facility for counting and indicating a number of steps and also a facility for counting and indicating elapsed time.

Numeral 28 in FIG. 7 indicates a visible display facility, such as an electro-optical display. This may be provided as an optional feature, to display, for example, the number of steps which have been executed or the total distance which has been covered. The information can be displayed in digital form, or in analog form such as a bar graph. It is possible to combine a pace timing device such as that of FIG. 6 with a digital electronic timepiece. In this case, the digital display portion of the timepiece which is normally used to display the date, etc., in digital form, can be used to display the number of steps executed, or the total distance travelled (in meters or yards, for example) when the device is in a pace timing mode of operation.

It should be noted that it is not necessary to reset the number of steps, or distance travelled, to zero each time the device has been used. The total number of steps, or distance, can be integrated over a number of exercise periods, to thereby provide the user with information on the total amount of exercise performed over a relatively long time span. The user can thereby be encouraged to proceed with the exercise program.

The embodiment of FIG. 6 can also be provided with some timer means, such as that of FIG. 4, whereby operation of the device is automatically, halted after a predetermined time period has elapsed.

Referring now to FIG. 7, an embodiment of the present invention is shown in block diagram form which incorporates a time lapse indication facility, in addition to the function provided by the embodiment of FIG. 6 described above. In the embodiment of FIG. 4, a timer facility is provided whereby the operation of the pace timing device is halted after a predetermined time period has elapsed following the start of operation. Since the generation of audible pace timing signals is thereby halted, such a facility can be used to notify the user that a particular duration of exercise has elapsed. Alternatively, such a timer facility can simply serve to ensure that unnecessary battery drain will not be caused by the device being left in the operating state inadvertently. With the timer facility provided in the embodiment of FIG. 7, however, an audible indication is given to the user when each of a series of time intervals of predetermined length has elapsed. This indication can be provided by generating a tone burst of different characteristics from the pace timing signal (i.e. different in pitch, timbre, or duration) when each of the predetermined time intervals has elapsed. The elapsed time indications can also be given by means of a repeater facility, as described above with respect to the indication of step numbers. Thus, a tone burst of particular frequency and duration can be generated after five minutes of exercise have elapsed, two of these tone bursts after 10 minutes have elapsed, 3 tone bursts after 15 minutes have elapsed, and so on.

In FIG. 7, numeral 87 denotes a timebase signal source, which produces a timepiece signal of fixed frequency, of relatively high frequency. Such a timbase signal source is necessary in order to measure the successive time intervals with sufficient accuracy. The output signal from the timebase signal source is applied to a frequency divider 90, which divides the frequency of the timebase signal to a suitable level for input to a timekeeping counter circuit 86. When each of the predetermined time intervals has elapsed, an output signal is produced by timekeeping counter 86, and is applied to a modulator circuit 85. Numeral 88 denotes a frequency synthesizer circuit, which receives a timebase signal from a signal source 87 and also receives control signals from setting means 20. Frequency synthesizer circuit 88 produces a first frequency signal, which is applied to a step counter circuit 85. As in the previously described embodiments of the present invention, the first frequency signal comprises a train of pulses whose repetition rate determines the frequency at which steps or actions are to be performed. The number of actions is therefore counted by step counter 84. The frequency of this first frequency signal is determined by a control input to the frequency synthesizer circuit 88 from setting means 20. Frequency synthesizer 88 also produces a signal, which will be designated hereinafter as the modified first frequency signal. By means of a control signal applied to frequency synthesizer circuit 88 from control means 20, the modified first frequency signal can be made either identical to the first frequency signal, or can have alternate groups of pulses suppressed in order to provide a rythm component, as described previously. The modified first frequency signal is applied to modulator circuit 85, together with a carrier signal, at a relatively high audio frequency provided from frequency divider 90. A pace signal is thereby produced by modulator circuit 85, consisting of tone bursts at the repetition rate of the modified first frequency signal, which are applied through a driver circuit 24 to an acoustic device 26. Audible pace timing signals are thereby generated, with or without a rythm component, as selected by the user.

An output signal from frequency divider 90 is also applied to a timekeeping counter circuit 86, which produces a time marker signal each time a predetermined time interval has elapsed. This time marker signal is applied to modulator circuit 85, and causes a timing signal, modulated at the carrier frequency, to be produced by modulator circuit 85 and applied through drive circuit 24 to acoustic device 26. An audible indication is thereby given of the lapses of time.

As described previously, a repeater facility can be provided with either time counter 86 or step counter 84, or with both of them. In this way the user can be notified of each lapse of a predetermined time period and also of the total time which has elapsed, and of the execution of a predetermined number of steps, and also of the total number of steps which have been executed, without the necessity for a visual indication of such information.

Numeral 28 indicates a visual display means, which can be incorporated in order to display time information in digital form, and information on the number of steps executed (or distance travelled) in digital or analog form. This embodiment may also be combined with an electronic digital timepiece.

It is recommended by some medical authorities that the degree of exertion which is involved in exercise by a particular individual should be checked by means of measuring the pulse rate after a specific period of exercise at a predetermined rate. With the embodiment of FIG. 7, this can be done by causing a special marker note to be emitted after a predetermined duration of exercise has elapsed, for example, 8 minutes or 10 minutes, to notify the user to stop exercising and to begin measuring his pulse rate. After one minute has passed, another marker note can be generated to notify the user to stop counting. In this way, the pulse rate after exercise can conveniently be measured.

Part of the block diagram of FIG. 7 is shown in FIG. 8A. FIG. 8B shows how this embodiment can be modified so that a single counter 90 serves the functions of both the timekeeping counter 86 and step counter 84. As shown in FIG. 8B, either the output from frequency divider circuit 90, designated as PRD, or the first frequency signal from frequency synthesizer circuit 88 can be selectively applied to counteer 90, by means of changeover switch 92, so that either time intervals or numbers of steps are measured by counter 90. It should be understood that, although switch 92 is indicated as a simple changeover switch, it will generally be necessary to provide a more complex switching arrangement, due to the different requirements for the carry function of a timekeeping counter and of a step counter. Changeover switch 92 is controlled by a switching signal SWF produced from setting means 20 under the user's control. As indicated by the broken line, the SWF signal can also be applied to modulator 85, in order to provide different types of audible indication of time count information and step count information respectively. In FIG. 8B, the first frequency signal and the modified first frequency signal are denoted by the letters FFS and MFFS respectively.

Figure 9:
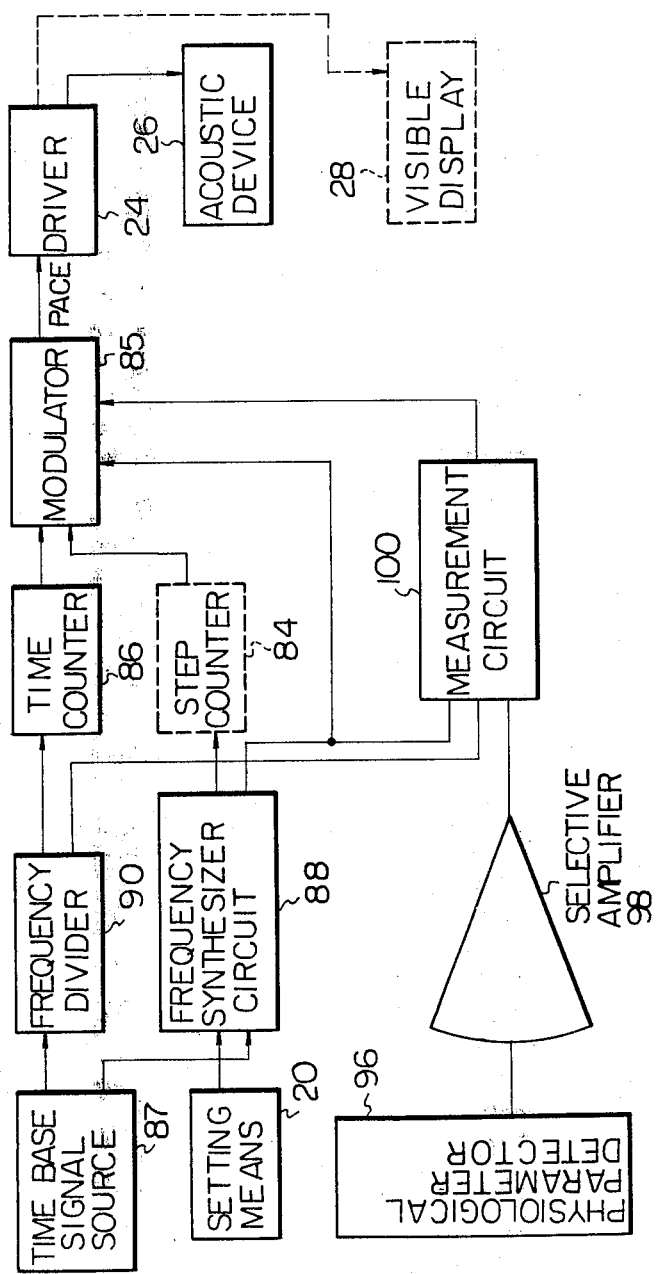
FIG. 9 is a block diagram of a fifth embodiment of the present invention, which incorporates a facility for detecting and measuring a physiological parameter, in addition to facilities for timekeeping and for counting and indicating a step count.

Referring now to FIG. 9, a further embodiment is shown, which incorporates means for detecting one or more physiological parameters of the user while exercise is in progress. In some cases, and particularly in the case of elderly persons or cardiac patients, it is desirable to monitor such physiological parameters as the pulse rate, blood pressure, body temperature, etc., in order to ensure that safe limits for these parameters are not exceeded. With the embodiment of the present invention of FIG. 9, one or more of such parameters can be monitored by a detector 96. The detected information may then by applified by an amplifier 98, which is generally a narrow-band selective amplifier, and the amplifier output is applied to a measurement circuit 100. Measurement circuit 100 can include counter circuits, in the case of pulse rate measurement, voltage comparators for measuring blood pressure or temperature with respect to reference voltages, etc. Output signals from measurement circuit 100 are applied to modulator circuit 85, so that audible warning indications can be given when some limt value for a physiological paremeter is exceeded. The user is thereby warned to terminate the exercise, or to reduce the pace of the exercise. It is possible to modify the embodiment of FIG. 9 such that the frequency of the pace signal is controlled by output signals from measurement circuit 100. For example, if the user's pulse rate should exceed a predetermined level, then the pace frequency can be lowered. It is also possible to arrange that a readout of physiological parameter information is provided by visible display device 28, in digital or analog display form.

In the embodiments of the present invention described herein, the audible information which is provided can modulated in three different ways. To modulate by a rythm, the signal which determines the repetition rate of steps or other actions, which is referred to as the first frequency signal, can be modulated by a signal of lower frequency. In this way, suppression of one or more of the tone bursts of the audible information is performed in a regular, recurring manner. A second mode of modulatin is by pitch. In this case, the frequency of the carrier signal, which is modulated to provide the tone bursts, is varied. For example, the carrier frequency can be changed from 4096 Hz to 3072 Hz. A third mode of modulation is by timbre. In this case, the high order harmonics of the carrier signal are modified. This can be accomplished by modulating the carrier signal with a signal of higher frequency. However, if the modulating signal is non-sinusoidal, then the same object can be achieved by modulating the carrier signal by a signal of lower frequency. This is because the carrier signal will be modulated by the harmonics components of the modulating signal, so that a change in the timbre of the modulated audible signal produced can be achieved. For example, a carrier signal of 4096 Hz frequency can be modulated by a square wave signal of 1024 Hz frequency. The resultant change in the tonal characteristics of the audible signal produced is clear and distinctive.

Figure 10A:
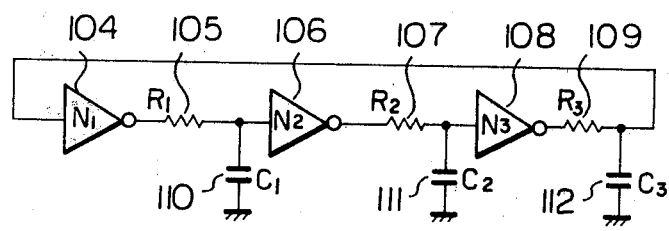
FIG. 10A is a circuit diagram of a ring oscillator circuit suitable for use in a pace timing device according to the present invention.

A description will now be given of ring oscillator circuits which are suitable for regenerating fixed or variable frequency signals in a pace timing device according to the present invention. Referring first to FIG. 10A, numerals 104, 106, and 108 denote inverters, each of which has an amplification factor of greater than unity, and which is negative in sign. Resistors 105, 107 and 109 are coupled between inverters 104 and 106, 106 and 108, and 108 and 104 respectively. Capacitors 110, 111 and 112 are connected between the inputs of inveerters 106, 108 and 104 respectively. The operation of the circuit of FIG. 10A will now be analyzed, on the assumption that the output resistance of each invertr is included in the corresponding resistor connected to the output thereof, and that the input capacitance of each inverter is included in the capacitor shown connected to the input thereof. The oscillation conditions will be analyzed approximately, on the basis of a small-amplitude of oscillation and assuming linear characteristics for the inverters. The transfer function from the output of inverter 104 to the input of inverter 106 can be expressed as:

$$\{1/1 + SR_1C_1\}$$

where $R_1$ denotes the resistance of resistor 105 and $C_1$ the capacitance of capacitor 110. Assuming that S is jw, where $j^2 = -1$ and $wS = 2f$, and that $R_1 = R_2 = R_3 = R$ and that $C_1 = C_2 = C_3 = C$, then the frequency F8A of oscillation of the circuit of FIG. 8A is given by $$f8A = \frac{\sqrt{3}}{6RC}$$

This is obtained on the assumption that a phase shift of $\pi$ radians occurs in each of the amplifier stages, and that the phas delay of each stage is $\pi/3$ radians. The loop gain of the circuit is greater than unity, since each inverter is assumed to have a gain of greater than one. The oscillation frequency is obtained as follows:

$$\left(\frac{\mu}{1 + jwRC}\right)^3 = e^{2n\pi j}$$

where:
  $\mu$ = amplification of each inverter stage;
  $n = 0, \pm 1, \pm 2 \ldots$;
  $j = \sqrt{-1}$;
  $w$ = oscillation frequency in radians/second.

$$\left(\frac{-\mu}{1 + jwRC}\right)^3 = e^{(2n+1)\pi j}$$

$$\frac{-\mu}{1 + jwRC} = e^{(\frac{2n+1}{3})\pi j}$$

$$\therefore -\mu = \left\{\cos\left(-\frac{2n+1}{3}\pi\right) + j\sin\left(-\frac{2n+1}{3}\pi\right)\right\}(1 + jwRC$$

-continued $$\begin{cases} -\mu = \left| 1 + j \cdot \tan \frac{\pi}{3} \right| = 2 \\ wRC = \tan \frac{\pi}{3} = \sqrt{3} \end{cases}$$

It should be noted that it is also possible to obtain the frequency of oscillation by using a different model, based on quantitative analysis.

In actual fact, a delay will occure in each of the inverters, due to the output impedance and input capacitance, so that the actual oscillation frequency will be lower than that obtained on the basis of the above analysis. If we assume that each inverter introduces a first order time lag, and that the transfer function of an inverter is $$\mu \cdot \frac{1}{1 + 3\pi o},$$

rather than $\mu$, then the loop transfer function G(S) of the oscillator circuit can be expressed as:

$$G(S) = \mu^3 \cdot \frac{1}{(1 + 3\pi o)^3} \cdot \frac{1}{(1 + SRC)^3}$$

The value of $\pi o$ is of the order of 1 to $1000 \times 10^8$ seconds for most complementary MOS integrated circuits. The oscillation frequency can therefore be stabilized by reducing the value of $\pi o/(R\ C)$ by using a low frequency of oscillation, so that RC is large, or by stabilizing $\pi o$ with respect to variations in operating temperature and voltage. The input capacitance of an inverter using semiconductor components, as in the case of a ring oscillator constructed on an integrated circuit, varies with the supply voltage applied to the inverter. It is therefore desirable to utilize a stabilized voltage source to supply such a ring oscillator. The maximum operating frequency of the inverter should be high, by comparison with the oscillation frequency.

The oscillation frequency of a ring oscillator of the form of FIG. 10A can be varied by varying any one of resistors 105, 107 or 109, or of capacitors 110, 111 or 112. The number of inverters must be odd, and of three or more. The gain of each inverter must be greater than one, so that the loop gain of the overall circuit is greater than one. The number of RC delay circuits is not limited to three, but can be made greater. Since the loop gain at DC has a negative sign, a DC level which is between the H and L level potentials is established in the initial stages of oscillation, thereby providing a condition of high gain, whereby oscillation at the desired frequency can begin.

Figure 10B:
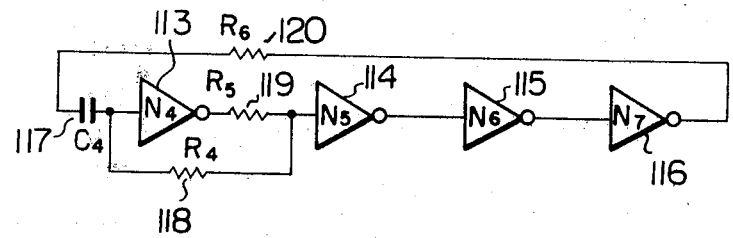
FIG. 10B is a circuit diagram of another ring oscillator circuit suitable for use with the present invention.

FIG. 10B shows an alternative form of ring oscillator circuits, which can be analyzed in a similar manner to that used for the circuit of FIG. 10A. This circui has an even number of stages, but the loop gain at DC is zero. due to the blocking effect of capacitor 117.

The inverters used in a ring oscillator circuit such as those of FIG. 10A and 10B should have their input and output impedances, and amplification, stabilized as far as possible, to ensure stability of oscillation frequency. This can be done by connecting resistors or other impedance elements in series with or parallel with the input and output terminals of the inverters, and by applying local negative feedback to one or more of the inverters in the oscillator. This is exemplified in FIG. 10B, where the amplification of inverter 113 is stabilized by negative feedback through resistor 118, and the output impedance presented by inverter 113 is stabilized by means of series-connected resistor 119.

Figure 11:
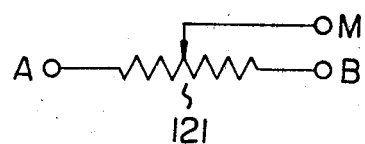
FIG. 11 shows a variable resistor to be incorporated into a ring oscillator circuit such as that of FIG. 10A or 10B, to provide a variable frequency oscillator circuit.
Figure 12:
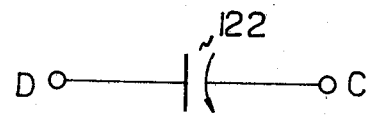
FIG. 12 shows a variable capacitor to be incorporated into a ring oscillator circuit such as that of FIG. 10A or 10B, to provide a variable frequency oscillator circuit.

FIG. 11 shows a variable resistor which can be used in the circuit of FIG. 10A or 10B to provide a variable oscillation frequency. This is done by connecting terminals M and A, or B and M, of variable resistor 121 in place of resistor 105, 107 or 109 in FIG. 10A, or resistor 120 or 119 in FIG. 10B. Alternatively, a variable capacitor 122, as shown in FIG. 12, can be connected in place of capacitor 110, 111 or 112 in FIG. 10A, or 117 in FIG. 10B.

Figures 13A, 13B:
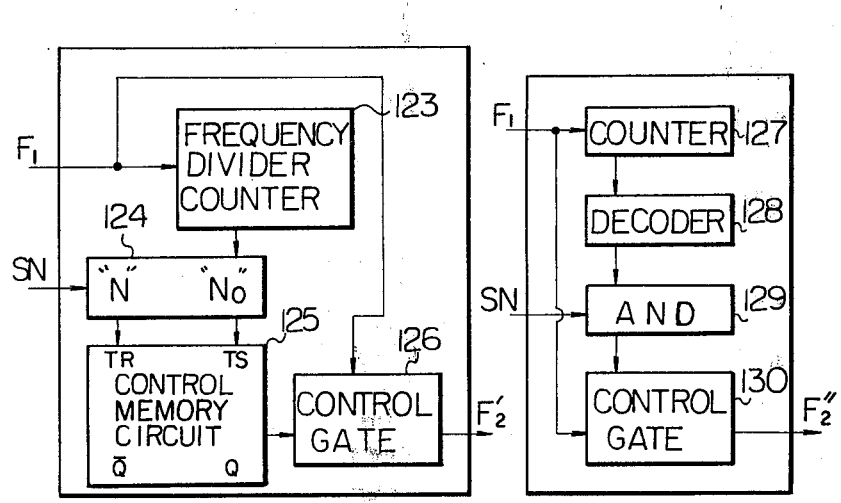
FIG. 13A, 13B and 13C are block diagrams of examples of frequency synthesizer systems suitable for use in a pace timing device according to the present invention, to provide a variable frequency signal.
Figure 13C:
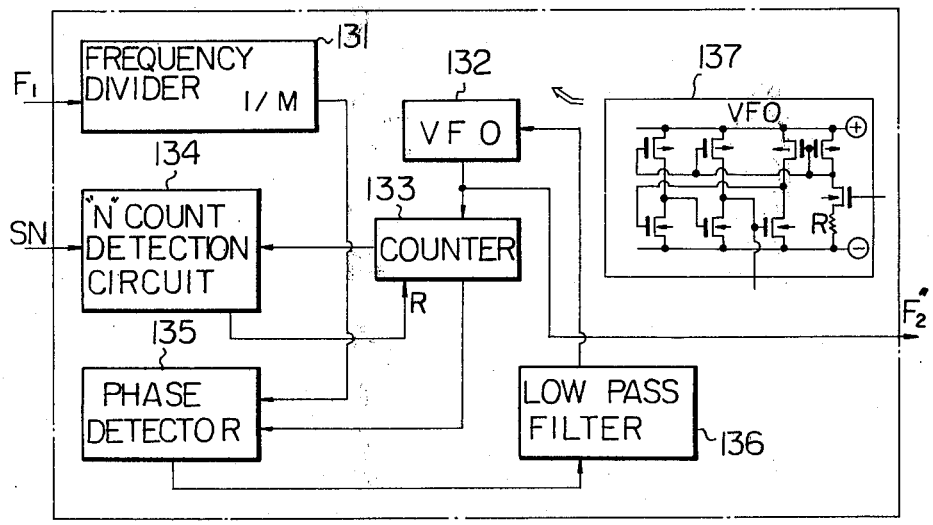

Referring now to FIG. 13A, 13B and 13C, frequency synthesizer circuits suitable for use in a pace timing device according to the present invention will be described. A frequency synthesizer circuit is inherently capable of providing a higher degree of accuracy and stability as a source of a variable frequency signal, since an output signal can be provided which is an integral submultiple of a constant fixed frequency. This constant fixed frequency can be provided from a source such as a quartz crystal oscillator circuit, which provides an output of high stability with respect to variation in supply voltage, operating temperature, etc. In FIG. 13A, F1 denotes a reference frequency signal, of relatively high frequency, and F2 denotes the output signal, which is a submultiple in frequency of signal F2. Numeral 123 denotes a frequency divider circuit providing a division factor of M at its final output.

Numeral 124 denotes a circuit which serves as a count comparator and a memory circuit, the memory function being provided by means such as a counter circuit. SN denotes a frequency control signal which can be appliwed to the memory circuit of section 124 in order to increase or decrease a count value stored therein. Numeral 125 denotes a control memory circuit, which can comprises a flip-flop for example. The output of control memory circuit 125 is connected to a control input of gate circuit 126, to control the passage of pulses of signal F1 through gate circuit 126. We may assume, for ease of description, that gate circuit 126 is enabled when the Q terminal of circuit 125 is at the H level, and is inhibited when the Q terminal is at the L level. The count stored in memory/comparator circuit 124 can range from a minimum value of NO (which may be zero) to a maximum which may be as large as M, for example. The actual count stored is denoted by the letter N. When circuit 124 detects coincidence between the minimum value NO and the count in frequency divider 123, then an output signal is produced which sets control bistable circuit 125 in a state where the Q terminal is at the H level, so that pulses F1 can pass through gate circuit 126. When the count of frequency divider 123 becomes equal to the value N, then this coincidence is also detected, and a signal is generated by circuit 124 which resets the Q output of control memory circuit 125 to the L level, thereby inhibiting further passage of F1 pulses therethrough. Subsequently, when the count of frequency divider 123 again reaches a value of NO, gate circuit 126 is again enabled to pass pulses F1. In this way, periodic bursts of pulses are provided from gate circuit 126, to form signal F2. The average frequency of signal F2, over a relatively long time period, is given by:

$$F2 = \frac{(N - N0)}{M} \cdot F1, \text{ or } \frac{N}{M} \cdot F1 \text{ if } N0 \text{ is zero.}$$

The fact that pulses are produced in periodic bursts may be a disadvantage, but this may be immaterial if signal F2 is then frequency divided by a relatively large number of stages.

It should be noted that it is also possible to apply an output from some stage of frequency divider 123 to the input of gate circuit 126, rather than signal F1.

Another form of frequency synthesizer is illustrated in FIG. 13B. Here, numeral 127 denotes a frequency divider circuit which receives a fixed frequency signal F1 of relatively high frequency, and produces thereby output signals from various stages of successively decreasing frequency. These are applied to a decoder circuit 128, which generates a set of weighted gating signals. Each of these signals has the same period, which is that of the lowest frequency output of frequency divider 127, but have successively increasing pulse width, from that of the highest frequency outpout of frequency divider 127 up to that of the lowest frequency output. These signals are applied to a selection and memory circuit 129, which is responsive to a selection input SN for selecting one or more of the weighting gate signals. The selected signals are applied to an output gate circuit 130, to control the passage of a signal consisting of pulses at a relatively high frequency, which may comprise the input signal P1 or can be the output signal of an early stage of frequency divider 127. Thus, as the case of the circuit of FIG. 13A, repetitive bursts of high frequency pulses can be produced, with the number of pulses in each burst (and therefore the average frequency of output signal F2') being determined by the weighting valves of the weighted gating signals selected by input SN. The weighting values will normally be arranged in binary progression, i.e. as $2^0$, $2^1$, $2^2$, ....

Referring now to FIG. 13C, a third type of frequency synthesizer is shown. This is of phase locked loop configuration, and provides the advantage of an output signal which is substantially free from irregularity or jitter, as compared with the circuits of FIGS. 13A and 13B. A frequency divider 131 receives an input signal F1, of fixed frequency, and has a division ratio of 1/M. The output signal from a voltage controlled oscillator 132 is applied to a counter circuit 133, the output of which is applied to one input of a phase detector 135. The output of frequency divider 131 is applied to another input of phase detector 135. When a difference in phase between the output of frequency divider 131 and of counter 133 is detected, a control signal is generated by phase detector 135 and is applied through a low-pass filter 136 to a control input terminal of voltage controlled oscillator 132. The outputs of frequency divider 131 and counter 133 are therefore locked in phase, so that the frequency of the output signal F2'' produced by voltage controlled oscillator 132 is determined by the frequency of the output signal from frequency divider 131 and the counter factor of counter 133. Numeral 134 denotes a memory and comparator circuit, which can store a count value N which is input by signal SN. When circcuit 134 detects that the count in counter 133 is equal to N, then a reset signal is produced and applied to counter 133 to set the contents thereof to zero. The count factor of counter 133 can thus be effectively controlled by means of input SN, so that the frequency of signal F2'' can be varied as required.

Numeral 137 in FIG. 13C indicates a suitable circuit for voltage controlled oscillator circuit 132, applicable to C-MOS integrated circuit construction. This is a ring oscillator circuit, in which the phase shifts due to the input capacitances and output resistances of C-MOS inverter stages are utilized to provide the conditions for oscillation.

Figure 15:
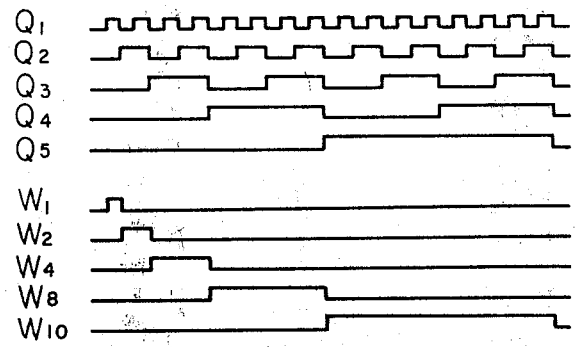
FIG. 15 is a waveform diagram for the frequency synthesizer of FIG. 14.

FIG. 14 is a general block diagram of a pace timing device which incorporates a frequency synthesizer of the form described above with respect to FIG. 13B. The waveforms of the output signals Q1 to Q5 of frequency divider 324 in FIG. 14, and weighted gating signals W0, W2, W4, W8 and W16 generated by a decoder circuit 328, are shown in FIG. 15. Numeral 330 denotes a selection and memory circuit, which performs the functions of block 129 in FIG. 13B, i.e. to select particular combinations of weighted gating signals produced by decoder 328, as commanded by a signal input from setting means 331. The selected combination of weighted gating signal is applied to an output gate circuit 332, to control the passage of high frequency pulses TB from the input to frequency divider 324, as shown in FIG. 14. The form of the weighted gating signals is shown in FIG. 15, and it can be seen that the weights proceed in binary progression, from W0 to W16, i.e. as $2^0$ to $2^4$. It can be seen that the weighted gating signals W0 to W16 do not overlap, so that various combinations of these signals may be used to control the gating of varying numbers of high frequency pulses in output gate circuit 332. The logical combinations of the output signals Q1 to Q5 of frequency divider 324 by which the weighting gate signals are produced are as follows: $W1 = \overline{Q5} \cdot \overline{Q4} \cdot \overline{Q3} \cdot \overline{Q2} \cdot Q1$, $W2 = \overline{Q5} \cdot \overline{Q4} \cdot \overline{Q3} \cdot Q2$, $W4 = \overline{Q5} \cdot \overline{Q4} \cdot Q3$, $W8 = \overline{Q5} \cdot Q4$, $W16 = Q5$. In one period of signal Q5, weighted gating signals W1, W2, W4, W8 and W16 can gate through pulse groups of signal TB consisting of 1, 2, 4, 8 and 16 pulses respectively. Circuit block 332 also comprises counter circuit means for counting the pulses thus gated, in order to produce a first frequency signal consisting of a pulse train of regularly recurring pulses at a repetition rate determined by the average frequency of the high frequency pulses gated by the weighted gating signals. This average frequency can be varied by selecting various combinations of the weighted gating signals, through signals generated by setting means 331.

Figure 16A:
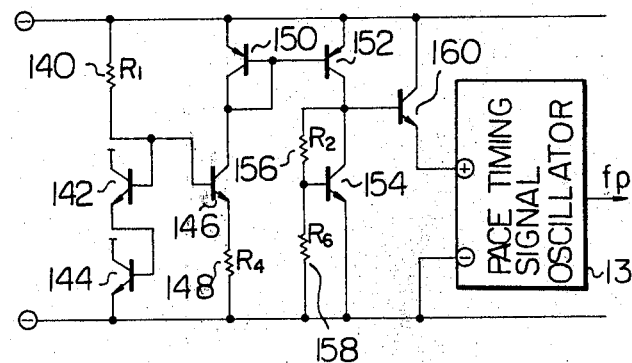
FIG. 16 is a circuit diagram of a stabilized voltage source which is suitable for providing a stabilized voltage to an oscillator circuit utilizing bipolar transistors.
FIG. 16B and 16C illustrate a method of compensating for the variation in base-to-emitter forward voltage of a bipolar transistor with temperature.

As stayed previously, in the description of the oscillator circuit of FIG. 3, the stability of a bipolar transistor ring oscillator circuit is affected by changed in the base-emitter forward voltage; Vbe with temperature variations, and by changes in the DC supply voltage of the circuit. FIG. 16A shows a stabilized power supply circuit which is suitable for supplying such a bipolar transistor oscillator circuit, by providing a stabilized DC voltage which utilizes the Vbe of bipolar transistors as a reference voltage. The stabilized DC voltage therefore varies in such a way with temperature as to compensate for the effects of Vbe variations in the oscillator circuit which it supplies. The reference voltage is developed across series-connected transistors 142 and 144, each of which is connected as a diode, between base and emitter, with the collector left open circuit. A current determined by resistor 140 flows through the base and emitter of transistors 142 and 144. This reference voltage is applied to the base of a transistor 148, and has a value 2. Vbe, where Vbe is the forward voltage developed across each of transistors 142 and 144. A resistor 148 is connected in the emitter of transistor 146. The voltage develope across resistor 148 is approximately Vbe, so that a current of the order of Vbe/R4 flows in the collector of transistor 146, where R4 is the resistance of resistor 148. Transistors 150 and 152 are connected in the well known current mirror configuration, so that a current which is almost equal to the current flowing through the base and emitter of transistor 150 also flows through transistor 152. Transistor 152 thereby functions as a current source, supplying a current of approximately Vbe/R4. This current is supplied to the collector of transistor 154 and to resistors 156 and 158 connected in series. Due to the negative feedback applied between collector and base of transitor 154 by resistors 156 and 158, the collector voltage of transistor 154 is held almost constant at a value of Vbe. (R6+R2)/R6, where R2 and R6 are the resistances of resistors 156 and 158 respectively. Any change in this voltage results in a current flowing in the base of transistor 154 which causes a compensating change in the collector voltage of transistor 154.

Transistor 160 is of emitter follower configuration, and the voltage appearing at its emitter is approximately Vbe.(R6+R2)/R6−Vbe, which is R2/R6·Vbe. The stabilized output voltage therefore is independent of the supply voltage of the stabilizer circuit, and varies in accordance with Vbe.

Figure 16B:
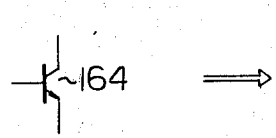
Figure 16C:
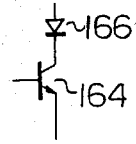

FIGS. 16B and 16C indicate a simple method of reducing the effect of variations in Vbe of a transistor in an oscillator circuit. If a transistor is shown in FIG. 16B has a diode connected in series with its collector, (this can be a diode-connected transistor), then a variation in the Vbe of the transistor will be accompanied by a similar change in the voltage applied to the collector, thereby tending to compensate for the change in Vbe.

Figure 17:
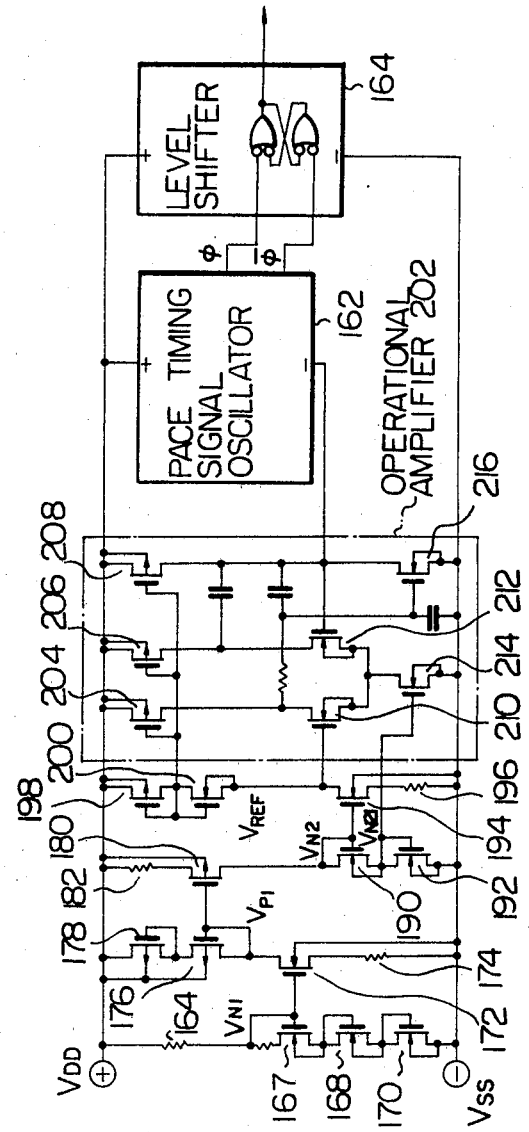
FIG. 17 is a circuit diagram of a stabilized voltage source which is suitable for providing a stabilized voltage supply to an oscillator circuit utilizing complementary field effect transistors.

FIG. 14 shows a voltage stabilizer circuit which is suitable for supplying an oscillator circuit employing complementary field effect (CMOS) transistors. In this circuit, a combination of the threshiold voltages of P-channel and N-channel MOS transistors is used as the reference voltage. In the circuit of FIG. 17, resistors 164, 174, 182, and 196 are of linear diffusion type or non-linear type, although these are shown as being provided by the P-channel field effect transistors. These resistors serve as virtually constant-current load resistances, in order to provide higher gain in the amplifier circuit of the voltage stabilizer and because they take less space on the integrated circuit chip as compared with linear diffusion resistors. The circuit also includes N-channel field effect transistors 167, 168, 170, 172, 192, 194, 210, 210, 212, 214 and 216, and P-channel transistors 178, 176, 180 and 198. Numeral 212 denotes an operational amplifier section. The stabilized output voltage is supplied to an oscillator circuit 162, which produces, for example, the first frequency signal of a pace timing device. Numeral 164 denotes a level shifter circuit, to enable a stabilized voltage to be applied to the oscillator circuit which is substantially less than the supply voltage of the voltage stabilizer circuit, and to do this without dissipation of power. This reduction of the voltage applied to the oscillator circuit is desirable because of the fact that in a CMOS integrated circuit which operates at very low power levels, the power consumed by a high frequency oscillator is extremely high, by comparison with other portions of the circuitry. The output signal from the oscillator circuit can be restored to the normal level by means of a second level shifter, 164.

The operation of this circuit is basically similar to that of FIG. 16A, and will not be described in detail. The reference voltages are developed acros transistors 167, 168 and 170 and across 190 and 192, which are all N-channel type, and also across transistors 176 and 178, which are of P-channel type.

The type of battery which is used in a portable electronic device such as a pace timing device has an important influence upon the operation of the device. The peak current required to drive an acoustic device, for providing a pace timing indication for example, ranges from 1 mA to 100 mA. If the battery also supplies power to an oscillator circuit, such as a ring oscillator circuit, then the operating frequency of the oscillator circuit will be affected by operation of the acoustic device, unless the battery has a sufficiently low internal resistance. This problem can be overcome, however, by supplying power to the oscillator circuit by means of a stabilized power supply of a type such as described above in FIG. 16 and 17. It has been found that a ring oscillator circuit can be utilized effectively as a variable frequency oscillator, if the oscillation frequency is suitably chosen, and if the power supply is stabilized. Batteries such as nickel-cadmium or lead secondary batteries have a suitably low level of internal resistance for such applications, so that in some cases stabilization of the power supply to the oscillator circuit may not be necessary. Silver oxide cells utilizing potassium hydroxide electrolyte or a sodium hydroxide electrolyte also have a suitably low level of internal resistance. However commercially available manganese dioxide type cells exhibit a relatively high level of internal resistance, as do cells utilizing organic electrolytes. With such cells, it is necessary to use a stabilized power supply to operate an oscillator circuit, if a precise output frequency is required.

The average level of power consumption of a pace timing device of typical design is usually quite small, since audible signals are only produced intermittently. For example, if we assume that a pace timing device is used for 60 minutes per day, and that the total time of operation of the loudspeaker is 60 seconds, including pauses, then if the duty ratio of the pulses in the drive signal to the loudspeaker is $\frac{1}{8}$ and the maximum drive current is 1 mA, the yearly consumption is; 1 mA×($\frac{1}{8}$)×60 seconds×465 days=0.76 mA hr.

Thus, a miniature silver oxide cell having a capacity of 10 mA-h can provide about ten years of operating life. This is longer than the storage life of such a battery, which is usually of the order of 3 to 5 years. It is therefore advantageous to use a battery having a long storage life, such as a lithium cell. Since such a cell has a comparatively high internal resistance, an electromagnetic loudspeaker presenting a high impedance should be used as the acoustic device and a capacitor should be connected in parallel with the battery to lower the AC impedance.

It is also possible to utilize a rechargable battery such as a nickel cadmium cell. A silver oxide cell can also be used as a rechargable cell, but in either case, care must be taken to avoid overcharging.

Figure 18A:
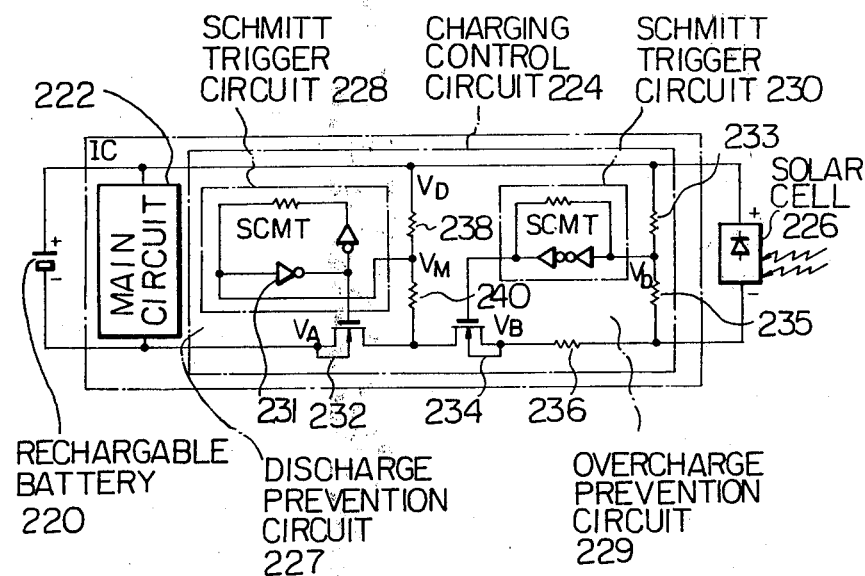
FIG. 18A is a block diagram of a system for charging a rechargable battery of a pace setting device from a solar cell array.

FIG. 18A is a general block diagram of a portable electronic device such as a pace timing device equipped with a rechargeable battery and a charging control circuit which permits recharging from a photoelectric energy transducer such as an array of solar cells 226, and with provision for prevention of overcharging. Numeral 220 denotes the rechargeable battery and 222 is the main circuit of the device. Numeral 224 denotes a charging control circuit which serves to prevent overcharging of battery 220 by solar cell array 226 and also prevents discharge of the battery when the voltage of solar cell array 226 falls below a predetermined value. The number of cells in the solar cell array is determined by the battery voltage and the expected exposure to light of the array. The output voltage of a semiconductor type of solar cell remains substantially constant as the intensity of incident light is increased, but the internal resistance of the solar cell decreases. If the expected intensity of light were constant, then it would be possible to utilize only sufficient solar cells to provide a slightly greater voltage than the battery voltage, which is 1.6 V approximately for a silver oxide battery. However in practice, the exposure to light will be very variable in the case of a device such as a wrist-mounted pace timing device, so that with the minimum number of solar cells, there would be a danger of discharging the battery through the solar cells. It is therefore desirable to provide a greater number of cells in the solar cell array, for example 6 solar cells each providing 0.45 V output, to charge a 1.6 V silver oxide battery. This however results in a danger of overcharging the battery. In the circuit of FIG. 18A, the voltage developed across resistor 236 increases as the amount of charging current increases, causing the potential Vb developed at the junction of resistors 233 and 235 to fall. When Vb falls below a predetermined level, then a Schmitt trigger circuit 230 is triggered, causing the voltage applied to the gate of transistor 234 to switch to a low level, i.e. the L level. Since transistor 234 is a N-channel field effect transistor, it is thereby placed in the non-conducting state between drain and source, so that further charging of battery 220 from solar cell array 226 is halted. Use of a Schmitt trigger circuit ensures that transistor 234 is either in the fully ON state or in the fully OFF state.

The voltage developed by solar cell array 226 during charging is detected by a second Schmitt trigger circuit 228, by means of the voltage Vm developed at the junction of resistors 238 and 240. When voltage Vm falls below a predetermined level, then the output of the first inverter 229 of Schmitt trigger circuit 228 goes to the H level, thereby causing switching transistor 232 to go to the non-conducting state. Discharge of battery 220 through solar cell array 226 is thereby prevented.

Figure 18B:
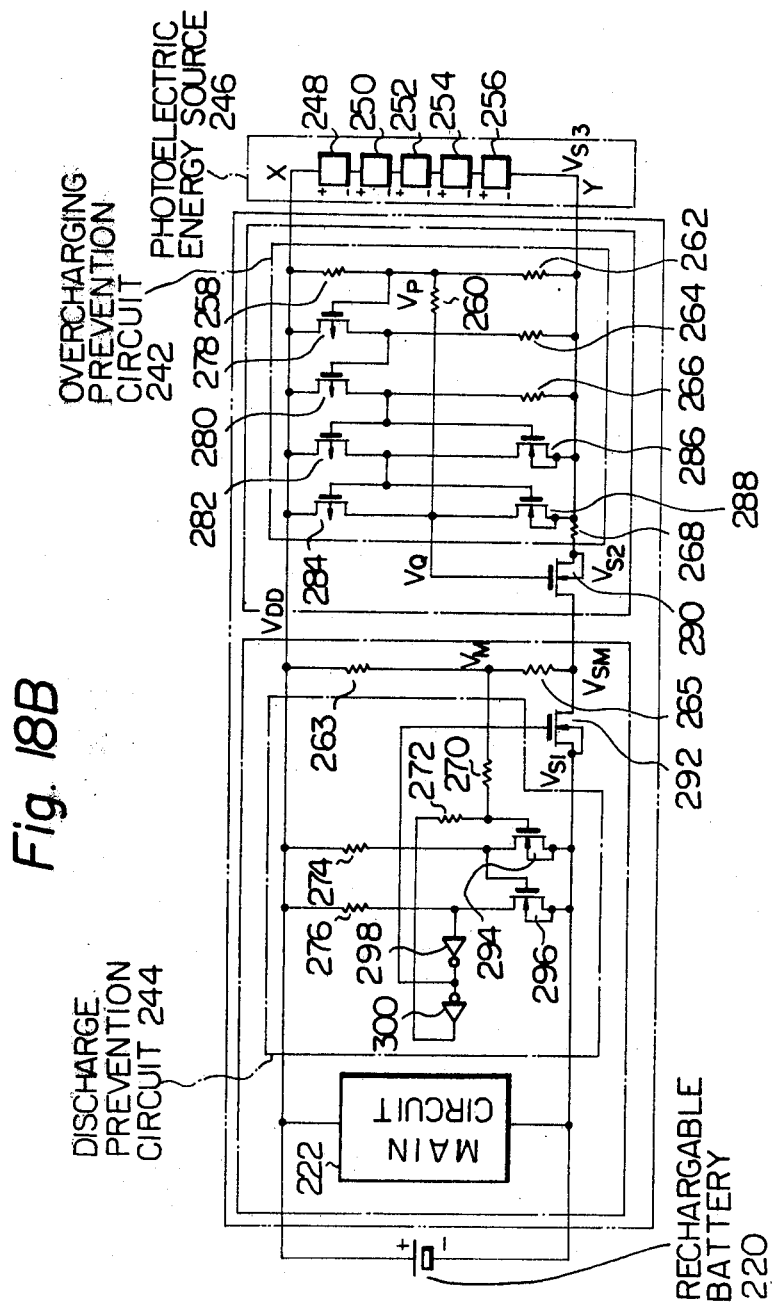
FIG. 18B is a circuit diagram of a system for charging a rechargable battery, in accordance with the block diagram of FIG. 16A.

FIG. 18B shows a practical circuit diagram for a battery charging system of a solar cell powered pace timing device, based on the general diagram of FIG. 18A. Solar cell array 246 comprises, for example, separate epitaxial layers formed on a silicon wafer which also carries the other circuitry of the device. Resistors 258, 260, 262, 264, 266, 270, 272, 274, and 276 are formed of boron-doped polysilicon, or are diffusion resistors. Transistors 278, 280, 282 and 284 are P-channel enhancement type, and transistors 286, 288, 290, 292, 294 and 296 are N-channel enhancement type. Numeral 242 denotes an overcharging prevention circuit similar to that of FIG. 18A, in which the voltage developed across resistor 268 is detected, and causes the voltage Vp to fall as the charging current of battery 220 increases. When Vp falls below a predetermined level, the output of a Schmitt trigger circuit which is coupled to the junction of resistors 258 and 262 to receive voltage Vp, falls to the L level, so that switching transistor 290 goes to the non-conductive state. Due to the hysteresis of the Schmitt trigger circuit, the output voltage applied to the gate of switching transistor 234 is held at the L level by feedback through resistor 260, until the output voltage of solar cell array 246 falls below a second predetermined level, which is lower than the first mentioned predetermined level. This Schmitt trigger circuit is composed of transistors 278, 280, 282, 284, 286 and 288, and feedback resistor 260.

Similarly, when the voltage of solar cell array 246 goes below a predetermined level, then the resultant drop in voltage Vm, at the junction of resistors 263 and 265, is detected by a Schmitt trigger circuit composed of transistors 294 and 296 and inverters 298 and 300, with feedback resistor 270. Switching transistor 292 is thereby switched to the non-conducting state to prevent discharge of battery 220 through solar cell array 246.

The manner in which switching transistors 290 and 292 are connected, with their drain terminals connected together, serves to prevent either of the drain terminals from becoming forward biased with respect to the substrate, and therefore prevents a leakage current from flowing thereby, with a resultant drain on the battery.

Figure 19:
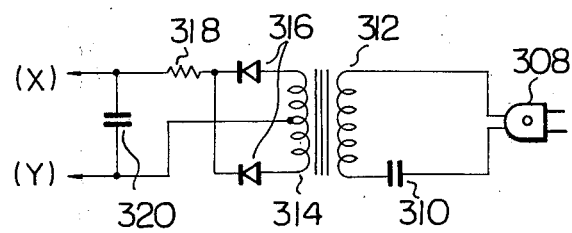
FIG. 19 is a circuit diagram of a system for charging a rechargable battery of a pace setting device from a commercial line power supply.

FIG. 19 shows a circuit for charging a battery, such as battery 220 of FIG. 18B, from a commercial power supply. The circuit comprises a power plug 308, connected to the primary of a transformer 312 through a capacitor 310, which serves to reduce the voltage applied to transformer 312. This enables the size of transformer 312 to be reduced without dissipation of heat. The secondary of transformer 312 is connected to rectifiers 316 and 314, the output from which is passed through a resistor 318. This resistor serves to protect against excessive current flow in the event of short-circuit of the output terminals, which are connected across a smoothing capacitor 320. The output voltage of the power supply circuit can be connected directly to points X and Y of the circuit of FIG. 18B.

Referring now to FIG. 20, a general block diagram of a pace timing device according to the present invention is shown. Numeral 87 denotes a source of a fixed frequency timebase signal, such as a quartz crystal vibrator circuit. The timebase signal is applied to a frequency divider 342 in a frequency synthesizer circuit block 340. Numeral 20 denotes setting means, comprising switches, etc., by which input signals can be applied by the user, in order to set various parameters of the device as required. The setting means can be used to store a numeric value in a frequency synthesizer circuit 344, and this value is compared with the contents of frequency divider 342 by means of a frequency synthesizer comparator circuit 344. A signal of desired frequency is thereby produced by frequency synthesizer comparator circuit 346. A time unit signal produced by frequency divider 342 is applied to a time counter 348 in a timekeeping circuit block 346. A desired numeric value, representing the duration of a time interval, can be stored in timer memory 352, by means of signals applied from setting means 20. Time lapse coincidence detection circuit 350 compares the stored value in timer memory 352 with the contents of time counter circuit 348, and when coincidence is detected, produces a time marker signal which is applied to a modulator circuit 364. A carrier signal of relatively high audio frequency is thereby modulated in modulations circuit 364 and applied to a driver circuit 24, causing an audible tone burst to be generated by acoustic device 26 when a time interval corresponding to the numeric value stored in timer memory 352 has elapsed. The output of frequency synthesis comparator 346, which is a first frequency signal for determining the repetition frequency of steps or other physical actions, is also applied to an input of modulator circuit 364, as well as to an input of a step counter circuit 356. A numeric value to indicate a number of steps can be stored in a step number memory circuit 356, by means of signals produced by setting means 20. This stored numeric value is compared with the contents of step counter 356, by a step number coincidence detection circuit 358, and when coincidence is detected, an output signal is applied from step number coincidence detection circuit 358 to an input of modulation circuit 364. In this way, a tone burst of particular pitch, timbre and duration is produced for each of the pulses in the first frequency signal generated by frequency synthesis comparator 346, while a tone burst of distinctively different pitch, timbre or duration is generated by acoustic device 26 when a number of steps equal to the numeric value stored in step number memory circuit 356 has been counted.

As discussed previously in this description, it is possible to provide audible information concerning elapsed time, numbers of steps, etc, by means of a "repeater" facility. Values such as 10 minutes, 20 minutes, 30 minutes, etc., or 1000 steps, 2000 steps, 3000 steps, etc. can thereby be indicated by a single tone burst, two immediately consecutive tone bursts, three immediately consecutive tone bursts, ect. In the embodiment of FIG. 20, such a repeater facility is provided for indicating the passage of successive time intervals, such as ten minute intervals. The actual duration of the intervals to be measured can be set by the user, by setting a corresponding numeric value in a time repeater memory 360 through signals applied from setting means 20. The stored numeric value is compared with the contents of time counter 348 by means of a time coincidence detection circuit 362, such that each time the contents of time counter 348 have been incremented by an amount equal to the value stored in time repeater memory circuit 360, an output signal is applied from time coincidence detection circuit 362 to modulation circuit 364. This output signal is controlled such that a single tone burst is generated by audio device 26 the first time coincidence is detected, a pair of tone bursts are generated the second time that coincidence is detected, three tone bursts are generated the third time, etc. The pitch, timber or duration of these tone bursts is made distinctively different from those of the pace timing indication signals, by means of modulator circuit 364. The user is thereby notified of the passage of time while exercise is in progress, without the necessity for looking at a timepiece dial.

It is also possible for the user to obtain an approximate indication of the elapsed time while exercise is in progress, at any desired point in the exercise. This is done by applying a relatively high frequency signal from frequency divider 342 to an input of time repeater memory 360, to thereby cause the contents of time repeater memory 360 to be rapidly advanced until coincidence is detected by time coincidence detection circuit 362, whereupon a "repeater" time indication will be given audibly to the user. Application of the high frequency signal (indicated by a broken line in FIG. 20) is controlled by the user through setting means 20.

Display means, such as an electro-optical display device, can be provided to indicate various information, as denoted by numeral 28.

A detailed embodiment of a pace timing device in accordance with the present invention will now be described, with reference to the circuit diagrams of FIGS. 21A, 21B, 21C and 21D and the waveform diagrams of FIGS. 22, 23, 24A, 24B, 24C, and 25. This embodiment can be set by the user to provide a pace timing signal either with or without a rythm component, and the user can also cause a "repeater" audible indication to be given after each 10 minutes of exercise or after each 1000 steps of an exercise have been completed. Very broadly speaking, the circuit of FIG.21A handles the generation of various timing reference signals based on a quartz crystal oscillator timebase signal source, FIG. 21B shows circuitry which serves to generate the various signals required for operation of the repeater facility, FIG. 21C deals with the circuitry by which input signals generated by the user, through switch actuations, are processed in order to set various operating conditions, and FIG. 21C covers the circuitry by which the audible pace timing signals, etc., are generated.

Figure 21A:
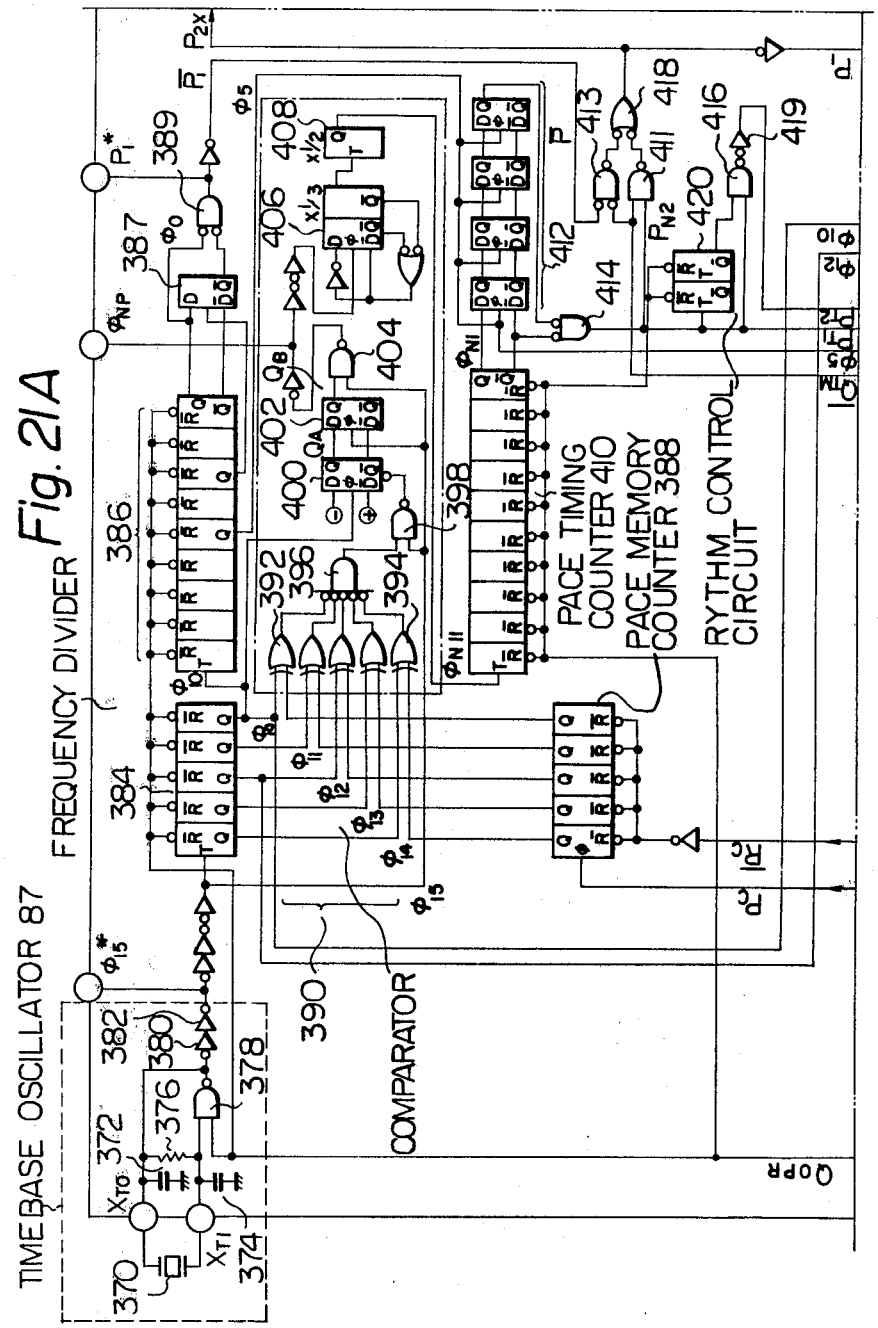
Figure 21B:
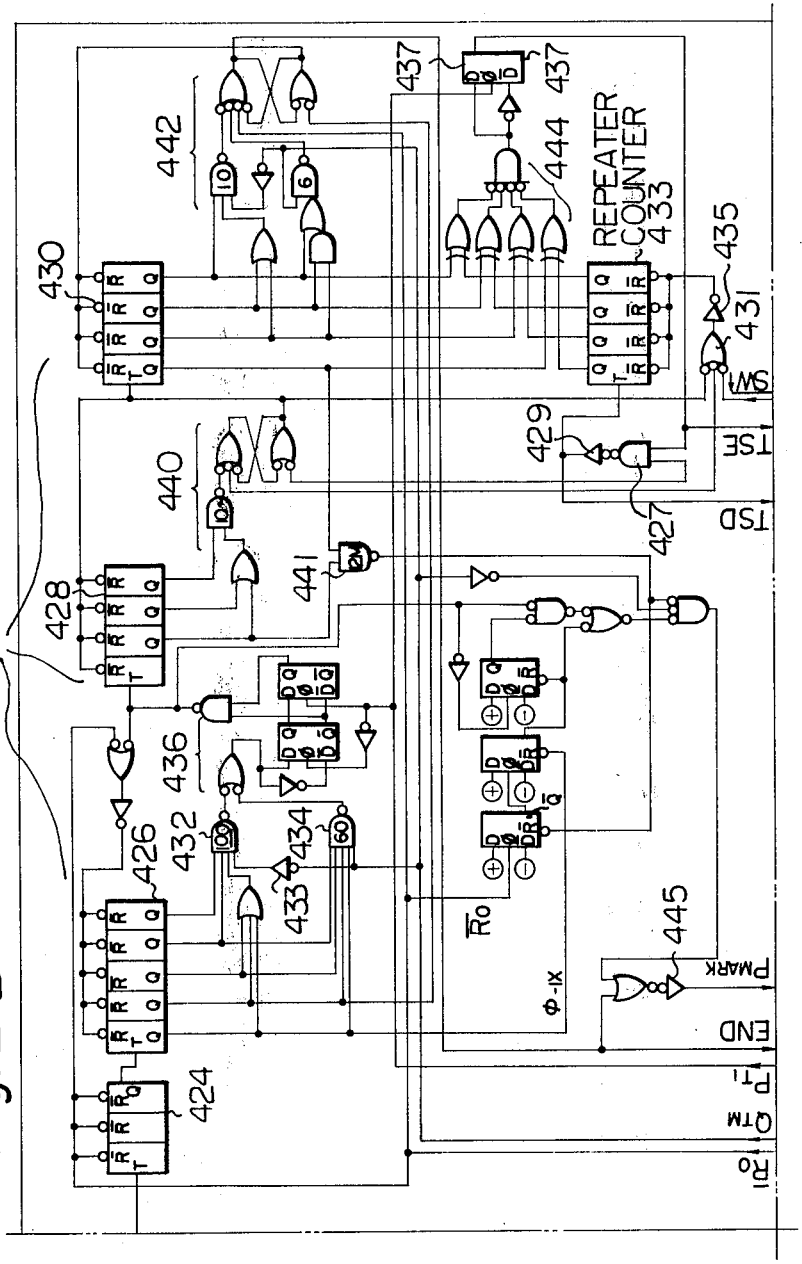

Referring first to FIG. 21A, numeral 87 denotes a quartz crystal vibrator oscillator circuit, for generating a timebase signal. In addition to quartz crystal, it is also possible to use crystalline lithium tantalate, or barium titanate, for example, as materials for piezo-electric vibrator 370. The vibrator 370 of this embodiment is of tuning fork type, with $+5°$ X-cut configuration, and an oscillation frequency of $2^{15}$ Hz. It should be noted that all components of this embodiment other than vibrator element 370, a control switch 486, and a miniature loudspeaker 458, are provided on a single integrated circuit ship. Capacitors 372 and 374 of oscillator circuit 87 are formed on the circuit chip, with $SiO_2$ serving as the electric. Numeral 372 denotes a bias resistor, and 378 a control gate, comprising a NAND gate. When a control signal Popr applied to control gate 378 is at the H potential level, then oscillator circuit 87 is enabled to operate, while when signal Popr is at the L level, oscillation is inhibited. The output of control gate 378 is applied to the input of two series-connected inverters 380 and 382, for waveform shaping. It is possible to operate circuit 87 as an oscillator circuit without a piezo electric vibrator element, by connecting terminal 15 and terminal $X_{T1}$ together, through a combination of a resistor and capacitor, to form a ring oscillator circuit.

Numerals 384 and 386 denote frequency divider circuits comprising counter circuits, with the output signal from frequency divider 384 being applied to the input of 386. This signal, designated $\phi_{15}$, has a frequency of 1024 Hz. Numeral 388 denotes a pace memory circuit, which is used to store a numeric value which determines the frequency at which pace timing signals are to be generated. This value, stored in pace memory counter 388 as a binary number, is compared with the contents of frequency divider 384, by comparator circuit 390. The value stored in counter 388 can be varied by the user, by generating a pace memory advance signal Pc, in a manner to be described hereinafter. For each positive to negative transition of signal Pc, the count in counter 388 is incremented by one. Comparator 390 comprises 5 Exclusive-OR gates, 392 to 394, and a NOR gate 396, the output of which goes to the H level when coincidence occurs between the contents of counter circuits 388 and 384. The output of gate 396 is applied to an input of a NAND gate 398, which also receives the input signal $\phi_{15}$ applied to frequency divider 384. Signal $\phi_{15}$ is also applied to the clock terminal of a data-type flip-flop 402, and to an input of a NAND gate 404 which also receives the output of flip-flop (abbreviated hereinafter to FF) 402, Qb. The Q output of FF 400 is applied to the data input terminal of FF 402. The output signal from the final stage of frequency divider 384, $\phi_{10}$, which has a frequency of 1024 Hz, is applied to the clock terminal of FF 400. The output of NAND gate 398 is coupled to the reset terminal of FF 400. For all of the flip-flop circuits in this embodiment, an L level signal applied to the reset terminal causes the flip-flop to be reset. NAND gate circuit 404 generates repetitive bursts of pulses, with the number of pulses in each burst being equal to the numeric value stored in counter 388, in a manner which will now be described. Each time signal $\phi_{10}$ goes to the L level from the H level, output Qa of FF 400 goes to the H level, since its data terminal is connected to the H potential. On the next H level to L level transition of signal $\phi_{15}$, the output Qb of FF 402 therefore goes to the H level. If we assume that a numeric value N is stored in counter 388, then after N pulses of signal $\phi_{15}$, the output of gate 396 will go to the H level, so that the output of NAND gate 398 will go to the L level. FF 400 is thus reset, so that signal Qa goes to the L level. Upon the negative-going transition of the next $\phi_{15}$ pulse, the output Qb of FF 402 will go to the L level, i.e upon the (N+1) th of the $\phi_{15}$ pulses. While signal Qb is at the H level, N pulses of the $\phi_{15}$ signal are passed by NAND gate 404. It will be seen that the synchronization provided by FF 402 enables signal $\phi_{15}$ to be gated by NAND gate 404 without any spurious spikes being generated thereby, which could occur if signals $\phi_{15}$ and Qa were directly applied to a gate together.

In this embodiment, the repetition rate of the pace timing signal (with no rhythm component) is to be 120 steps per minute, when a value of 12 is held in counter 388. Output signal $\phi_{NP}$ from NAND gate 404 is therefore subjected to 1/6 frequency division in dividers 406 and 408, and is subjected to frequency division by a factor $2^{-10}$ in a frequency divider 410. The output signal from frequency divider 410, $\phi_{N1}$, is applied to delay circuit 412, the output of which is applied to one input of a NOR gate 417. The inverse of signal $\phi_{N1}$ is applied to the other input of gate 417. Delay circuit 412 comprises four data type flip-flops. The output of NOR gate circuit 414 consists of a train of pulses constituting the first frequency signal, the frequency of which is identical to the output from frequency divider 410 but whose pulse width is determined by delay circuit 412. This signal, designated PT1, is shown in the waveform diagram of FIG. 23. It can thus be seen that the combination of delay circuit 412 and gate 414 serves to provide a first frequency signal PT1 having the requisite duty cycle.

Signal PT1 is applied to a toggle terminal of a pair of toggle-type flip-flops 420, which together with AND gate 416 and inverter 419 constitute a rhythm control circuit. The inverted output of FF 420 is applied, together with signal PT1, to inputs of AND gate 416, the output of which is applied to inverter 419. A first frequency signal having a rhythm component PT 2 is thereby produced by inverter 419, having the waveform shown in FIG. 23. Signal PT2 is a pulse train which is identical to PT1, except for the fact that alternate pairs of successive pulses are omitted from signal PT2. Signal PT2 can therefore be used to produce an audible pace timing signal which has a rhythm component. Such a signal can be more attractive than a regularly repeated pace timing signal, for timing exercise actions, as has been previously discussed hereinabove.

An output from frequency divider 386, is applied through data type flip-flop 387 and serves as a time unit signal, NOR gate 389 to provide a time unit signal $\overline{P1}$. Signal $\overline{P1}$ is applied to one input of a NOR gate 413. Signal PT1 is applied to one input of a NAND gate 411. A control signal $\overline{Qtm}$ is applied to other inputs of gate 413 and gate 411. When signal $\overline{Qtm}$ is at the H level, then signal PT1 is passed through NAND gate 411, and then through a gate 418, to be applied as signal P2x to a counter circuit in FIG. 21B. If signal $\overline{Qtm}$ is at the L level, then signal $\overline{P1}$ is passed through at the L level, then signal $\overline{P1}$ is passed through gate 413 and through gate 418, to be applied to the counter of FIG. 21B as signal P2x. The user can thus determine whether counting of numbers of steps (by signal PT1) or of time intervals (by signal $\overline{P1}$) is to be performed, by setting the level of signal $\overline{Qtm}$ as required. Signal $\overline{P1}$ is also inverted, and applied to the circuit of FIG. 21C, for use as a timing signal P1, as described later.

In FIG. 21A, and in FIG. 23, various signals designated as $\phi_{N1}$, $\phi_{N2}$, etc. are shown. Here, "N" represents the count held in counter 388, which determines the frequency of these signals. For example, if the count in counter 388 is 12, then the frequency of signal $\phi_{N1}$ is given by:

$$2^{15} \times (N/32) - 6 \times 2^{-10}, \text{ i.e. N/6 Hz, or 2 Hz.}$$

The pulse width of each of signals PT1 and PT2 is approximately 120 msec. However this can easily be changed. If signal $\phi_6$ is applied to the clock terminals of delay circuit 412, rather than signal $\phi_5$, then the pulse width of signals PT1 and PT2 becomes 60 msec, for example.

Referring now to FIG. 21B, signal P2x is applied to the input of a frequency divider 424, which perform frequency division by a factor of ⅙, and supplies an output signal to a frequency divider 426. When signal Qtm is at the H level, then frequency divider 426 performs counting by 1/60, in combination with NAND gate 434. In this case, since a time unit signal is being applied to counter 424, time counting is performed, and an output signal having a period of one minute is produced by NAND gate 434.

When signal Qtm is at the L level, then due to the output from an inverter 433, counter circuit 426, in combination with NAND gate 432, performs counting by a factor of 1/100. In this case, steps are counted since the input signal to counter 424 corresponds to signal PT1, as explained above. Upon a count of 60, or 100, an output signal is produced by circuit 436 causing counter 426 to be reset to a count of zero, and a carry signal to be input to a counter circuit 428. Counter 428 counts by a factor of 1/10. On a count of 10, an output signal is produced by circuit 440 which resets counter 428 and is applied as a carry input to a counter 430. In a similar manner to counter 426, counter 430 counts by a factor of 1/6, when signal Qtm is at the H level (i.e. when counting time intervals) and by a factor of 1/10 when signal Qtm is at the L level (i.e. when counting numbers of steps). The output signal from circuit 440 increments counter 430 by one, for each count of 10 minutes of of 1000 steps. Thus, counter 430 counts up to either one hour or to 10,000 steps. When such a count is reached, a termination signal from circuit 442 goes to the L level, thereby resetting counter 430 to zero. The inverse of this reset signal, designated as END, goes from the L level to the H level at this time.

A counter circuit 433, and a comparator 444 are utilized for a "repeater" facility, whereby audible signals are generated to indicate elapsed time or numbers of steps, as explained previously. Let us assume that time intervals are being counted by counters 426, 428 and 430, and that the contents of counters 430 are zero. When a count of 10 minutes is attained by counter 428, then the output of circuit 440 goes from the H to the L level, causing count of one to be stored in counter 430.

Prior to this point in time, since the contents of both counter 430 and 433 were zero, the output of comparator circuit 444 was at the H level, so that the $\overline{Q}$ output of data type flip-flop 437 was at the L level. This L level signal, applied to an NAND gate 427, prevents clock pulses (consisting of signal PT1) from being applied to counter 433. When a count of one is stored in counter 430, however, the output of comparator 444 goes to the L level, and the next pulse of signal PT1 (applied to the clock terminal of FF 437) causes the Q output of FF 437 to go to the H level, thereby enabling pulses to be applied to counter 433 through NAND gate 427. This repeater signal input to counter 433 is designated as TSD, and appears at the output of an inverter 429. It consists of pulses of signal PT1. When one of these repeater pulses has been applied to counter 433, so that a count of one is stored in counter 433, then the output of comparator circuit 444 returns to the H level (since the contents of counters 430 and 433 are again in coincidence), so that NAND gate 427 is again inhibited from passing clock pulses to counter 433. Thus, when the first count of ten minutes is stored in counter 430, a single pulse is output as repeater signal TSD. This pulse has the same pulse width as signal PT1.

When a count of 10 is again attained by counter 428, the process described above is repeated. The output of circuit 440, applied through gates 431 and 435, resets the contents of counter 433 to zero, and cause a count of 2 to be stored in counter 430. The Q output of FF 437 again goes to the H level, enabling NAND gate 427. In this case, two repeater pulses must be input to counter 433 before coincidence is established between the contents of counters 430 and 433. Two pulses are therefore produced as signal TSD, which correspond to two consecutive pulses of signal PT1.

In this manner, each time the contents of counter 430 change to a new value, a group of consecutive repeater pulses are produced as signal TDS, with the number of pulses in the group being identical to the new count value in counter 430. Signal TDS is utilized to produce an audible repeater signal comprising audible tone bursts, so that the user is thereby notified of the number of tens of minutes (or 1000's of steps) which have elapsed since the start of an exercise period. This "repeater" facility therefore makes it unnecessary for the user to continually remember to look at the dial of a timepiece, in order to ensure that a predetermined amount of exercise is not exceeded.

It is recommended in some cases that the person undertaking physical exercise should exercise for a predetermined time, of about 12 minutes for example, and then halt the exercise and measure the pulse rate. This is made possible in the present embodiment by a NAND gate 441 in FIG. 21B, the output of which goes to the L level when 12 minutes of exercise have elapsed. A signal Pmark is thereby generated by an inverter 445, at the H level, which causes an audible tone burst to be generated as described later.

When an exercise time of one hour, (or approximately 10,000 steps in the case of step counting) has elapsed, a termination signal END produced by circuit 442 goes to the H level, due to a count of 10 or 6 in counter 430 being detected. Signal END soon afterwards returns to the L level, in response to a signal applied from counter 426 to circuit 442. While signal END is at the H level, signal Pmark from inverter 445 is also at the H level, so that an audible tone burst is generated, indicating that the maximum exercise period has elapsed. When signal END then goes to the L level, signal Popr is reset to the L level, as described later, and operation of the pace timing device is terminated.

At the start of operation, counters 424 and 426, together with counter 433, are reset to a count of zero by a signal Ro, which is a general reset signal. Counter 433 is also reset, through gate 431, by a signal SW ↑ which will be described later.

Figure 21C:
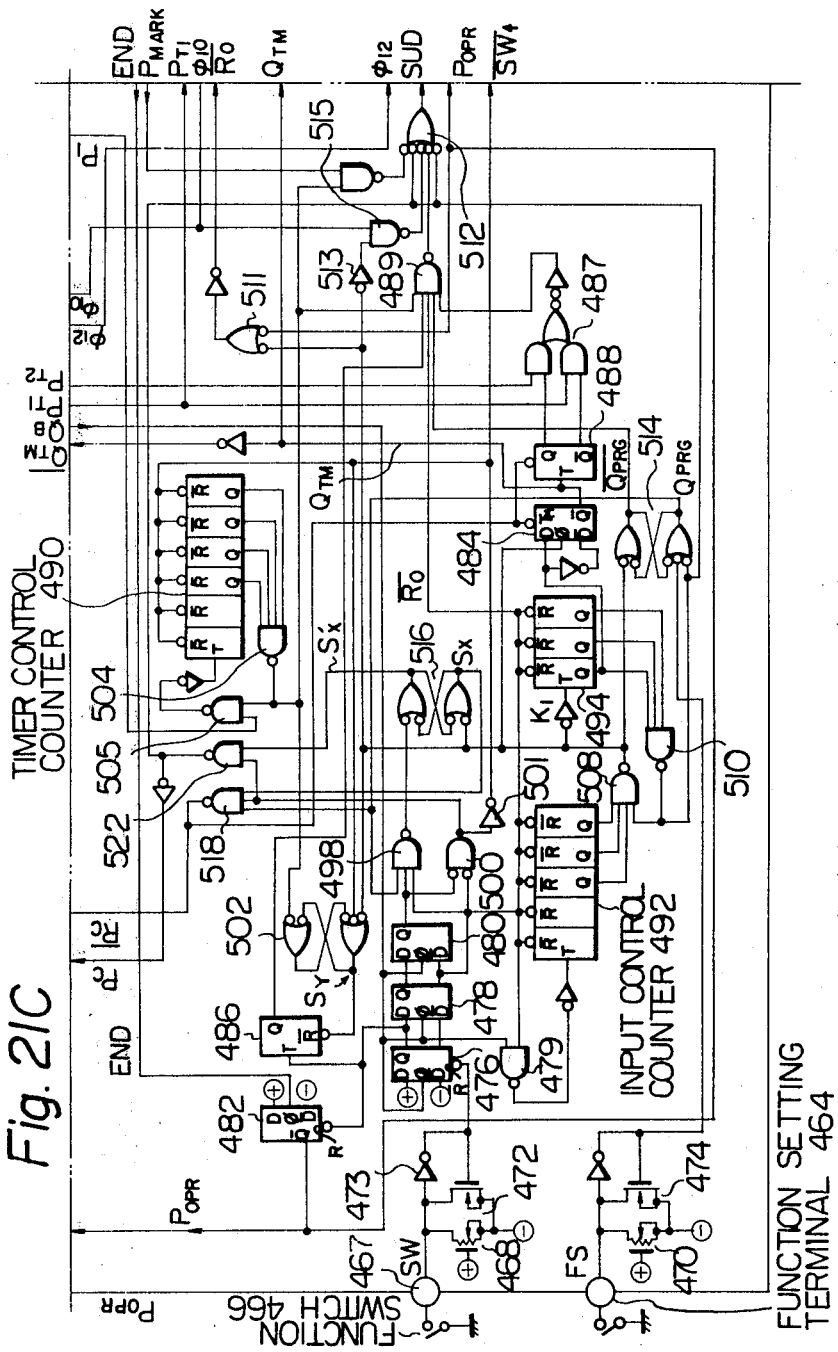

Referring now to FIG. 21C, numeral 466 denotes an operating switch, which is actuated by the user to set various operating conditions of the device, and also to start and stop operation of the device. When switch 466 is open, the corresponding input terminal 467 is held at the L level, by very high value resistor 468 (shown here as a diffusion resistor) and a transistor 472. Due to the L potential applied through resistor 468, the output of an inverter 473 is held at the H level, causing transistor 472 to be in the conducting condition, so that terminal 467 is held at a low impedance level. When switch 466 is actuated, the output of inverter 473 goes to the L level, so that transistor 472 goes to the high impedance condition. In this way, terminal 467 is always maintained in a low impedance condition, without any current being drawn from the battery as a result.

The operations resulting from actuation of switch 466 will be described, first assuming that the device is in the inoperative state. When switch 466 is actuated, an L level signal is applied from inverter 473 to the reset terminal of a data-type flip-flop 476, which is thus reset so that its Q output goes to the L level. This output is applied to the reset terminal of a data type flip-flop 482, which is also thereby reset. The $\overline{Q}$ output of FF 482, designated as an operation enable signal Popr, thereby goes to the H level. When signal Popr is at the H level, operation of the device is enabled, since, as described previously, this signal controls the operation of time-base oscillator circuit 87, in FIG. 21A. Until operation of oscillator 87 begins, control of FF 476 and FF 482 is performed asynchronously by switch 466. Signal Popr also is applied to gates in FIG. 21D which control the generation of audible signals by the device, and when Popr is at the L level, generation of any audible signals is inhibited by these gates (described later).

Shortly after operation of oscillator circuit 87 has been initiated and switch 466 is released, signal $\phi_5$, which is applied to the clock terminal of FF 476, causes the Q output of FF 476 to go to the H level, since an H level potential is always applied to the data terminal of FF 476. Each time operating switch 466 is actuated, the resulting operating signal, comprising a negative-going transition of the output of FF 476, causes a toggle-type flip-flop 486 to be toggled, so that a control signal Qsud produced by FF 486 changes from one logic level to the other.

Data type flip-flops 478 and 480 serve to produce signals which are delayed by a fixed amount relative to changes in the output of FF 476. The $\overline{Q}$ output of FF 478 and the Q output of FF 480 are applied to inputs of a gate 500, which thereby produces an actuation signal comprising a short pulse each time switch 466 is actuated, shortly after the actuation (i.e. closing) begins. The output signal from gate 500 is denoted as SWa.

While function switch 466 is held actuated, the $\overline{Q}$ output of FF 478 remains at the H level, thereby enabling clock pulses $\phi_5$ to pass through an NAND gate 479 to be counted by a counter 492. Clock pulses $\phi_5$ have a frequency of 32 Hz, so that after approximately one second, the outputs from counter 492 which are applied to inputs of a NAND gate 508 cause the output of NAND gate 508 to go to the L level. A flip-flop 514 is thereby reset, so that a programming enable signal Qprg goes to the L level. If function switch 466 continues to be held actuated, then a series of pulses, designated as signal K1, are output by NAND gate 508. This is illustrated in the waveform diagram of FIG. 25. These pulses are applied to a counter 494, the outputs of which are applied to a NAND gate 510. When 7 of the K1 pulses have been counted, the output of NAND gate 510 goes to the L level, inhibiting further input of pulses by gate 508. The L level output of NAND gate 510 causes FF 514 to be set, so that programming enable signal Qprg goes to the H level. The device is thereby set into a programmable condition, in which the user can control the repetition rate of the pace timing signal. The user is notified that this programmable condition has been entered, since an audible tone signal is generated. This is caused by the output of NAND gate 510 being applied to an input of a gate 512, the output of which is a signal designated as SUD. When signal SUD goes to the H level, an audible tone is generated by the circuitry of FIG. 21D, described later.

Figure 25:
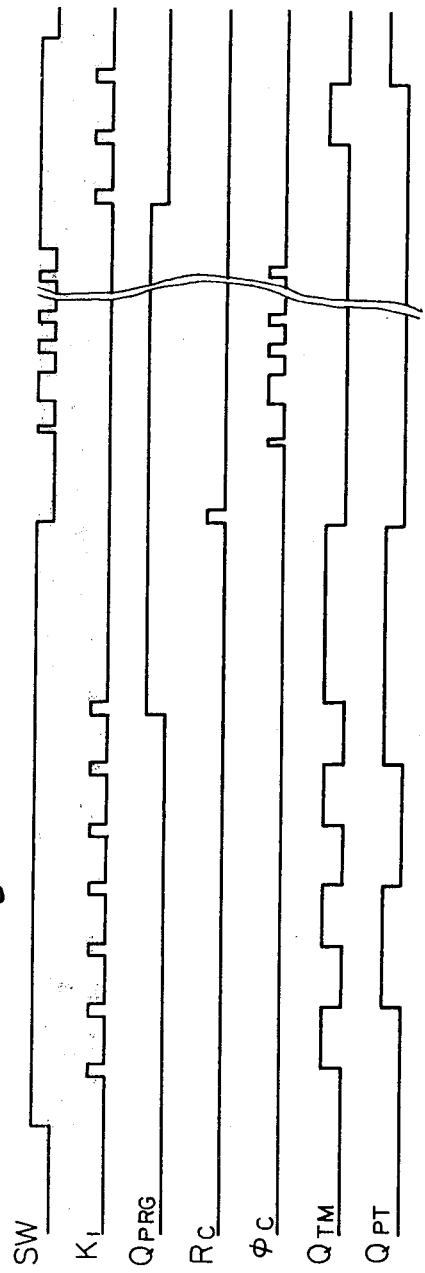
FIG. 25 is a waveform diagram illustrating the manner in which externally actuated switch signals control the operation of the circuit of FIG. 21A to D.

Signal Qprg is applied to an input of a NAND gate 498, which also receives inputs from FF 478 and FF 480. As a result, when function switch 466 is now released, so that switch signal SW goes to the L level as indicated in FIG. 25, a short pulse denoted as SWb is produced by NAND gate 498, which sets a flip-flop 516, thereby causing a signal Sx to go to the H level. Signal Sx is applied to an input of a NAND gate 518, which is thereby enabled to produce a reset signal comprising a short pulse denoted as $\overline{Rc}$, which resets the contents of counter 388 (in FIG. 21A) to zero. As stated previously, the frequency of the pace timing signals is determined by the count value stored in counter 388. NAND gate 522 is enabled at this time, by an H level signal Sx' from flip-flop 516. Subsequently, each time that switch 466 is actuated (for a duration of less than one second), a pulse is produced by NAND gate 522, which is inverted to form signal Pc. This is applied to the clock input of counter 388, so that the user can set the count in counter 388 to any desired value by successively actuating switch 466 for brief periods. When the desired value has been stored in counter 388, then switch 466 is actuated for a duration of more than one second but less than 7 seconds, thereby causing FF 514 to be reset by the output of NAND gate 508, so that signal Oprg returns to the L level. The system is now in the normal (i.e. non-programmable) operating state.

Signal K1 is inverted by inverter 513 and modulated by signal $\phi_{10}$ in a NAND gate 515, the output of which is applied to gate 512. An audible signal, consisting of modulated tone bursts, each corresponding to a pulse of signal K1, is therefore generated, to notify the user that the normal operating state has been restored by actuating switch 466 for more than one second.

Signal K1 is also applied to a gate 511, to generate a reset signal R0, which is used to reset the counter circuits 424, 426, 428 and 430, of FIG. 21B, to zero. Thus, the user can reset the count of time or of a number of steps, contained in these counters, simply by actuating function switch 466 for more than one second.

Numeral 490 denotes a counter circuit which is used to set a limited time duration to the generation of an audible pace timing signal. Each time function switch 466 is actuated, counter 490 is reset by signal $\overline{SWa}$ from an inverter 501. The output of a NAND gate 504 therefore goes to the H level, enabling clock pulses P1 to be applied through a NAND gate 505 to counter 490. Clock pulses P1 have a frequency of 2 Hz. When a count of 60 or more is attained by counter 490, indicating a time lapse of more than 30 seconds, the output of NAND gate 504 goes to the L level, inhibiting NAND gate 505. A flip-flop 502 is thereby set, so that an L level signal is applied to the (inverting) reset terminal of FF 486. Signal Qsud from FF 486 therefore goes to the L level, so that, generation of audible signals due to the output from NAND gate 489 is inhibited. FF 502 is reset by signal SWa each time switch 466 is actuated, so that the user can command the generation of audible pace timing signals for successive 30 second intervals, if desired, simply by actuating function switch 466 when the audible signals are cut off. The user can also inhibit the production of the audible pace timing signals at any time, by actuating function switch 466 for less than one second, thereby causing FF 486 to be toggled, so that signal Qsud goes to the L level. The audible signals can be restored by actuating switch 466 again, for less than one second.

Signal $\overline{SWa}$ is also applied through gate 431 (in FIG. 21B) to reset the contents of counter 433 to zero. Thus, if the user wishes to determine the approximate time which has elapsed since the start of the exercise (when the device is in a time counting mode) or the number of steps performed (when in a step counting mode), it is only necessary to briefly actuate function switch 466, whereupon a succession of pulses will be generated as signal TSD, causing a succession of audible tone bursts to be generated to indicate the approximate number of steps or number of time intervals which have elapsed.

When the maximum count of counter 430 is detected by circuit 442 (in FIG., 21B), then termination signal END goes to the H level and then to the L level. Signal END is applied to the clock terminal of FF 482, so that when the maximum number of steps or time intervals which can be counted by counter 430 has been reached, signal Popr from FF 482 returns to the L level. The operation of the device is thereby terminated, since timebase oscillator 87 is thereby halted.

The manner in which the user selects the various operating conditions of the circuit will now be described, referring to FIG. 21C and the waveforms of FIG. 25. Signal K1 is applied to the clock terminal of a flip-flop 484, and the output of the first stage of counter 494 is applied to the data terminal of FF 484. The output signal produced by FF 484, designated as Qtm, therefore varies with successive K1 pulses as shown in FIG. 25. The function of signal Qtm has been described previously, e.g. when this signal is at the H level, the counter circuits 426, 428 and 430 performs a time interval counting function, while when Qtm is at the L level these counters perform a step counting function. Signal Qtm (from the $\overline{Q}$ output of FF 484) is applied to the T terminal of a toggle-type flip-flop 488, the output of which is designated as Qpt. Signal Qpt therefore changes state with successive negative-going transitions of signal Qtm, as shown. Signal Qpt and its inverse are applied to a selector circuit 487, together with signals PT1 and PT2. When signal Qpt is at the H level, signal PT2 is output by selector circuit 487, while when signal Qpt is at the L level, signal PT1 is output. This output from selector circuit 487 is applied to an input of gate 489, the output of which is applied to gate 512. Thus, when signal Qpt is at the H level, a pace timing signal having a rythm component (due to signal PT2) is produced as explained previously, and when signal Qpt is at the L level, a pace timing signal is produced which is identical in timing to the first frequency signal PT1, i.e. consisting of regularly repeated tone burst without a rythm component.

Thus, if the user actuates switch 466 until a single tone burst is generated (due to signal K1), and then releases the switch, then signal Qtm will be at the H level and signal Qpt at the L level. In this case time intervals will be counted by the counters 426 to 430, and no rythm component will be inserted in the audible pace timing signal. If the user, instead, holds switch 466 actuated until two successive tone bursts of signal K1 have been heard, then releases switch 466, the system will be placed in the condition in which signal Qtm is at the L level and Qpt at the H level, so that an audible pace timing signal having a rythm component is generated, and numbers of steps are counted by counters 426 to 430. The other possible combinations of step/time interval counting and pace timing with/without rythm component can similarly be selected by actuating switch 466 until 3 or 4 successive tone bursts are heard, and then releasing the switch. It will be appreciated that, in this way, a number of functions or modes of operation of the system can be controlled simply by actuatin of a single function switch 466.

A function setting terminal 464 is also provided, whereby the system can be forcibly held in the programmable state without utilizing function switch 466. This terminal is also held at a low impedance condition by means of a high value resistor 470 and a transistor 474, in the same manner as terminal 467. If desired, a switch operable by the user can be coupled to terminal 464, so that the system can be directly set in the programmable state immediately. When terminal 464 is set to the H level, an L level input is applied to set FF 514, so that signal Qprg goes to the H level.

The various signals which control the generation of audible tone signals, such as PT1 or PT2 selected by selector circuit 487, are applied to inputs of gate 512, which performs an OR function with respect to L level signals. Signal K1 is modulated by signal $\phi_{10}$, with a frequency of 102H, Hz, in gate 515, and the resultant signal is applied to gate 512.

Referring now to FIG. 21D, signal SUD from gate 512 is input to NAND gate 451. This gate serves to prevent an audible pace timing signal from being generated while an audible signal indicating an elapsed time or number of steps is being generated, and is controlled by signal TSE. The output of gate 451 is applied through gate 455 to inputs of gates 456 and 457, each of which is enabled when signal Popr is at the H level. Clock signals $\phi_{12}$ and $\overline{\phi}_{12}$ are also input to gates 456 and 457 respectively, as carrier signals, so that gates 456 and 457 function as a modulator circuit. The modulated signals SP1* and SP2* are applied to preamplifier inverters 458 and 459, the outputs of which are applied to drive amplifiers 460 and 461. A miniature loudspeaker 462 is thereby driven in push-pull by output signals SP1 and SP2 from drive amplifiers 460 and 461. When pulses of signal TSD are produced, to provide audible signals indicating a number of steps or elapsed time through the "repeater" facility, these pulses are applied through NAND gate 453, in which they are modulated by signal $\phi_{10}$, and the modulated signal is applied through gate 455 to the drive amplifier circuit. It will be seen that signals K1 and TSD are modulated twice, by signals $\phi_{10}$ and $\phi_{12}$, before being applied to loudspeaker 462. This will be explained in the following.

Figure 24A:
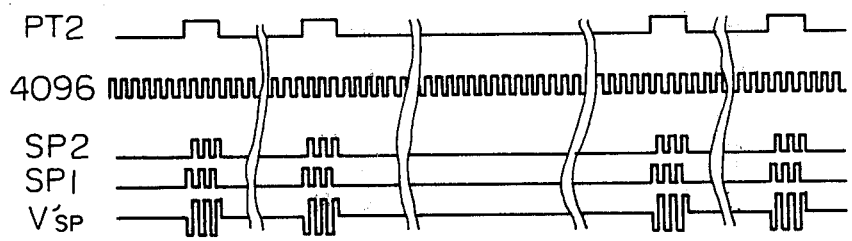
FIG. 24A, 24B and 24C are waveform diagrams illustrating the manner in which pace signals having a predetermined rythm are produced by the circuit of FIG. 21A to D.

To attain maximum efficiency of sound generation by an acoustic device such as an electromagnetic loudspeaker, the resonance frequency of the acoustic device should be identical to the carrier frequency of the modulated pulses applied to the acoustic device. In this embodiment, the carrier frequency is 4096 Hz. FIG. 24A shows the waveforms of signals SP1 and SP2 when signal PT2 is modulated to produce an audible pace timing signal having a rythm component. As indicated by the dotted lines, pairs of pulses are periodically omitted from signal PT2. Signal Vsp denotes the voltage appearing across the drive coil of loudspeaker 462.

Figure 24B:
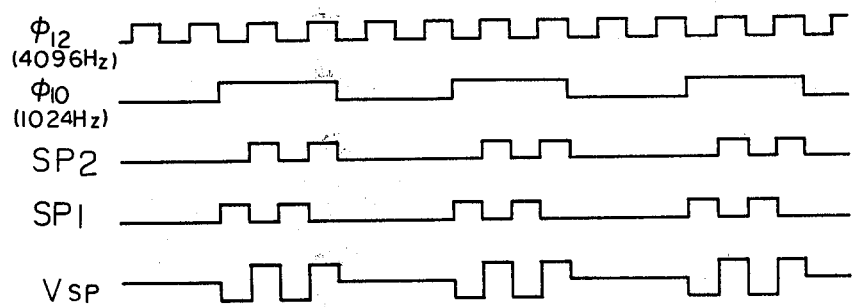
Figure 24C:
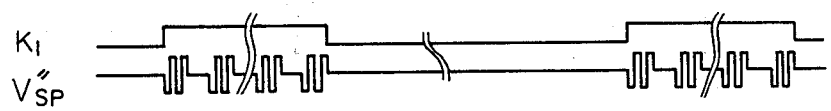

In order to provide audible tone signals of distincitively different character from those provided by the signals shown in FIG. 24A, modulation both at the carrier frequency of 4096 Hz, and at a frequency which is a submultiple of the carrier frequency can be performed. This is illustrated in FIG. 24B, in which the signal Vsp resulting from modulation by both signal $\phi_{12}$ and signal $\phi_{10}$ is shown. This enables tones of different character to be generated, while maintaining a high efficiency of operation of loudspeaker 462. The resulting waveform of signal Vsp when signal K1 is modulated both at 1024 and at 4096 Hz is shown in FIG. 24C. A drive waveform of similar shape is applied to loudspeaker 462 when pulses of signal TSD are generated, to audibly indicate a number of steps or elapsed time, by the repeater facility.

A pace timing device as described above can be constructed of only six parts, excluding the case, namely, a pushbutton switch for function switch 466, a silver oxide cell for battery 463, an electromagnetic loudspeaker for acoustic device 462, a commercially available low-cost quartz crystal vibrator for vibrator element 370, and with all of the circuitry provided on a single CMOS integrated circuit. It is not necessary to provide a power ON/Off switch, since the circuit can be designed such that when the device is in the inoperative condition (signal Popr at the L level9 all of the transistors in the circuit are biased to the cut-off state. In this case, the leakage current in the inoperative state can be held to less than $1 \times 1^{-7}$ A. This is sufficiently small that it is unnecessary to provide a power ON/OFF switch.

Figure 26:
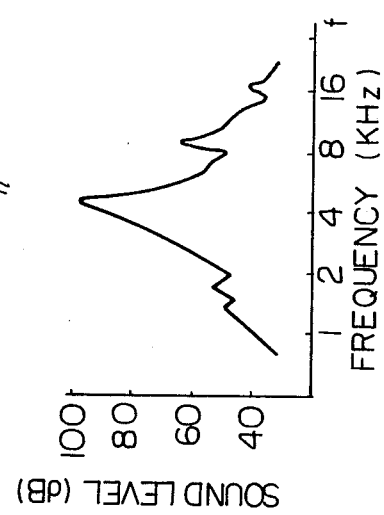
FIG. 26 is a graph showing the frequency characteristics of a miniature loudspeaker suitable for use as an acoustic device in a pace setting device according to the present invention.

FIG. 26 is a graph showing the relationship between output sound level and frequency, for a miniature electromagnetic loudspeaker utilized in the embodiment of the present invention described above. The loudspeaker impedance was 100 ohms, and the drive voltage 3V peak to peak. A sharp resonance characteristic is indicated. When the loudspeaker is driven at a frequency close to the resonant frequency, high efficiency is obtained, and the resulting sound is pleasing and does not tend to be irritating.

Figure 27B:
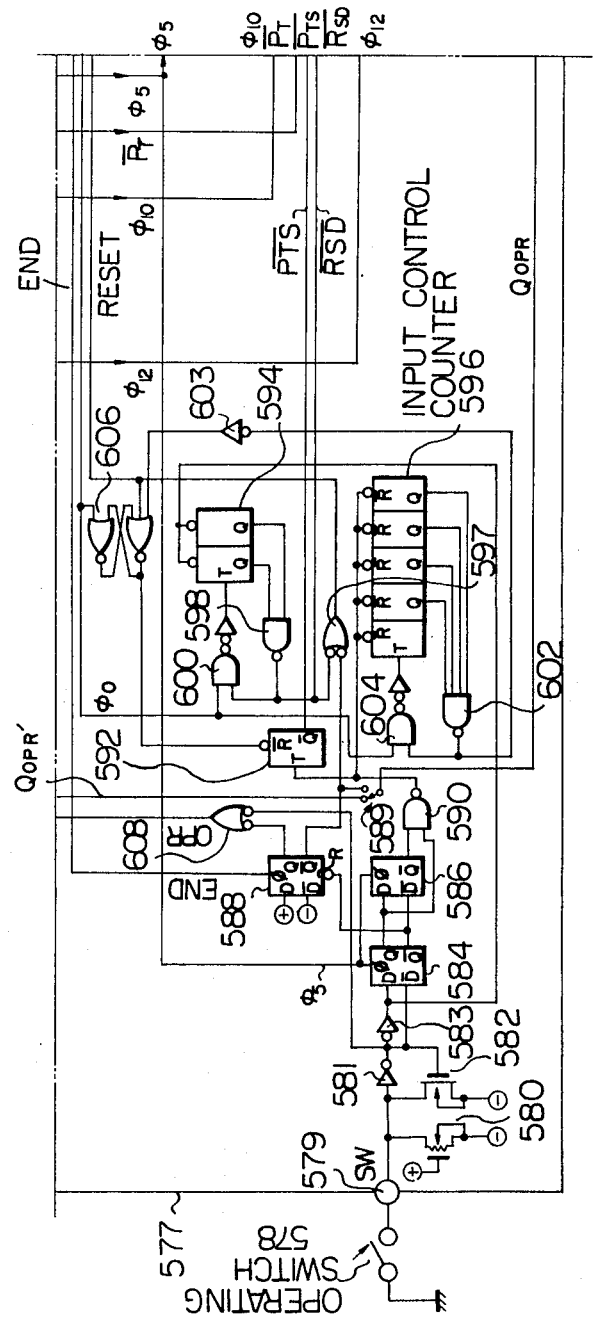
Figure 27C:
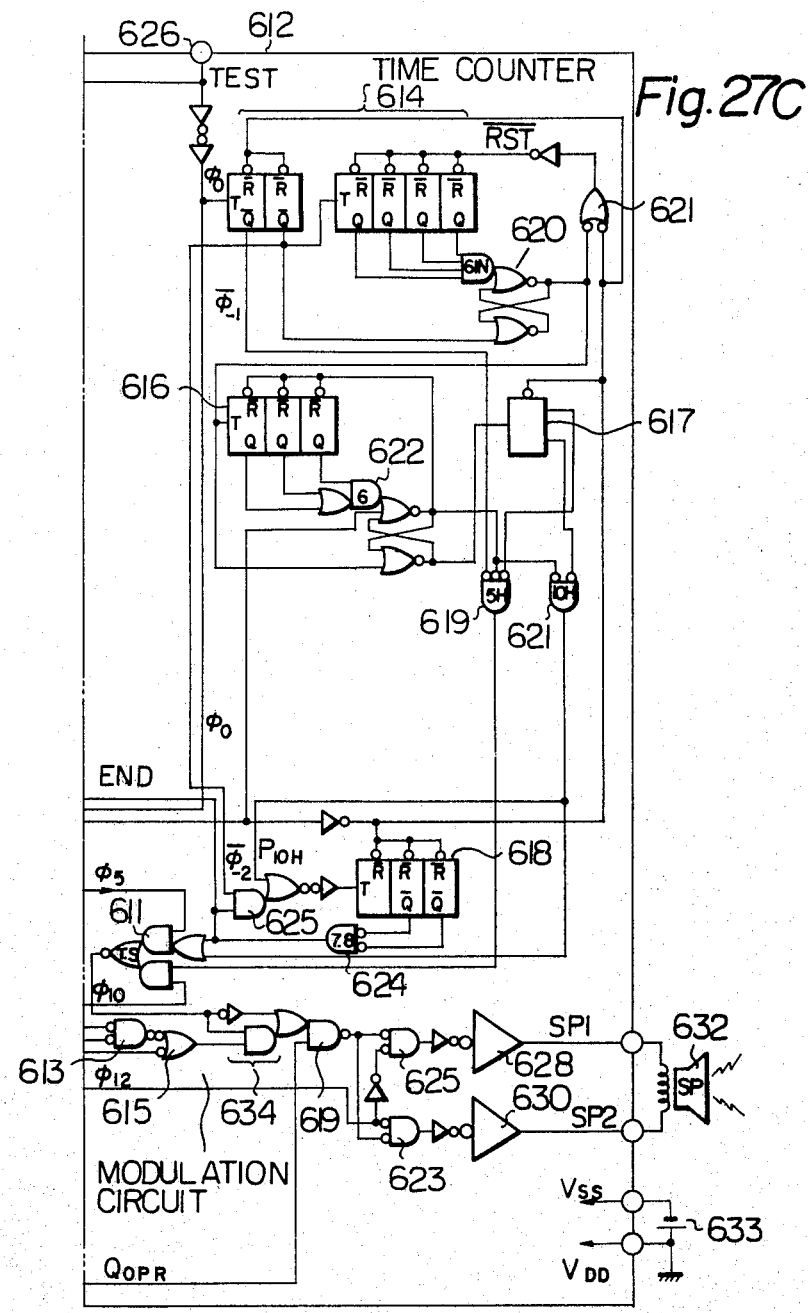

Another detailed embodiment of a pace timing device according to the present invention is shown in FIG. 27A to 27C. This embodiment is somewhat less complex than that of FIG. 21A to 21D, and is not provided with a repeater facility for indication of elapsed time or numbers of steps. However an audible indication is given at the end of each 5 minute time interval following the start of an exercise period. This embodiment also differs from that of FIG. 21A to 21D in that a digital switch, providing binary code combinations directly, is used to input and memorize pace timing frequency information, rather than an electronic counter circuit. Referring first to FIG. 27A, a quartz crystal vibrator 530 is coupled to terminals of an oscillator circuit 532, to form a timebase oscillator having a frequency of $2^{15}$ Hz. Oscillation is controlled by a control gate 570. When an operation enable signal denoted OPR is at the H level potential, then oscillation is enabled, while when OPR is at the L level, oscillation is inhibited, and the entire circuit is made inoperative, so that power consumption becomes negligible. The timebase signal is applied through a buffer amplifier 558 to the input of a frequency divider circuit 536, which thereby produces various output signals $\phi_{14}$, $\phi_{13}$, $Q_{12}$, ... and so on, having frequencies of $2^{14}$, $2^{13}$, $2^{12}$, ... etc.

Figure 28:
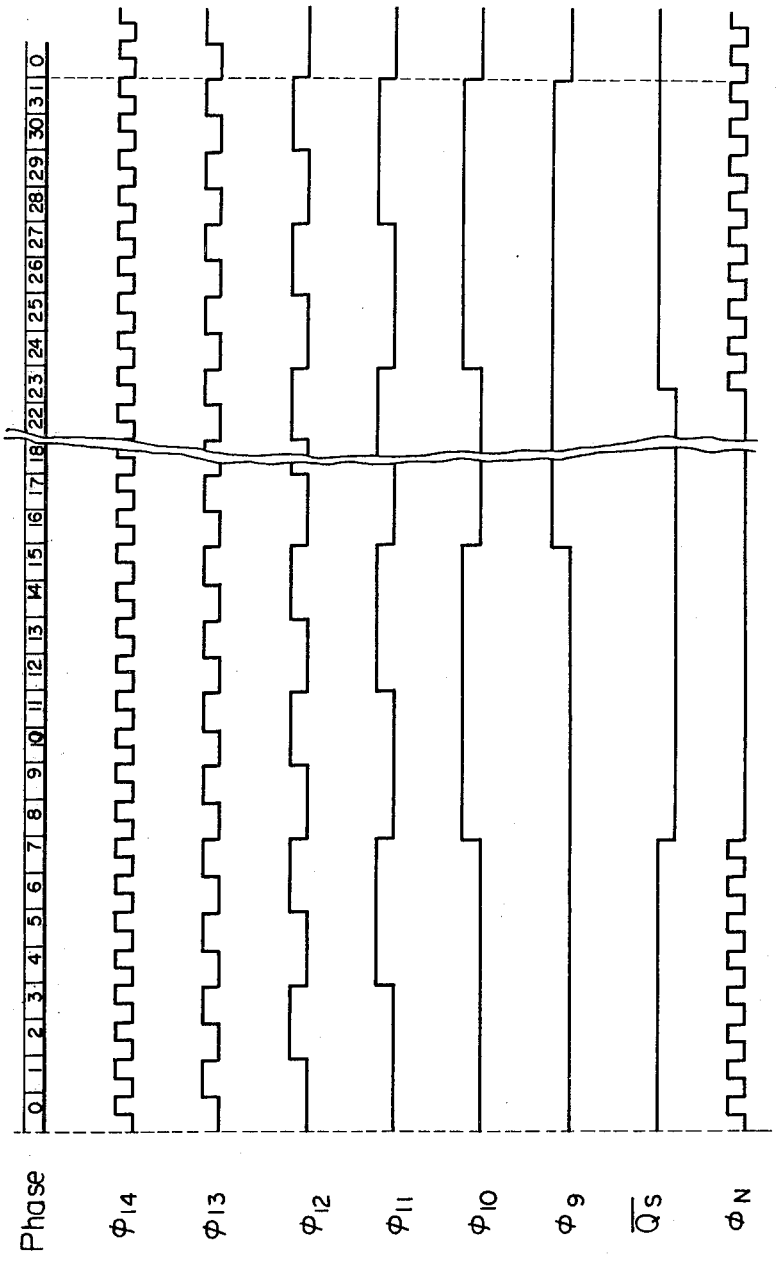
FIG. 28 is a waveform diagram illustrating the operation of the circuit of FIG. 27A to 27C.

Numeral 550 denotes a digital switch, which is operated by the user to produce various binary code signal combinations on input terminals 551. These input signals are applied through buffer amplifiers 556 to inputs of Exclusive-OR gates 566 of a comparator circuit, in which they are compared with outputs $\phi_{10}$ to $\phi_{13}$ of frequency divider 536. The outputs of gates 566 are applied to inputs of a NOR gate 546, together with the inverse of signal $\phi_{14}$ and with signal $\phi_9$. Output $\phi_{14}$ of frequency divider 536, together with $\phi_9$, $\phi_{11}$, $100_{12}$, and $\phi_{13}$ are input to a NAND gate 544, the output of which is coupled to the reset terminal of a data type flip-flop 570. The $\overline{Q}$ output of FF 570, together with signal $\phi_{14}$, is applied to a NAND gate 548, the output of which is applied to a 1/12 counter circuit 542. The output of counter circuit 542 is applied to a 1/28 counter 540, outputs from which are applied to a NAND gate 576. The output of NAND gate 576, denoted Pt, is a signal which designates the repetition frequency of an audible pace timing signal produced by the device. The way in which signal Pt is produced an its frequency controlled will now be described, with reference to the waveform diagram of FIG. 28. In FIG. 28, 32 successive pulses of signal $\phi_{14}$ are numbered successively from 0 to 31. When a count of 23 in frequency divider 536 is detected by NAND gate 544, the output of this gate goes to the L level, thereby resetting FF 570, so that output Qs from FF 570 goes from the L level to the H level. NAND gate 548 is thereby enabled to pass signal $\phi_{14}$, and the output pulses from NAND gate 548 are counted by counter circuit 542, the output of which is denote as $\phi_{7N}$ in FIG. 27A and FIG. 28. The notation $\phi_{jN}$ designates a signal of frequency $2^j$, where j=0, ±1, ±2, ... and N denotes the numeric value of the binary bode combination set by digital switch 550, if N is set to 120. In general, the frequency of a signal designated as $\phi_{jN}2^j \times N/120$ Hz, where N is in steps per minute.

When the binary code combination set by digital switch 550 is detected as being identical to the contents of stages $Q_{10}$ to $Q_{13}$ of frequency divider 536, then the output of gate 546 goes from the H level to the L level, causing the $\overline{Q}s$ output of FF 570 to go to the L level, since the data terminal of FF 570 is connected to the H level. NAND gate 548 is thereby inhibited, so that output of pulses $\phi_{7N}$ is halted, as indicated in FIG. 28. In order to ensure reliable detection of coincidence between the contents of frequency divider 536 and the code combination of digital switch 550, coincidence detection is performed when signal $\phi_{14}$ goes to the H level, since this signal is higher in frequency than the highest frequency signal for which coincidence detection is performed, namely $\phi_{13}$.

The output signal from NAND gate 548, designated as $\phi_N$, has a frequency of $2^9 \times (10+1)$ Hz. This signal is frequency divided by counter 542 which produces an output signal $\phi_{9N}$. This is input to a frequency divider 540, and outputs $\phi_{3N}$, $\phi_{2N}$, and $\phi_{1N}$ from frequency divider 540 are applied to inputs of a NAND gate 576. The outout of NAND gate 576, designated as $\overline{Pt}$. If the input applied to a function control terminal 560 is held at the H level, so that the output of an OR gate 579 is held at the H level, then signal $\overline{Pt}$ is the first frequency signal, i.e. a signal which determines the frequency of a regularly repeated audible pace timing signal. However if the function terminal 560 is held at the L level, then the output from OR gate 579, applied to an input of NAND gate 576, is controlled by the output from the second stage of a counter circuit 574. Counter 574 is a two-stage counter which receives signal $\phi_{1N}$. Thus, if function terminal 560 is held at the L level, then signal $\overline{Pt}$ acquires a rythm component, i.e. successive pairs of pulses are alternately omitted, as has been explained with respect to other embodiments hereinabove.

The frequency of signal $\phi_N$, produced by NAND gate 548, changes from 100 to 190 pulses/second as the value of N (i.e. the numeric value which is set by digital switch 550) changes from 0 to 9, while the frequency of signal $\phi_N$ changes from 100 to 290 pulses/second as the value of N is changed from 0 to 19. In general, the frequency of $\phi_N$ is given by $2^9 \times (10+N)$ Hz. Nine pulses of signal $\phi_N$ are passed prior to the H to L level transition of signal $\phi_9$, and (N+1) pulses are passed after that transition. Thus, due to the 1/12 frequency division in counter 542 and $\frac{1}{2^8}$ frequency division in counter 540, the frequency of signal $\overline{Pt}$ of 2 Hz is obtained, if N is 12, for example.

A time counter circuit 538 counts signal $\phi_9$ from frequency divider 536, to produce a time unit signal $\phi_0$.

Numeral 554 indicates an input circuit, whereby any of the input terminals of switch 550, or the function terminal 560, is held in a low impedance condition, at the L level potential, if the terminal is not set to the H level during operation of the device. This serves to ensure higher reliability, by reducing the possibility of noise being picked up at the input terminals. The gates composing the input circuit for function terminal 560 are denoted by numerals 552 and 553, by way of example. If terminal 560 is left open circuit, with the device in operation, then a signal OPR, which is always at the H level during operation of the circuitry, causes the output of gate 552 to go to the L level, in conjunction with the output of gate 553. Gates 552 and 554 are connected to form a flip-flop, which is repetitively reset by a signal $\overline{P}_{8N}$ applied to an input of gate 553. This signal has a repetition rate of one pulse in $\frac{1}{8}$ seconds, and a pulse width of about 2 milliseconds. Thus, the output of gate 552 is held at the L level potential, so long as terminal 560 is left disconnected. If terminal 560 is connected to the H level, however, then the output of gate 552 is forcibly held at the H level also. It is possible to increase the time periods between resetting of the input circuits by increasing the period of the resetting signal to the order of one second, or several seconds. The power consumed by the input circuits can also be reduced by reducing the pulse width of the resetting signal (i.e. the time for which the resetting signal is at the L level) to the order of several tens of microseconds. This would also reduce the possibility of pickup of induced noise.

FIG. 27B shows the input circuit, by which the user controls various functions. An operating switch 578 is coupled to an input terminal 579, which is held at the L logic level, in a low impedance condition, by means of a high resistance 580 and a field effect transistor 572. Such an arrangement has been described previously, with regard to the embodiment of FIG. 21. Terminal 579 is coupled through two inverters to the data terminal of a flip-flop 586, and is coupled through a single inverter 581 to an input of a gate 608. The output of gate 608 is designated as OPR, which is the operation enable signal controlling the initiation of operation of oscillator circuit 532 (in FIG. 27A). Thus, when switch 579 is actuated, the output of inverter 608 goes to the L level, causing signal OPR to go to the H level, so that oscillation begins. Clock signal $\phi_5$ is thereby generated by frequency divider 538, which is applied to the clock terminal of FF 584. The first H level to L level transition of signal $\phi_5$ causes the Q output of FF 584 to go to the H level. This output, together with the $\overline{Q}$ output of FF 586 is applied to inputs of a NAND gate 590, so that a short-duration negative-going pulse is produced by NAND gate 590 immediately following actuation of switch 578. This pulse is applied to the T terminal of a toggle-type flip-flop 592, and also to the reset terminals of a counter circuit 596. Thus, each time switch 578 is actuated, the $\overline{Q}$ output of FF 592, which is designated as signal $\overline{PTS}$, goes from the H to L level or vice versa. When signal $\overline{PTS}$ is at the L level, then generation of audible pace timing signals is enabled, and when at the H level generation is inhibited, as described hereinafter. The user can thus control the production of audible pace timing signals, by briefly actuating switch 577.

When the circuit is in the inoperative condition, then a data type flip-flop 588 is in the set state, so that the Q output of this flip-flop is at the H level. When the user actuates switch 578 in this condition, then, as described above, the Q output of FF 584 goes to the H level, and so the $\overline{Q}$ output of FF 584, which is coupled to the reset terminal of FF 588, goes to the L level. FF 588 is thereby reset, so that the Q output of FF 588 applies an L level input to gate 608. Thus, FF 588 serves to memorize a switch actuation which initiates operation of the circuit, by maintaining signal OPR at the H level after switch 578 is released (i.e. opened).

When switch 578 is actuated, the output of an inverter 583 goes to the H level. An input control counter circuit 594, which is normally held in the reset condition by an L level signal applied from inverter 583, is thereby enabled to count signal $\phi_0$, which is applied through a NAND gate 600. Signal $\phi_0$ is a unit time signal having a frequency of 1 Hz, so that the output of a NAND gate 598 goes to the L level if switch 578 is held actuated for 3 seconds or longer, i.e. until a count of 3 is attained by counter 594. When a count of 3 is detected, the L level output of NAND gate 598 inhibits further input of clock pulses by NAND gate 600 to counter 594, and causes the output of a gate 597 to go to the H level. The H level condition of the output from gate 597, which is designated as signal RESET, causes a flip-flop 606 to be reset, thereby applying an L level signal to the reset terminal of FF 592, thereby inhibiting the generation of audible pace timing signals. The RESET signal is also used to reset various timekeeping counter circuits, as described hereinafter.

Numeral 596 denotes a timer control counter circuit, which cuts off the generation of an audible pace timing signal after an interval of 30 seconds following initiation of operation of the circuit. When switch 578 is actuated, the short pulse generated by NAND gate 590 resets counter 596 to zero, and so counting of clock signal $\phi_0$, applied through a NAND gate 604, begins. When a count of 30 or more is detected by NAND gate 602, then the output of this gate goes to the L level, thereby inhibiting further input of clock pulses to counter 596. The output of NAND gate 602 is applied, through an inverter 603, to FF 606, so that when the 30 seconds time interval has elapsed, the output of FF 606 applied to the reset terminal of FF 592 goes to the L level, thus resetting FF 592 and inhibiting the generation of an audible pace timing signal. The user can cause the audible pace timing signal to be generated for another 30 seconds, if required, simply by briefly actuating switch 578 once more.

The $\overline{Q}$ output of FF 588, designated as signal Qopr, is held at the H level while the device is in operation, i.e. while signal OPR is at the H level. The L level condition of signal Qopr is used to inhibit the generation of all audible signals by the device, as described hereinafter.

Referring now to FIG. 27C, the operation of the time counter and output circuits will now be described. A signal $\phi_0$, having a frequency of 1 Hz, is applied to the input of a time counter circuit 614, which counts the seconds of time. A circuit 620, comprising a detection gate and flip-flop, produces an output signal at the L level when a count of 60 or more (i.e. one minute) is detected. This signal is applied through a gate 621 and an inverter to produce a signal $\overline{RST}$, which resets counter 614. The output of circuit 620 is also applied to the clock input terminal of a counter 616, which counts the minutes of time in combine action with a counter 617. A detection circuit 622 detects a count of 6 or more in counter 616, and accordingly resets counter 616 and applies an L level input to a 5-minute detection gate 619. The Q output of counter 617 and a signal $\overline{\phi}_{-1}$ are also applied to 5-minute gate 619, the output of which goes to the H level each time an interval of 5 minutes has elapsed, thereby producing a 5 minute time marker signal. Similarly, the output of a 10-minute detection gate 621 goes to the H level each time an interval of 10 minutes has elapsed, for a predetermined time, as a 10-minute time marker signal. The output of 10-minutes gate 621 is applied to the clock input of an hours counter 618, the final two output stages of which are coupled to inputs of a gate 624. When a count of more than 6 is detected by gate 624, its output goes to the H level. A gate 625 is thereby enabled to apply a signal $\phi_{-2}$ to the clock input terminal of hours counter 618, so that the count held therein is rapidly changed. The output of gate 624 therefore returns to the L level. The output from gate 624 is denoted as the END signal, and is applied to the clock input terminal of FF 588 (in FIG. 27A). Thus, when a time period of one hour has elapsed from the initiation of operation of the pace timing device, an H level to L level transition of signal END occurs, thereby causing the Q output of FF 588 to go to the H level, since the data input terminal of FF 588 is connected to the H level. Signal OPR therby is forced to the L level, so that oscillation by oscillator 532 is halted, and the pace timing device becomes inoperative.

In the above description, it has been assumed that signal Qopr is obtained from FF 588. However, it is also possible to utilize a signal OPR', produced by a NAND gate and inverter 557 in FIG. 27A, as signal Qopr. This is indicated by a changeover link arrangement 589 shown in FIG. 27B. When the device is in the inoperative condition, so that signal OPR is at the L level, the outputs of all of the NAND gates of input circuit 554 (FIG. 27A) are held at the H level. All of the inputs applied to a NAND gate 555 are therefore at the H level, so that the output of NAND gate 555, and hence the output signal OPR' from NAND gate - inverter combination 557, is at the L level. When signal OPR is at the H level, it will be apparent that signal OPR' will also be at the H level. Signal OPR' can thus be used as signal Qopr, to inhibit the output of all audible signals by the device while the inoperative condition is in force. Signal Qopr is applied to an input of a NAND gate 619 (FIG. 27C), to control the passage of various signals through gate 619.

Signal $\overline{Pt}$ is input to a gate 613 which is controlled by signal $\overline{PTS}$ from FF 592, so that the generation of audible pace timing signals is controlled by signal $\overline{PTS}$. The output of gate 613 is applied through gate 615 and a gate circuit 634. Time marker signals from the 10-minute and hour detection circuits 621 and 624 are applied to a modulator circuit 611, to be modulated by clock signal $\phi_5$. Signals from 5-minute detection gate 619 are modulated by signal $\phi_{10}$. The modulated time marker signals thus produced are applied through gate circuit 634 to gates 623 and 625, to be modulated once more by clock signal $\phi_{12}$. It will be seen that pace timing signal $\overline{Pt}$ is modulated once, by signal $\phi_{12}$, while the time marker signals indicating the completion of 5 minute, 10 minute and one hour time intervals are modulated twice, by signals $\phi_{12}$ and $\phi_5$ in the case of the ten minute and one-hour indication signals, and by signals $\phi_{12}$ and $\phi_{100}$ in the case of the 5 minute indication signals. As explained previously, in relation to the embodiment of FIG. 21A to 21C, such double modulation enables audible tones of distinctively different characteristics to be produced. The user is thereby notified of the lapse of 5 minute, 10 minute and one hour time intervals in a clear and distinctive manner, by audible time marker signals which are different from those of the pace timing signal.

Since signal $\phi_{12}$ is applied in normal and inverted forms to gates 623 and 625 respectively, push-pull input signals are applied through buffer inverters to driver amplifiers 628 and 630, to drive an electromagnetic loudspeaker 632.

All components of the above embodiment are contained upon a single integrated circuit chip, other than operating switch 578, digital switch 550, quartz crystal vibrator 530, loudspeaker 632 and battery 633. Function terminal 560 may be preset to the H or L level potential, to enable or inhibit a rythm component in the pace timing signal, or can be coupled to another operating switch, to be controlled by the user.

A test terminal 626 is provided, whereby a signal of relatively high frequency can be applied to the timekeepings counters 612, 614 etc. This enables testing to be performed rapidly, since a signal of higher frequency than $\phi_0$ can be utilized.

Normally, once operation of the circuit has been initiated, it will continue up to a maximum duration of one hour, whereupon the END signal is produced by gate 624 to halt operation of the circuit. However, at any time during operation, the user can reset counters 614, 616 and 618 to a count of zero, by actuating switch 578 for three seconds or longer, so that signal $\overline{RSD}$ is produced by gate 598. Operation will then continue for a further period of one hour, until the END signal is generated.

It should be noted that although a digital switch providing binary code combinations of signals is utilized in the embodiment described above, some other form of switch may be utilized. However a switch such as that used in the described embodiment, by providing input signals in the form of code combinations, reduces the number of connections which must be established between the switch and the integrated circuit chip.

It should also be noted that various simplifications of the embodiments of FIG. 27A to 27C may be envisaged. For example, input circuit 554 (FIG. 27A) can be simplified by replacing the NAND gates of this circuit by inverters, and by inverting signals OPR to apply a signal $\overline{OPR}$ as an input to NAND gate 565.

The circuitry of the above embodiment is formed of CMOS field effect transistors on a silicon integrated circuit chip. Battery 633 is a 1.58 V silver oxide cell. The current consumption of the device when in the inoperative condition (i.e. signal OPR at the L level) is less than 100 mA, and ranges from 0.5 to 1.0 $\mu$A approximately, when the electromagnetic loudspeaker 632 is not being driven. The current drawn when the loudspeaker is being driven is not more than 0.8 mA, for a 100 ohm loudspeaker impedance and a drive signal frequency of 4 kHz. The drive signal waveforms applied to loudspeaker 632 are as discussed previously with respect to the embodiment of FIGS. 21A to 21D, and illustrated in FIGS. 24A, 24B and 24C.

Figure 29A:
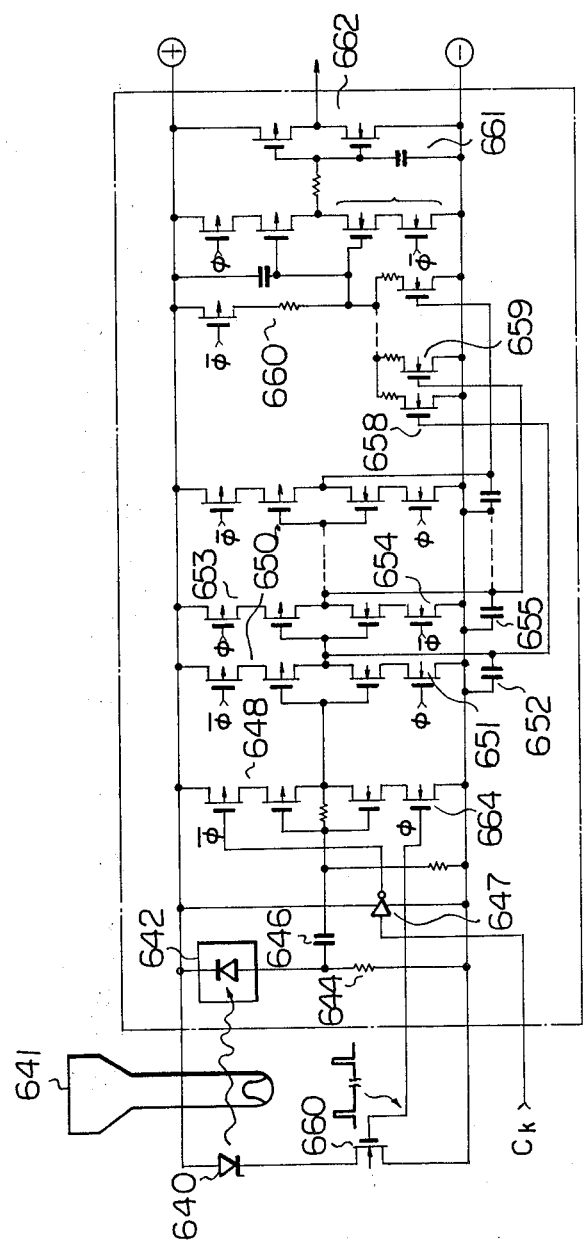
FIG. 29A is a circuit diagram of a pulse rate detection and amplifier system for use with a pace timing device according to the present invention.

FIG. 29 shows the circuit of an embodiment of a pulse rate measurement system, for use with a pace time setting device according to the present invention. In this system the variation in light transmission through the flesh of the user due to changes in the blood vessels caused by the user's pulse are measured. These changes in the blood vessels cause the amount of light dispersed in passing through the flesh to be varied at a frequency which is identical to the pulse rate of the user. In order to minimize power consumption by the pulse rate measurement system, measurement is performed on a periodic basis, as will be described. Numeral 640 denotes a light emitting element, consisting of a junction semiconductor device such as a gallium arsenic, gallium phosphor or gallium aluminum diode, which emits light in the range between the visible and the infrared wavelengths. This light emitting element is connected in series with a transistor 660, to the gate of which is applied an activation signal, comprising a train of clock pulses Ck. Each time a positive-going clock pulse Ck is applied to the gate, transistor 660 conducts, causing lights to be emitted by element 640. This light passes through a part of the user's flesh or skin, as indicated by numeral 641, and that part of the light which is not dispersed or reflected thereby falls on a photoelectric detection element 642, which is a semiconductor element such as a silicon, germanium or lead sulphide diode, is reverse biased by means of a resistor 644. Changes in the voltage across resistor 644 due to light falling upon detection element 642 are applied through a DC blocking capacitor 646 to the first stage of an amplifier circuit. This is designed such as to be only operative for a short time interval while an activation pulse is being applied to the gate of transistor 660, so that light is being emitted by element 640. It has been found that the duration of the activation pulses which drive transistor 660 should be of the order of 30 microseconds, with a repetition frequency which is substantially higher than the maximum pulse rate to be measured, say, above 10 Hz. Pulses of a detection monitor signals, comprising a train of pulses synchronized with the activation signal pulses, switch the amplifier circuit into an operative condition. These consist of the clock pulses Ck, and the inverse, $\overline{Ck}$, which is produced by means of an inverter 647. The first stage of the amplifier is controlled by switching transistors 664 and 648, which are set into the conducting condition when signals Ck and $\overline{Ck}$ to the H level and L level, respectively. The next stage of the amplifier is controlled by switching transistors 650 and 652, which are switched into conduction when signals Ck and $\overline{Ck}$ go to the H and L levels respectively. When the second stage is switched off (i.e. transistors 650 and 652 become non-conducting), the output voltage of the second stage is stored as a charge on a small-value capacitor 652. The switching transistors 653 and 655 which control the third stage of the amplifier become conducting when signals go the the L and H levels respectively, and the amplified output from the third stage is stored in capacitor 655 when this stage becomes inoperative. The fourth stage of the amplifier is switched into operation when signals Ck and $\overline{Ck}$ go to the H and L levels respectively. In this way, successive amplifier stages are switched into operation in alternate phases of clock signal Ck, and each amplifier amplifies the voltage of the storage capacitor of the preceding stage. In this way, a very high level of amplification can be obtained with stability and simplicity of design. The outputs of the various stages are summed by means of transistors 658, 659, etc, each of which is connected through a resistor to an averaging amplifier 660. The output of averaging amplifier 660 appears across capacitor 661, as a voltage which varies in synchronism with the pulse rate of the user, and this voltage is taken out through an output amplifier 662. The pulse rate signal thus produced can be measured and displayed in digital form or in analog form, and can also be used to cause an alarm warning to be sounded when a predetermined maximum pulse rate is exceeded, or to cause the user to be warned in some fashion that the rate of exercise is unsuitable.

In order to obtain maximum signal/noise ratio in the circuit of FIG. 29, it is preferable to cause each of the stages of the amplifier to be made operative immediately after light emission by element 640 has begun, and to be cut off before the light emission has ceased. For simplicity of description, means for achieving this are not shown in FIG. 29. The duration for which light emitting element 640 is driven by the clock pulses will depend upon the rise and fall times of the particular type of element employed, and may also depend upon the frequency response of transistor 660 which drives the element. A laser diode, which has a high efficiency, may be used as light emitting element 640.

The range of wavelengths to which the photoelectric detection element 642 is sensitive should be made as close as possible to the range of wavelengths of light emitting by element 640. It is also possible to modulate the light produced by element 640, and to perform demodulation of the received electrical signals in synchronism with this modulation.

To improve the signal/noise ratio by reducing the effects of ambient light changes, an optical filter may be inserted in the light path between elements 640 and 642. Also, either electrical connection (between element 642 and the amplifier circuit) or optical connection by optical fiber (between the user's skin and photoelectric detection element 642) may be employed.

A photoelectric detection element of high response speed is obtained by using a silicon PIN diode, between ordinary silicon or germanium diodes offer the advantage of lower cost. Cadmium sulfide or lead sulfide elements offer high sensitivity, and in the case of lead sulfide this is particularly true at the longer wavelengths of light.

FIG. 29B shows a cross-sectional view of a rate detection unit 670 for use with a circuit such as that of FIG. 29 to form a pulse rate detection system. A case 671 is provided with openings 682 and 684 in which are fixed light emitting element 640 and photoelectric detection element 642, which are separated by a nontransparent bridge portion 672. Electrical connections to elements 640 and 642 are provided by leads 686 and 688. In use, the top portion of the unit is pressed into the user's skin, so that light can reach photoelectric detection element 642 from light emitting 640 only by passing through the skin of the user. The degree of light transmission varies periodically, in synchronism with the pulse rate of the user, due to changes in the various blood vessels situated between the light emitting and receiving elements 604 and 642.

FIG. 29C shows the external appearance of a pace timing device according to the present invention which is equipped with a pulse rate measurement system. The circuitry, battery, etc, are contained in a case 678 which contains a display area 674 in which the pulse rate or pace timing frequency is displayed. The case is mounted on the user's wrist by means of a strap 676, which has an extension 672 carrying a ring 671 upon which is mounted the pulse rate detection unit 670 shown in FIG. 29B. The device is attached to the user's hand as shown in FIG. 29D. In order to bring the pulse rate detection unit 670 fully into contact with the user's skin, the fist is clenched as shown in FIG. 29E.

Openings 682 and 684 in pulse rate detection unit 670 may be filled with a transparent substance. Alternatively, either or both of elements 640 and 642 may be accommodated within the body of the pace timing device 674, and connected to the pulse rate detection unit 670 by means of optical fiber.

It has been found that the user can adjust the force applied between the pulse rate detection unit 670 and the skin by the degree of force employed in making a fist, such as to ensure reliable detection of the pulse rate irrespective of the particular bodily characteristics of the user. When this is done, also, external light is shielded from the photoelectric detection element 642, by the construction of case 671 of the pulse rate detection unit.

Figure 30:
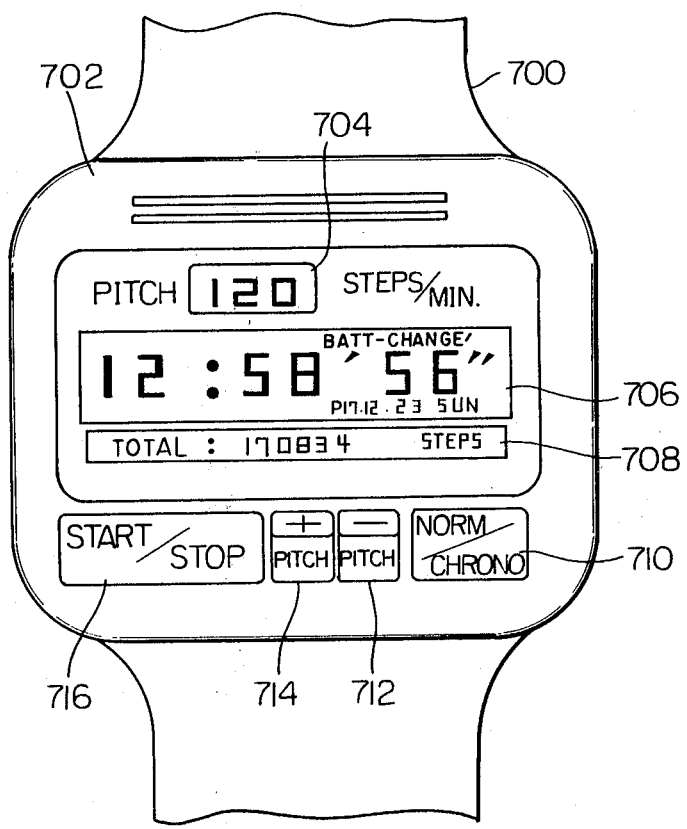
FIG. 30 is an external view of a combined digital timepiece and pace timing device.

An external view is shown in FIG. 30 of a combined pace timing device and digital timepiece. Numeral 700 indicates the wristband, and 702 the case. The frequency of a pace timing signal is indicated by a digital display 704, as a number of steps per minute. The cumulative number of steps from some intial starting point is indicated by display 708 in digital form. Display 706 provides the current time and date etc., as shown, or shows a chronograph display, with changeover between the chronograph and current time displays being controlled by actuation of a control member 710, which is coupled to a switch. The frequency of the pace timing signal is increased by actuating a control member 714, and is decreased by actuating a control member 712. The pace timing signal frequency is denoted as the "pitch", in FIG. 30. This is to indicate that the actual frequency with which actions are to be performed is being referred to, irrespective of any pauses in the audible timing signal due to a rythm component.

The various displays of this embodiment can be provided by, for example, liquid crystal display cells. A single large cell can be used to provide all of the displays, or individual smaller display cells can be used for each of the various displays. If a single large display cell is used, then the various display areas can be delimited by a mask plate with windows. In this case, in order to reduce the large number of connections which are necessary to make with the display cell, it is preferable to utilize a matrix drive system.

It will be assumed that the device will be set to the chronograph mode of operation and display when the pace timing facility is being used. The circuit to which operating members 714 and 712 are coupled is such that, each time one of these operating members is actuated, the pace timing frequency is increased (or decreased) by one step per minute. If the operating member is held depressed for more than one second, then the pace timing frequency begins to be rapidly increased (or decreased), at a rate of several Hertz. Thus, alteration of the pace timing signal frequency can be conveniently controlled by the user.

Figure 31:
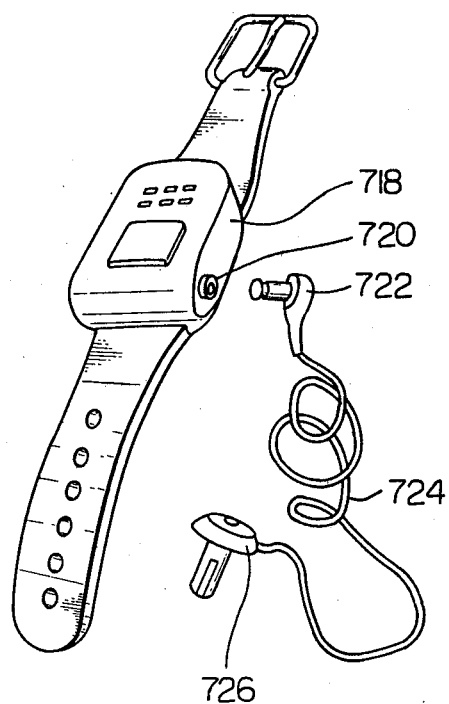
FIG. 31 is an external view of a pace setting device equipped with an auxiliary earpiece.

FIG. 31 shows an embodiment of a pace timing device which is equipped with an earphone 726. The earphone is connected to the pace timing device by a connecting cord 724, and a jack plug 722, which is inserted in a jack socket 720 in the pace timing device body 718. When the jack plug 722 is inserted, generation of audible signals by the miniature loudspeaker of the pace timing device is cut off, and the audible signals are generated by earphone 726. When jack plug 722 is removed, the audible signals are generated by the miniature loudspeaker in pace timing device body 718. The earphone may be of electromagnetic type or of piezoelectric type, utilizing for example Rochelle salt.

Figure 32:
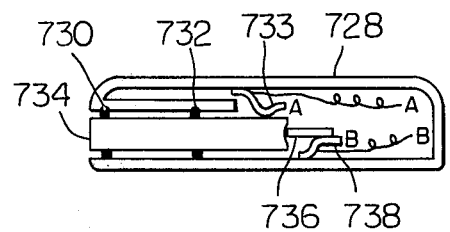

It is possible to construct a pace timing device according to the present invention in which the battery is accomodated in a similar fashion to that of a conventional form of digital electronic timepiece, i.e. in which the battery is sealed within the body of the pace timing device in such a way as to be inaccessible to the user, and in which the device must be taken to a store which sells such devices, or to a manufacturer's service facility, in order to replace the battery when such replacement becomes necessary. However this is inconvenient in some circumstances. FIG. 32 is a cross-sectional view of part of a pace timing device having a battery which can be freely inserted or removed from the exterior of the device. The arrangement is waterproof, and is suitable for use with lithium batteries of cylindrical shape, which are readily available, being already in use in various small-size devices such as electronic calculators, etc. Such an arrangement is also suitable for use with a silver oxide cell. In FIG. 32, the casing 728 of the pace timing device is equipped with an aperture containing O-rings 730 and 732, which are made of silicon rubber, for example. The battery is supported by O-rings 730 and 732, and the assembly constitutes a waterproof structure. The outer wall of battery 734 serves as one electrode, which contacts a springy contact member 733, while another contact member 738 contacts the inner electrode 736 of the battery. Contact members 733 and 738 are connected to the circuit of the pace timing device, supplying power thereto.

It should be noted that a construction such as that of the embodiment of FIG. 32 is also suitable for other types of small electronic devices, such as hearing aids, due to the ease of battery replacement.

Figure 33A:
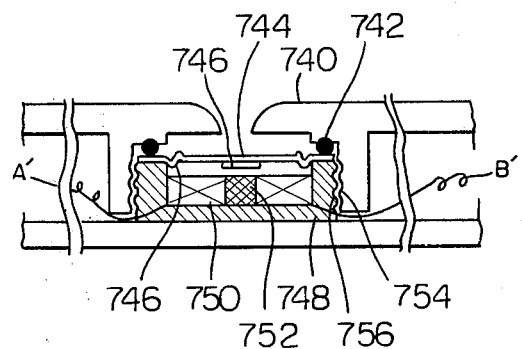
FIG. 33A and 33B are cross-sectional views of waterproof miniature loudspeaker assemblies for a pace setting device.

FIG. 31A and 31B show cross-sectional views of parts of embodiments of a pace timing device, illustrating arrangements for a waterproof construction of a miniature loudspeaker. In FIG. 33A, a casing 740 is equipped with an O-ring 742. A diaphragm 744, which vibrates to produce sound waves, consists of a soft (i.e. non-permanent) ferromagnetic material. A weight 746 is formed of a soft ferromagnetic material, and is used to adjust the resonant frequency of the loudspeaker. A corrugated portion 746 of diaphragm 744 enables the inner portion of diaphragm 744 to move freely. The loudspeaker construction also includes an outer member 748, made of magnetically permeable material such as Permaloy or soft iron, a drive coil 750, and a permanent magnet 752 for providing a magnetic bias, and consisting of a ferrite magnet, a cobalt samarium magnet, or a colbalt promethium magnet, for example.

Although the permanent magnet in this arrangement is situated in the core of the drive coil, it is equally possible to position the permanent magnet in any other part of the magnetic circuit.

The casing 740 has a screw thread 754 in which a screw thread 756 of the outer member 748 is formed. When the loudspeaker is screwed into the casing, the O-ring 742 is pressed against the casing by the periphery of the diaphragm, to form a waterproof construction.

Figure 33B:
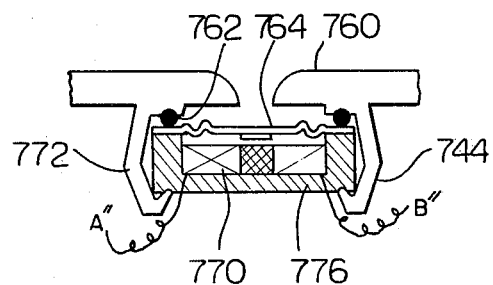

Another arrangement of a loudspeaker for a pace timing device is shown in FIG. 33B. This arrangement includes a casing 760, an O-ring 762, a biasing magnet 768, a drive coil 770 and springs 772 and 774 which hold the loudspeaker assembly within the casing in a resilient manner.

In the case of both the embodiments of FIG. 33A and 33B, the casings 740 and 760 can be formed of plastic, with various recesses and springs formed in the plastic, to hold the loudspeaker and various other small parts of the device. These springs and recesses can all be formed at the time of molding the case, or can be formed separately, by heat treatment to shape the casing.

Although the arrangements of FIG. 33A and 33B do not provide an extremely high degree of waterproofing, they are effective in preventing the entry of sweat, rain, etc. into the interior of the casing, and provide almost no adverse effect upon the sound quality produced by the loudspeaker.

Figure 34:
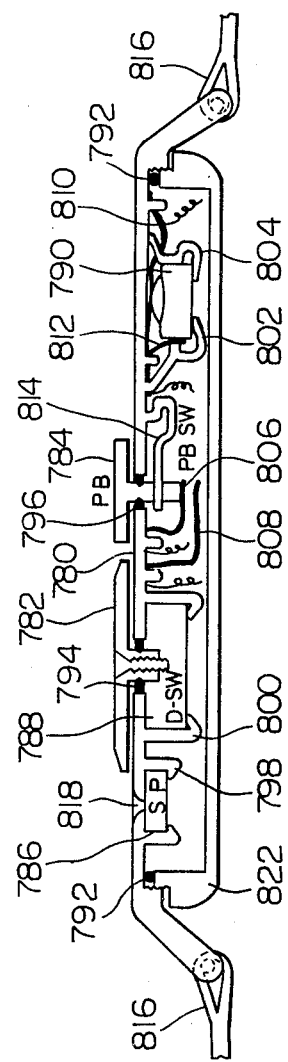
FIG. 34 is a cross-sectional view of an embodiment of a pace setting device according to the present invention.

FIG. 34 is a cross-sectional view of an embodiment of a pace timing device according to the present invention. Shown are a casing 780, a dial 782, a pushbutton switch 784, a loudspeaker 786, a rotary switch 788 and a battery 790. Numerals 792, 794 and 796 denote O-rings. Various components are held in place by lugs 798, 800, 802 and 804. Contact members are denoted by numerals 806, 808, 810 and 812. Pushbutton switch 784 is held in position by a spring 814. Numeral 816 denotes a wrist strap. Sound from the loudspeaker issues from an aperture 818. This embodiment is of waterproof construction, and the various parts are mounted in the casing 780 by means of members formed integrally with casing 780, which is made of plastic. Back cover 822 is held in close contact with casing 780 by means of O-ring 792. This type of construction is highly economical, and makes the best use of the molding techniques which are available for plastic components, using metal molds.

Figure 35:
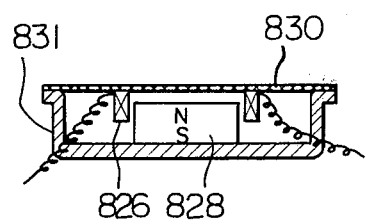
FIG. 35, 36 and 37 are cross-sectional views of further embodiments of miniature loudspeakers for pace setting devices.

Various types of miniature loudspeaker are applicable to a pace timing device according to the present invention and these will now be discussed. Referring to FIG. 35, a moving coil type of loudspeaker is shown, in which a coil 826 surrounds a permanent magnet 828, the coil 826 being fixedly supported on a diaphragm 830. Diaphragme 830 is supported at its periphery by an outer member 831, which is made of a permeable ferromagnetic material. The diaphragme 830 can be made of phosphor bornze, aluminum, plastic or paper.

Figure 37:
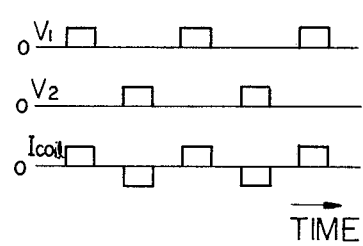
Figure 36:
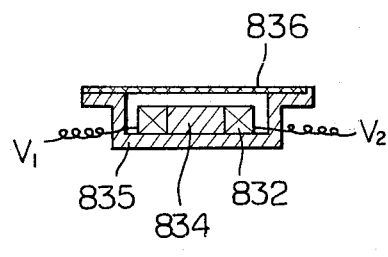

FIG. 36 shows a variable reluctance type of loudspeaker, which does not employ a permanent magnet as a source of magnetic bias. This comprises a drive coil 832, a permeable ferromagnetic inner member 834, and outer member 835, and a diaphragm 836 which is made of a permeable soft ferromagnetic material. This type of loudspeaker must be driven by a push-pull drive signal comprising pulses with time intervals separating successive pulses, as illustrated in FIG. 37. In FIG. 37, IcO denotes the drive current of the loudspeaker.

Figure 38:
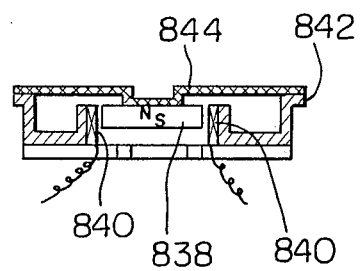
FIG. 38 is a waveform diagram illustrating the waveform required to be applied to a miniature loudspeaker of variable reluctance type, as shown in FIG. 36.

FIG. 38 shows an example of a moving magnet type loudspeaker. A magnet 838 fixed to a diaphragm 844 is actuated by a drive coil 840, held in an outer member 842 made of magnetically permeable material.

Figure 39:
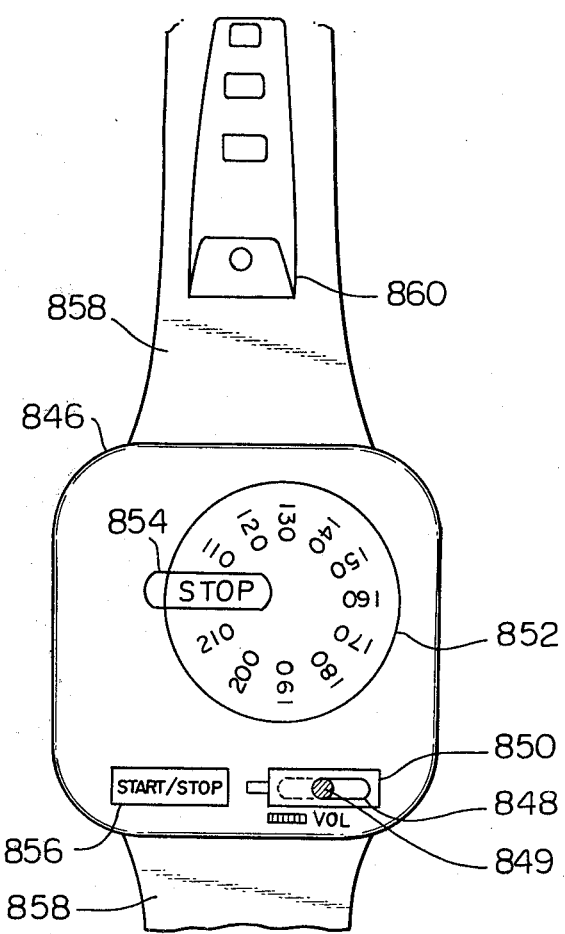
FIG. 39 is an external view of an embodiment of a pace timing device.

The intensity of the sound emitted by a miniature loudspeaker which is driven by a pulse signal can be controlled by pulse width modulation. This can be emplemented by means of a variable resistance which is manually adjusted by the user. However a simpler method of adjusting the output sound level can be utilized, as illustrated in FIG. 39, which is an external view of a pace timing device embodiment according to the present invention. This embodiment includes a casing 846, an aperture 849 through which emitted sound is passed. The effective size of aperture 849 can be adusted by moving a sliding member 850 to the left or right. Sliding member 850 has an aperture 848 provided therein, so that the effective size of aperture by which sound is emitter can be controlled.

Numeral 852 denotes a control dial which can be rotated to set the frequency of a pace timing signal. The dial is graduated in a linear manner with respect to frequency. Dial 852 comprises a transparent acrylic plate with the numbers of steps per minute printed thereon in black numerals. A mark 854 is provoided on casing 846, mark 854 being colored white, while the casing 846 is colored dark brown. In FIG. 39, the dial 852 is set to the position of the STOP indication, which shows that the device is in the inoperative state. Numeral 856 denotes an operating member controlling a pushbutton switch used to initiate or terminate operation of the device.

If the circuit of the embodiment shown in FIG. 39 is assumed to be that shown in FIG. 27A to 27C, then switch 578 in FIG. 27B would be operated by operating member 856, while digital switch 550 would be coupled to dial 852, to be set thereby to provide various code combinations. The STOP position of dial 852 can be made to correspond to the setting of digital switch 550 whereby all of input terminals 551 (FIG. 27A) are at the H level. To promote effective transmission of sound from the device to the user's ear, in the case of a person who is running with the arms bent at right angles, the sound emitting aperture of the device should be situated near the right-hand periphery of the device, as shown in FIG. 39, for maximum efficiency. For improved road safety, when exercising at night, reflecting beads can be attached around the edges of the case 846, to attract the attention of other road users, by reflecting light from the passing vehicles at night.

The device can also be arranged such that a lamp is provided to illuminate dial 852, this lamp being turned on when the user starts operation of the device by switch 856.

A key holder section is provided on wrist strap 858, to accommodate keys while exercise is being undertaken.

As stated hereinabove, it is possible to use either a variable frequency oscillator, or a system which derives a variable frequency signal on the basis of a fixed frequency reference signal, to produce a pace timing signal that can be set to a desired frequency by the user. In the case of a variable frequency osciallator, a ring oscillator which is preferably supplied from a stabilized power source offers certain advantages. The power source can be designed to compensate for the effects of temperature and battery voltage changes upon the oscillator frequency. However, in the usual method of controlling the frequency of such a variable frequency oscillator, i.e. by means of a variable control element such as a variable resistor or variable capacitor, the movement of the variable control element will generally have a very non-linear relationship to the controlled frequency. A preferable method is to employ a frequency-to-voltage converter for measuring the controlled frequency, and a comparator circuit which compares the output voltage from the converter with the voltage produced by a variable resistor, the output voltage from the comparator circuit being applied to control the desired frequency. In this way, a linear relationship is established between the movement of the variable resistor and the controlled frequency.

An alternative method is to utilize a rotary switch rather than a variable resistor or capacitor to control the oscillator frequency of a variable frequency oscillator. If this is done, then the oscillator circuit can be arranged such that a linear relationship exists between the incremental switch positions and the oscillator frequency.

Use of a fixed frequency oscillator as a source of a reference frequency for deriving a varialbe frequency signal, on the other hand, is prefereable in the case of a pace timing device in which time intervals are measured. In the case of a combined electronic timepiece and pace timing device, the reference frequency oscillator which provides the time unit signal for timekeeping can also be used to derive a variable frequency signal for pace timing purposes. This can be done, for example, by one of the methods illustrated in FIG. 13A, 13B and 13C, which have been discussed hereinabove. The fixed frequency signal source may employ a quartz crystal vibrator, a lithium tantalate vibrator, a barium titanate vibrator, or other piezoelectric vibrator. The use of a quartz crystal vibrator is advantageous due to the fact that such vibrators are currently widely produced. Suitable types of quartz crystal vibrator include a +5° X-cut tuning fork type, a thin quartz vibrator produced by an etching process, or an AT cut quartz crystal vibrator having an oscillation frequency of several megaherz.

Where the frequency of the pace timing signal is controlled by rotation of a variable resistor or capacitor, or by a rotary switch, a dial can be provided on the rotary element to indicate the frequency which has been selected. The various frequencies can be indicated upon this dial, with a fixed mark being provided on the case adjacent to the dial, or the frequencies can be marked on the case adjacent to the dial, with a mark on the dial being provided to indicate the selected frequency.

Where a variable resistor or capacitor is employed, the dial can either be coupled directly to the variable element, or coupled thereto through a speed reduction mechanism. The selected pace timing signal frequency can also be indicated by a digital or analog display section.

The pace timing frequency can be selected with a higher degree of accuracy if selection is performed in successive increments, by means of a switch. The switch can be a simple rotary type coupled to an oscillator circuit to control its frequency, or can be a digital type of rotary switch which applies input signals to a frequency converter system, as in the embodiment of FIG. 27A. A single push-button switch can also be utilized, to select the pace timing signal frequency in discrete increments, in conjunction with a counter circuit used as a memory to store frequency information generated by the pushbutton switch, as in the case of the embodiment of FIG. 21A to 21D, in which switch 466 serves to select the pace timing signal frequency. Also, as in the case of the embodiment of FIG. 21A to 21D, control of the information input by a single pushbutton switch can be achieved by measuring the duration for which the switch is actuated, and changing over various circuit functions in accordance with differences in duration of actuation of the switch. As is also illustrated by this embodiment, information can be fed back to the user of the device by means of audible signals, to indicate that manipulation of the switch in a particular manner has been effected, so that a predetermined function has been selected or that particular information can now be input by successive actuations of the switch. By utilizing a single pushbutton switch in this manner, a pace timing device of compact size can be produced which is economical to manufacture.

As is also illustrated by the embodiments of FIG. 21 and 27, timer circuit means can be included in a pace timing device whereby the operation of the device is terminated after a predetermined time interval of, for example, one hour has elapsed. When operation is terminated, the operation of an oscillator circuit is halted. In the case of an integrated circuit employing complementary MOS field effect transistor elements, it can be arranged that a negligible amount of power is consumed by the device when in the inoperative state, by setting all of the transistor elements in a reverse-biased state. In this way, it is not necessary to use a power ON/OFF switch, and the danger of the battery being unnecessarily run down due to the device being accidentally left in the operating condition is eliminated.

As illustrated by the embodiment of FIG. 21, successive intervals of elapsed time may be indicated by audible signals through a "repeater" system, in which the number of time intervals which have elapsed is indicated by a corresponding number of tone bursts. Alternatively, such a repeater system may be used to indicate the number of steps which have been executed. Separate electronic counters may be used for a step number and a timer repeater system, or a single counter may be used for both functions, through changeover switching means and a suitable arrangement for changing the count factor of the counter (from 60 to 100, for example). Instead of indicating numbers of steps, such a system can indicate distance travelled, by assuming a length of pace and multipying this by the number of steps executed. Indication can be given at every minute, every 10 minutes, or other time intervals, in the case of time measurement, or at every kilometer, every 10 kilometers in the case of a distance measuring system. As in the embodiment of FIG. 21, the audible tone signals which indicate elapsed time, numbers of steps, or distance, can be modulated in a different manner manner from the audible signals which indicate the pace timing, so that no confusion will occur. This can be done by modulating twice at two different frequencies, as in the embodiments of FIG. 21 and FIG. 28. Also, in order to avoid such confusion, the audible signals which indicate elapsed time, etc, should replace the pace timing signals which would otherwise occur at the same time. Such audible signals may also be used to indicate an accumulated total number of steps or total distance traveled, over a number of exercise periods, as well as the numbers of steps or distance in each particular exercise period.

When indication of such a variety of data is to be selectively provided by actuation of a single operating member, such as a pushbutton switch, some care must be taken in ensuring that the user can readily understand the method of operation. For example, the essential operating information can be written directly on the pace timing device, or on a slip of paper or plastic attached thereto. Or, if an optical display system is also utilized, various visible displays can be provided to indicate, for example, "elapsed time display enabled", "current time display enabled", "cumulative time display enabled", etc., in accordance with the user's actuaion of one or more operating members. An alternative method is to use separate operating members for different functions, in conjunction with an optical display. A pushbutton could be provided which is marked "elapsed time period", which, when actuated, would cause the elapsed time period to be read out on the display.

Acoustic and optical displays may be combined in various ways. For example, a symbol or marker indicating "step number" can be caused to flash on and off on the display, while the corresponding number of steps is produced as an audible indication, by a repeater facility.

What is claimed is:

1. A combination of an electronic timepiece and pace timing device, comprising:

a source of a first frequency signal;

pace signal generation circuit means responsive to said first frequency signal for providing a pace signal;

an acoustic device responsive to said pace signal for providing an audible pace timing signal;

said first frequency signal source including a source of a timebase signal, externally operated frequency setting means, and synthesizer circuit means responsive to operation of said frequency setting means and to said timebase signal for producing a first frequency signal;

said pace signal generation circuit means including a frequency divider coupled to receive said timebase signal for thereby producing a carrier signal and time unit signal, and a modulator circuit for modulating said carrier signal by said first frequency signal to thereby produce a pace signal; and a timekeeping counter circuit coupled to receive said time unit signal produced by said frequency divider circuit for thereby producing a time marker signal when a predetermined count of said time unit signal is attained, said time marker signal being applied to said modulator circuit to modulate said carrier signal for thereby producing a modulated time marker signal, said acoustic device being responsive to said modulated time marker signal for producing an audible time marker signal;

externally actuated switch means for selecting a timekeeping mode of operation and a pace timing mode of operation;

externally actuated switch means for selectively increasing and decreasing a pace timing signal frequency when said pace timing mode of operation is entered;

externally actuated switch means for initiating halting production of an audible pace timing signal when said pace timing mode of operation is entered;

display means for displaying current time and date when said timekeeping mode of operation is entered and for displaying an elapsed time when said pace timing mode of operation has been entered;

display means for indicating a pace timing signal frequency when said pace timing mode of operation is entered; and display means for indicating a cumulative total of steps executed.

2. A pace timing device, comprising:
a source of a timebase signal;
externally operated frequency setting means;
synthesizer circuit means responsive to operation of said frequency setting means and to said timebase signal for producing a first frequency signal;
a frequency divider coupled to receive said timebase signal for thereby producing a carrier signal and time unit signal;
a modulator circuit for modulating said carrier signal by said first frequency signal to thereby produce a pace signal;
an acoustic device respective to said pace signal for producing an audible pace timing signal; and
a timekeeping counter circuit coupled to receive said time unit signal produced by said frequency divider circuit for thereby producing a time marker signal when a predetermined count of said time unit signal is attained, said time marker signal being applied to said modulator circuit to modulate said carrier signal for thereby producing a modulated time marker signal, said acoustic device being responsive to said modulated time marker signal for producing an audible time marker signal.

3. A pace timing device according to claim 2 wherein said frequency divider circuit produces a first carrier signal and a second carrier signal of differing frequencies, and wherein said first carrier signal is modulated by said first frequency signal in said modulator circuit to produce said pace signal and wherein said second carrier signal is modulated by said time marker signal to produce said modulated time marker signal.

4. A pace timing device according to claim 2 wherein said frequency divider produces a first carrier signal and a second carrier signal of differing frequencies, and wherein said second carrier signal is modulated by said time marker signal and the signal resulting from this modulation is applied to modulate said first carrier signal to produce said modulated time marker signal.

5. A pace timing device according to claim 2, and further comprising electro-optical display means for receiving said modulated time marker signal and for thereby providing a visible indication of an elapsed time.

6. A pace timing device according to claim 2, and further comprising a counter circuit and externally operated changeover switching means coupled to said counter circuit whereby said counter circuit is selectively caused to count said first frequency signal and a time unit signal produced by said frequency divider circuit in accordance with said changeover switching means, said counter circuit producing time marker signal when said time unit signal is counted and producing a step count signal when said first frequency signal is counted.

7. A pace timing device, comprising:
a source of a timebase signal;
externally operated frequency setting means;
a frequency synthesizer circuit responsive to operation of said frequency setting means and to said timebase signal for producing a first frequency signal;
a frequency divider coupled to receive said timebase signal, for thereby producing a carrier signal and a time unit signal;
a modulator circuit for modulating said carrier signal by said first frequency signal to thereby produce a pace signal; and
an acoustic device responsive to said pace signal for producing an audible pace timing signal; and
wherein said frequency synthesizer circuit comprises:
a counter circuit for counting pulses of said timebase signal;
memory means responsive to signals produced by said setting means for storing a numeric value;
comparator circuit means for comparing the count of said counter with said numeric value and for producing a first output signal when coincidence is detected between said count and said numeric value, and further, for producing a second output signal when a predetermined count of said counter circuit is attained;
a bistable circuit responsive to the first output signal from said comparator circuit for producing a first control signal and responsive to the second output signal from said comparator circuit for producing a second control signal; and
a gate circuit coupled to receive said timebase signal and responsive to said second control signal for passing said timebase signal to an output terminal and being furthermore responsive to said second control signal for inhibiting passage of said timebase signal to said .

8. A pace timing device, comprising:
a source of a timebase signal;
externally operated frequency setting means;
a frequency synthesizer circuit responsive to operation of said frequency setting means and to said timebase signal for producing a first frequency signal;
a frequency divider coupled to receive said timebase signal, for thereby producing a carrier signal and a time unit signal;

a modulator circuit for modulating said carrier signal by said first frequency signal to thereby produce a pace signal; and an acoustic device responsive to said pace signal for producing an audible pace timing signal; and wherein said frequency synthesizer circuit comprises:

a frequency divider circuit for dividing the frequency of said timebase signal;

a decoder circuit coupled to receive output signals from a plurality of stages of said frequency divider circuit and thereby generate weighted gating signals;

selection and memory circuit means responsive to signals produced by said setting means for selecting at least one of said weighted gating signals; and a gate circuit for receiving said timebase signal and responsive to said selected weighting gate signal for passing said timebase signal to an output terminal.

9. A pace timing device, comprising:

a source of a timebase signal;

externally operated frequency setting means;

a frequency synthesizer circuit responsive to operation of said frequency setting means and to said timebase signal for producing a first frequency signal;

a frequency divider coupled to receive said timebase signal, for thereby producing a carrier signal and a time unit signal;

a modulator circuit for modulating said carrier signal by said first frequency signal to thereby produce a pace signal; and an acoustic device responsive to said pace signal for producing an audible pace timing signal; and wherein said frequency synthesizer circuit comprises:

a frequency divider circuit for dividing the frequency of said timebase signal;

a voltage-controlled oscillator circuit;

a counter circuit for counting an output signal of said voltage-controlled oscilltor circuit;

memory means responsive to signals produced by said setting means for storing a numeric value;

comparator means for comparing the count in said counter circuit with said numeric value, and for generating an output signal when coincidence is detected between said count and numeric value, said output signal being applied to said counter for causing the contents thereof to be reset to a count of zero; and a phase detector circuit for comparing the phase of an output signal produced by said counter circuit and the phase of an output signal of said frequency divider circuit, and for producing a control signal indicative of a phase difference, said control signal being applied to said voltage-controlled oscillator to control the phase of the output signal thereof.

10. A pace timing device according to claim 9, wherein said voltage-controlled oscilaltor comprises a ring oscillator circuit.

11. A pace timing device according to claim 10, wherein said ring oscillator circuit comprises a plurality of complementary field effect transistor elements.

12. A pace timing device, comprising:

a source of a first frequency signal;

pace signal generation circuit means responsive to said first frequency signal for providing a pace signal;

an acoustic device responsive to said pace signal for providing an audible pace timing signal;

a step counter circuit for counting said first frequency signal and for producing a step count signal when a predetermined number of pulses of said pace signal have been counted;

means for detecting that the count in said step counter circuit has attained a value which is an integral multiple of a predetermined count value and for generating a control signal when such a count value is detected; and means responsive to the contents of said step counter circuit and to said control signal for generating a step count repeater signal indicative of the value of said integral multiple.

13. A pace timing device according to claim 12, wherein said step count repeater signal comprises a single pulse when said detection means first detects that a count value equal to said predetermined count value has been attained by said step counter, and subsequently comprises a plurality of pulses generated each time that a value of said integral multiple of greater than one is detected, the number of said plurality of pulses being equal to said integral multiple.

14. A pace timing device according to claim 13, and further comprising a source of a carrier signal and modulation circuit means, said modulation circuit modulating said carrier signal by said step count repeater signal to generate a modulated step count repeater signal, and said acoustic device being responsive to said modulated step count repeater signal for producing an audible step count repeater signal.

15. A pace timing device according to claim 14, wherein said step counter circuit comprises a first and a second step counter circuit, and wherein an output signal of said first step counter circuit is input to said second step counter circuit, said output signal being applied as a carry input signal to said second step counter circuit each time the count in said first step counter circuit has been incremented by said predetermined count value, and wherein said output signal of said first step counter constitutes said control signal.

16. A pace timing device according to claim 15, wherein said step count repeater signal generating means comprises:

a repeater signal counter circuit responsive to said control signal for being reset to a count of zero;

a gate circuit coupled to receive said first frequency signal and having an output terminal coupled to a clock input terminal of said repeater signal counter circuit, comparator circuit means for comparing the count in said second step counter circuit with the count in said repeater signal counter circuit and for producing a coincidence detection circuit signal when coincidence is detected between said counts;

bistable circuit means responsive to said coincidence detection signal for being set to produce an output at a first logic level potential, said output being applied to an input of said gate circuit to enable said first frequency signal to be applied to said repeater signal counter when at said first logic level potential; and a source of a reset signal, said reset signal being generated after a predetermined time interval following generation of said control signal and being applied to said bistable circuit means to thereby reset said bistable circuit means to generate an output signal at a second logic level potential, whereby said gate circuit is inhibited from passing said clock pulses to said repeater signal counter;

the output signal from said gate circuit constituting said step count repeater signal.

17. A pace timing device, comprising:

a source of a first frequency signal;

pace signal generation circuit means responsive to said first frequency signal for providing a pace signal;

an acoustic device responsive to said pace signal for providing an audible pace timing signal;

an elapsed time and step number counter circuit;

a source of a changeover control signal;

a source of a timebase signal;

frequency divider means for frequency dividing said timebase signal to provide a unit time signal;

changeover gate circuit means for receiving said unit time signal and said first frequency signal, being responsive to said changeover control signal for selectively applying said unit time signal and said first frequency signal to an input of said elapsed time and step number counter circuit;

carry control gate circuit means responsive to said changeover control signal for causing said elapsed time and step number counter circuit to count by a first count factor when said first frequency signal is applied to said elapsed time and step number counter circuit and to count by a second count factor when said unit time signal is applied to said elapsed time and step number counter circuit;

means for detecting that the count in said elapsed time and step number counter circuit has attained a count value which is an integral multiple of a predetermined count value and for generating a control signal when such a count value is detected; and means responsive to the contents of said elapsed time and step number counter circuit and to said control signal for generating a step count and elapsed time repeater signal indicative of the value of said integral multiple.

18. A pace timing device according to claim 17, wherein said step count and elapsed time repeater signal comprises a single pulse when said detection means first detects that a count value equal to said predetermined count value has been attained by said elapsed time and step counter circuit, and subsequently comprises a plurality of pulses generated each time that a value of said integral multiple of greater than one is detected, the number of said pulses being equal to said integral multiple.

19. A pace timing device according to claim 18, and further comprising a source of a carrier signal and modulation circuit means, said modulation circuit means modulating said carrier signal by said step count and elapsed time repeater signal, to produce a modulated step count and elapsed time repeater signal, said acoustic device being responsive to said modulated step count and elapsed time signal for producing an audible step count and elapsed time signal.

20. A pace timing device, comprising:

a source of a first frequency signal and a timebase signal, said source including an oscillator circuit;

an operating switch coupled to an external operating member, for producing a single operating signal each time said operating member is actuated;

a bistable circuit responsive to said operating signal for being set to produce a first control signal;

a gate circuit coupled to said oscillator circuit to control the operation thereof, and responsive to said first control signal for enabling operation of said oscillator circuit;

frequency divider circuit means coupled to receive said timebase signal and produce a time unit signal;

timekeeping circuit means coupled to receive said time unit signal and to produce a terminating signal when a predetermined time has elapsed, said terminating signal being applied to a reset terminal of said bistable circuit to reset said bistable circuit, thereby causing said gate circuit to inhibit oscillation by said oscillator circuit;

pace signal generation circuit means responsive to said first frequency signal for providing a pace signal; and an acoustic device responsive to said pace signal for providing an audible pace timing signal.

21. A pace timing device according to claim 20, wherein said operating switch is coupled to an input circuit comprising:

a resistor or relatively high value having one terminal connected to said input terminal and another terminal connected to a first logic level potential;

a field effect transistor having a drain electrode connected to said input terminal and a source electrode connected to said first logic level potential;

an inverter having an input terminal connected to said input terminal and an output terminal connected to a gate electrode of said field effect transistor;

whereby said input terminal is maintained in a low impedance condition at said first logic level potential when said operating switch is in an open condition, and wherein closing of said operating switch sets said input terminal to a second logic level potential, this transition between said first and second logic level potentials constituting said operating signal.

22. A pace timing device according to claim 20, and further comprising:

toggle-type bistable circuit means responsive to successive occurrences of said operating signal for producing an output signal which successively alternates between said first and second potentials;

drive circuit means coupled between said pace signal generation means and said acoustic device; and control gate means coupled to said drive circuit means and responsive to the first potential state of said output signal from said toggle-type bistable circuit means for enabling said pace signal to be applied to said drive circuit and responsive to the second potential state of said output signal from said toggle-type bistable circuit means for inhibiting said pace signal from being applied to said drive circuit.

23. A pace timing device according to claim 21, and further comprising:

a first input control counter circuit responsive to said first potential state of said input terminal for being reset to a count of zero;

a first gate circuit coupled to receive a clock signal produced by said frequency divider circuit and having an output terminal coupled to an input terminal of said first input control counter circuit;

a second gate circuit coupled to output terminals of said first input control counter circuit and having an output terminal coupled to an input of said first gate circuit, whereby said first gate circuit is inhibited from passing said clock pulses to said first input control counter circuit when a predetermined count is attained in said first input control counter circuit, by an output signal from said second gate circuit, and is enabled to pass said clock pulses otherwise;

the output from said second gate circuit being applied to a reset terminal of said timekeeping circuit, whereby the contents of said timekeeping circuit are reset to zero when said predetermined count is attained by said first input control counter circuit.

24. A pace timing device powered by a battery, comprising:

- a timebase oscillator circuit including a control gate circuit, oscillation by said timebase oscillator circuit being enabled when said control gate is in an inhibited condition and being enabled when said control gate is in an enabled condition;
- a frequency divider comprising a counter circuit coupled to receive a timebase signal produced by said timebase oscillator circuit;
- a first time counter circuit coupled to receive an output signal from said frequency divider counter circuit and therey produce a unit time signal;
- a second time counter circuit coupled to receive said unit time signal and to thereby produce a time marker signal each time a first time interval has elapsed and to produce a termination signal when a second time interval has elapsed, said second time interval comprising an integral multiple of said first time interval;
- an externally actuated digital switch for setting a code combination representing a numeric value, and comprising a plurality of electrical signals;
- a comparator circuit for comparing said code combination with a count held in said frequency divider counter circuit, and for producing a coincidence signal when coincidence between said code combination and said count is detected;
- a first gate circuit for detecting a predetermined count of said frequency divider counter circuit and for producing a detection signals when said count is detected;
- a bistable circuit responsive to said detection signal for being reset to produce a first output signal, and responsive to said conicidence signal for being set to produce a second output signal;
- a second gate circuit coupled to receive a first clock signal of relative high frequency from an input stage of said frequency divider counter circuit, being responsive to said first output signal for passing said first clock signal and being respnsive to said second output signal for inhibiting passage of said first clock pulses;
- a pace signal counter for counting output signal pulses from said second gate circuit;
- a third gate circuit coupled to receive output signals from said pace signal counter, for thereby producing a first frequency signal comprising a train of pulses having an average frequency determined by said code combination from said digital switch;
- a rhythm signal counter coupled to receive an output signal from said pace signal counter and to produce an output signal coinciding with alternate successive pairs of pulses of said first frequency signal, said rhythm signal counter output signal being applied to said third gate circuit for inhibiting alternate successive pairs of pulses of said first frequency signal from being produced thereby;
- a fourth gate circuit coupled between said rythm signal counter and said third gate means, for controlling application of said outlet signal of said rhythm signal counter to said third gate circuit;
- a function control terminal comprising an externally controlled terminal, coupled to an input of said fourth gate circuit, whereby said output signal from said rhythm signal counter is enabled to be applied to said third gate circuit when said function control terminal is at a first potential and is inhibited from being applied when said function control terminal is at a second potential;
- a modulator circuit coupled to receive said first frequency signal, said time marker signal, said termination signal, and carrier signals comprising third and fourth clock signals of relatively low frequency produced by said first time counter circuit, whereby said first frequency modulates said third clock signal to produce a pase timing signal, said time marker signal modulates said fourth clock signal and the resultant signal modulates said third clock signal to produce a modulated time marker signal, and said termination signal modulates said fourth frequency signal and the resultant signal modulates said third clock signal to produce a modulated terminal signal;
- driver circuit means coupled to receive said pace signal, said modulated time marker signal, and said modulated termination signal and thereby produce drive signals;
- an electrodynamic loudspeaker responsive to said drive signals for producing an audible pace timing signal, an audible time marker signal, and an audible termination signal;
- an externally actuated operating switch, for producing a single operating signal comprising a transition from a first potential to a second potential when actuated;
- a second bistable circuit responsive to said operating signal for being set to produce an operation enable signal, said operating enable control signal being applied to said control gate of said timebase oscillator circuit to enable oscillation thereof;
- an input control counter circuit responsive to said second potential from said operating switch for being reset to a count of zero;
- a fifth gate circuit coupled to receive a clock signal produced by said first time counter circuit and having an output terminal coupled to an input terminal of said input control counter circuit;
- a sixth gate circuit coupled to output terminals of said input control counter circuit for detecting a predetermined count thereof, and having an output terminal coupled to an input of said fifth gate circuit, to inhibit said fifth gate circuit when said predetermined count is detected;
- the output from said sixth gate circuit being applied to reset terminals of said second time counter circuit, whereby said second time counter circuit is reset when said predetermined count of said input control counter circuit is detected;
- a timer control counter circuit responsive to said operating signal for being reset to a count of zero;

a seventh gate circuit coupled to receive a clock signal produced by said first time counter circuit, and having an output-terminal coupled to an input terminal of said timer control counter circuit; and an eighth gate circuit coupled to output terminals of said timer control counter circuit for detecting a predetermined count thereof, and having an output terminal coupled to an input of said seventh gate circuit, to inhibit said seventh gate circuit when said prdetermined count is detected;

the output from said eighth gate circuit being applied to a control terminal of said modulator circuit, whereby said modulator circuit is enabled to produce said pace signal prior to said predetermined count of said timer control counter circuit being detected, and is inhibited from producing said pace signal after said predetermined count has been detected.

25. A pace timing device powered by a battery, comprising:

a timebase oscillator circuit including a control gate circuit;

a frequency divider comprising a counter circuit, coupled to receive a timebase signal produced by said timebase oscillator circuit;

a first time counter circuit coupled to receive an output signal from said frequency divider counter circuit, and thereby produce a unit time signal;

an externaly actuated operating switch for producing an operating signal;

a first bistable circuit responsive to said operating signal for being reset, to thereby produce an operation enable signal, said operation enable signal being applied to said control gate of the timebase oscillator circuit to enable oscillation thereof;

a first input control counter coupled to receive a clock signal from said first time counter circuit, said operating signal being coupled to control terminals of said first input control counter circuit to enable counting thereby;

a first gate circuit for detecting a predetermined count of said first input control counter, and for producing an output signal when said predetermined count is detected;

a second input control counter coupled to receive the output signal from said first gate circuit and to count successive occurrences of said output signal, counting by said second input control counter being enabled by said operating signal;

a second gate circuit for detecting a predetermined count of said second input control counter and for producing an output signal when said count is detected, the output signal from said second gate circuit being applied to said first gate circuit to inhibit application of said clock signal to said first intput control counter circuit;

a second bistable circuit responsive to the output signal from said second gate circuit for being set to produce a first gate control signal;

a third bistable circuit responsive to the output signal from said first gate circuit for being set to produce a second gate control signal;

circuit means for producing an actuation signal, comprising a short duration pulse produced at the start of said operating signal when said operating switch is actuated;

a third gate circuit responsive to said actuation signal and to the logical inverse of said first gate control signal for producing an output signal, said output signal being applied to reset said third bistable circuit, for thereby producing a fourth gate control signal;

a fourth gate circuit responsive to the first gate control signal, said second gate control signal, and said actuation signal for producing a pace memory reset signal;

a fifth gate circuit responsive to the logical inverse of said second gate control signal from said third bistable circuit and to said actuation signal for producing a pace memory advance signal;

a pace memory counter, responsive to said pace memory reset signal for being reset to a count of zero and responsive to each occurrence of said pace memory advance signal for having a stored count incremented by one;

a comparator circuit for comparing the contents of said pace memory counter and said frequency divider counter and for producing a coincidence indication signal when coincidence between the contents thereof is detected;

a fourth bistable circuit responsive to an output signal from said frequency divider counter for being set to produce a first control signal, when a predetermined count of said frequency divider counter is attained, and responsive to said coincidence indication signal for being reset, thereby removing said pace gating control signal;

a fifth gate circuit coupled to receive said timebase signal and said pace gating control signal, being enabled to pass said timebase signal to an output terminal thereof by said pace getting control signal;

a pace timing divider circuit coupled to receive the output signal from said fifth gate circuit;

a delay circuit coupled to receive the output signal of said pace timing divider circuit and to produce an output signal delayed in time by a predetermined duration;

an eighth gate circuit coupled to receive the output signal from said delay circuit and said pace timing divider circuit and to receive, to thereby produce a first frequency signal;

a rhythm control circuit coupled to receive said first frequency signal and to produce a first frequency signal with rythm component;

a fourth bistable circuit responsive to alternate occurrences of the output signal from said first gate circuit for producing an output signal;

a fifth bistable circuit responsive to alternate occurrences of the output signal from said fourth bistable circuit for producing an output signal;

a first selector circuit coupled to receive said first frequency signal and said unit time signal, being responsive to the output signal from said fourth bistable circuit and to the logical inverse of said output signal for selectively passing said first frequency signal and said unit time signal to an output terminal thereof;

a combined elapsed time and step number counter cupled to receive the signal produced from said output terminal of said fifth gate circuit;

carry gate circuit means coupled to said combined elapsed time and step number counter, being responsive to the output signal from said fourth bistable circuit and to the logical inverse thereof for selectively causing said combined elapsed time and step number counter to count to a predetermined number of steps and to a predetermined elapsed time interval and to thereupon produce an elapsed time signal and a step number signal;

a repeater signal counter circuit, responsive to said actuatin signal for being reset to a count of zero;

a seventh gate circuit coupled to receive said first frequency signal and having an output terminal coupled to a clock input terminal of said repeater signal counter circuit;

comparator circuit means for comparing the count in said combined elapsed time and step number counter circuit with that in said repeater signal counter circuit and for producing a coincidence detection signal when coincidence therebetween is detected;

a fifth bistable circuit responsive to said coincidence detection signal for being set to produce an output control signal, said output control signal being applied to an input of said seventh gate circuit to enable said first frequency signal to be input to said repeater signal counter;

a second selector circuit, coupled to receive said first frequency signal and said first frequency signal having a rhythm component, and responsive to said output signal from said fifth bistable circuit and the logical inverse thereof for selectively passing said first frequency signal and said first frequency signal having a rythm component to an output terminal;

a sixth bistable circuit responsive to successive occurrences of said operating signal for alternately producing a control signal and the logical inverse of said control signal;

a ninth gate circuit, coupled to receive the output signal from said second selector circuit, and responsive to said control signal from said sixth bistable circuit for passing said output from said second selector circuit to an output terminal;

a first modulator gate circuit coupled to receive a first carrier signal from said frequency divider circuit and said repeater signal;

a second modulator gate circuit coupled to receive a modulated signal from said first modulator gate circuit, the output signal from said ninth gate circuit, and a second carrier signal from said frequency divider circuit, for thereby producing a pace signal and a modulated repeater signal;

a driver circuit coupled to receive said pace signal and modulated repeater signal, and to produce corresponding drive signals;

an electrodynamic loudspeaker driven by said drive signals to produce an audible pace timing signal and audible repeater signals indicating elapsed time intervals and numbers of steps executed.

* * * * *